United States Patent
Schneider et al.

(10) Patent No.: US 7,871,777 B2
(45) Date of Patent: Jan. 18, 2011

(54) PROBE FOR NUCLEIC ACID SEQUENCING AND METHODS OF USE

(75) Inventors: Thomas D. Schneider, Frederick, MD (US); Ilya G. Lyakhov, Frederick, MD (US); Danielle Needle, Frederick, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 126 days.

(21) Appl. No.: 12/095,973

(22) PCT Filed: Dec. 12, 2006

(86) PCT No.: PCT/US2006/047534

§ 371 (c)(1),
(2), (4) Date: Jun. 3, 2008

(87) PCT Pub. No.: WO2007/070572

PCT Pub. Date: Jun. 21, 2007

(65) Prior Publication Data

US 2008/0299565 A1 Dec. 4, 2008

Related U.S. Application Data

(60) Provisional application No. 60/749,729, filed on Dec. 12, 2005, provisional application No. 60/749,858, filed on Dec. 12, 2005.

(51) Int. Cl.
C12Q 1/68 (2006.01)
C07H 21/02 (2006.01)
C07H 21/04 (2006.01)

(52) U.S. Cl. .................. 435/6; 536/23.1; 536/24.3
(58) Field of Classification Search ............. 435/6; 536/23.1, 24.3
See application file for complete search history.

(56) References Cited

U.S. PATENT DOCUMENTS

| | | | |
|---|---|---|---|
| 5,886,177 A | 3/1999 | Cook et al. | |
| 5,998,204 A | 12/1999 | Tsien et al. | |
| 6,150,176 A | 11/2000 | Tsien et al. | |
| 6,197,928 B1 | 3/2001 | Tsien et al. | |
| 6,210,896 B1 | 4/2001 | Chan | |
| 6,495,664 B1 | 12/2002 | Cubitt | |
| 6,608,189 B1 | 8/2003 | Tsien et al. | |
| 6,682,893 B2 | 1/2004 | Taylor et al. | |
| 6,766,183 B2 | 7/2004 | Walsh et al. | |
| 6,790,632 B2 | 9/2004 | Zweig | |
| 6,890,556 B1 | 5/2005 | Segura et al. | |
| 6,908,736 B1 | 6/2005 | Densham | |
| 7,056,661 B2 | 6/2006 | Korlach et al. | |
| 7,056,676 B2 | 6/2006 | Korlach et al. | |
| 7,211,414 B2 | 5/2007 | Hardin et al. | |
| 7,297,518 B2 | 11/2007 | Quake et al. | |
| 2001/0008766 A1 | 7/2001 | Daunert et al. | |
| 2002/0137062 A1* | 9/2002 | Williams et al. | 435/6 |
| 2002/0165364 A1 | 11/2002 | Tsien et al. | |
| 2002/0193672 A1 | 12/2002 | Walsh et al. | |
| 2003/0064366 A1 | 4/2003 | Hardin et al. | |
| 2003/0170767 A1 | 9/2003 | Cubitt | |
| 2003/0212265 A1 | 11/2003 | Tsien et al. | |
| 2004/0265902 A1 | 12/2004 | Fricker et al. | |
| 2005/0267326 A1 | 12/2005 | Loeb et al. | |
| 2006/0112440 A1 | 5/2006 | Tsien et al. | |
| 2006/0211075 A1 | 9/2006 | Lawrence et al. | |

FOREIGN PATENT DOCUMENTS

| | | |
|---|---|---|
| WO | WO 98/40477 A1 | 9/1998 |
| WO | WO 00/70073 A1 | 11/2000 |
| WO | WO 01/16375 A2 | 3/2001 |
| WO | WO 02/04680 A2 | 1/2002 |
| WO | WO 02/090987 A2 | 11/2002 |
| WO | WO 2004/074503 A2 | 9/2004 |

OTHER PUBLICATIONS

Metzker et al., Termination of DNA synthesis by novel 3'-modified deoxyribonucleoside 5'-triphosphates. Nucl. Acids Res.. 22: 4259-4267 (1994).*

(Continued)

*Primary Examiner*—Ethan Whisenant
(74) *Attorney, Agent, or Firm*—Klarquist Sparkman, LLP

(57) ABSTRACT

A nanoprobe for sequencing of nucleic acid molecules is provided, as well as methods for using the nanoprobe. In particular examples, the probe includes a polymerizing agent and one or more molecular linkers that carry a chemical moiety capable of reversibly binding to the template strand of a nucleic acid molecule, without being detached from the linker, by specifically binding with a complementary nucleotide in the target nucleic acid molecule. The reversible binding of the chemical moiety on the linker with a complementary nucleotide in the target nucleic acid molecule is indicated by emission of a characteristic signal that indicates pairing of the chemical moiety on the linker with its complementary nucleotide. An example of such a chemical moiety is a non-hydrolyzable nucleotide analog. In particular examples, the polymerizing agent and the chemical moiety are associated with a tag, such as a donor fluorophore and acceptor fluorophore characteristic of the particular type of chemical moiety.

69 Claims, 12 Drawing Sheets

OTHER PUBLICATIONS

Bentley, "Whole-Genome Re-Sequencing," *Curr. Opin. Genetics Dev.* 16:545-552, 2006.

Brandis, "Dye Structure Affects *Taq* DNA Polymerase Terminator Selectivity," *Nucleic Acids Res.* 27:1912-1918, 1999.

Elçin, "Encapsulation of Urease Enzyme in Xanthan-Alignate Spheres," *Biomaterials* 16:1157-1161, 1995.

Furey et al.., "Use of Fluorescence Resonance Energy Transfer to Investigate the Conformation of DNA Substrates Bound to the Klenow Fragment," *Biochem.* 37:2979-2990, 1998.

Lemon et al., "Localization of Bacterial DNA Polymerase: Evidence for a Factory Model of Replication," *Science* 282:1516-1519, 1998.

Seeman et al., "Nanotechnology and the Double Helix," *Sci. Am.* 290:64-9, 72-5, 2004.

* cited by examiner distance between fluorophores

Rod size in Angstroms: 120 with tether 120

FRET efficiency distance between fluorophores

FIG. 4D  Rod size in Angstroms: 60 with tether 120

FRET efficiency distance between fluorophores

FIG. 4F  Rod size in Angstroms: 0 with tether 120

FRET efficiency

SEQUENCE LISTING

```
<160> NUMBER OF SEQ ID NOS: 39

<210> SEQ ID NO 1
<211> LENGTH: 30
<212> TYPE: DNA
<213> ORGANISM: Escherichia coli

<400> SEQUENCE: 1
agcttttcat tctgactgca acgggcaata                                         30

<210> SEQ ID NO 2
<211> LENGTH: 22
<212> TYPE: DNA
<213> ORGANISM: Artificial
<220> FEATURE:
<223> OTHER INFORMATION: compressed version of SEQ ID NO: 1

<400> SEQUENCE: 2
agctcatctg actgcacgca ta                                                 22
```

-continued

```
<210> SEQ ID NO 3
<211> LENGTH: 20
<212> TYPE: DNA
<213> ORGANISM: Artificial
<220> FEATURE:
<223> OTHER INFORMATION: sequence used to generate exemplary nanoprobe.

<400> SEQUENCE: 3
ggcctccgtc ctcggcagta                                              20

<210> SEQ ID NO 4
<211> LENGTH: 20
<212> TYPE: DNA
<213> ORGANISM: Artificial
<220> FEATURE:
<223> OTHER INFORMATION: sequence used to generate exemplary nanoprobe.

<400> SEQUENCE: 4
tactgccgag gacggaggcc                                              20

<210> SEQ ID NO 5
<211> LENGTH: 20
<212> TYPE: DNA
<213> ORGANISM: Artificial
<220> FEATURE:
<223> OTHER INFORMATION: sequence used to generate exemplary nanoprobe.

<400> SEQUENCE: 5
cgataatgcc tgtcatgcat                                              20

<210> SEQ ID NO 6
<211> LENGTH: 20
<212> TYPE: DNA
<213> ORGANISM: Artificial
<220> FEATURE:
<223> OTHER INFORMATION: sequence used to generate exemplary nanoprobe.

<400> SEQUENCE: 6
atgcatgaca ggcattatcg                                              20

<210> SEQ ID NO 7
<211> LENGTH: 19
<212> TYPE: DNA
<213> ORGANISM: Artificial
<220> FEATURE:
<223> OTHER INFORMATION: sequence used to generate exemplary nanoprobe.

<400> SEQUENCE: 7
gaacgtctag acttatcgc                                               19

<210> SEQ ID NO 8
<211> LENGTH: 20
<212> TYPE: DNA
<213> ORGANISM: Artificial
<220> FEATURE:
<223> OTHER INFORMATION: sequence used to generate exemplary nanoprobe.

<400> SEQUENCE: 8
gcgataagtc tagacgttcc                                              20

<210> SEQ ID NO 9
<211> LENGTH: 20
<212> TYPE: DNA
<213> ORGANISM: Artificial
<220> FEATURE:
<223> OTHER INFORMATION: sequence used to generate exemplary nanoprobe.
```

<400> SEQUENCE: 9
ctctcgctcc gtgccgtaag                                         20

<210> SEQ ID NO 10
<211> LENGTH: 20
<212> TYPE: DNA
<213> ORGANISM: Artificial
<220> FEATURE:
<223> OTHER INFORMATION: sequence used to generate exemplary nanoprobe.

<400> SEQUENCE: 10
cttacggcac ggagcgagag                                         20

<210> SEQ ID NO 11
<211> LENGTH: 71
<212> TYPE: DNA
<213> ORGANISM: Artificial
<220> FEATURE:
<223> OTHER INFORMATION: sequence used to generate exemplary nanoprobe.

<400> SEQUENCE: 11
cgctcctgaa ttcgacgtac gctatatatt tagtatgttg taactaaagt ccagcgcgaa      60
gcttaatgac t                                                  71

<210> SEQ ID NO 12
<211> LENGTH: 71
<212> TYPE: DNA
<213> ORGANISM: Artificial
<220> FEATURE:
<223> OTHER INFORMATION: sequence used to generate exemplary nanoprobe.

<400> SEQUENCE: 12
attcagtctg caggaaggcc gactttagtt acaacatact aaatatatag ccagtaaggg      60
atccgatctc g                                                  71

<210> SEQ ID NO 13
<211> LENGTH: 20
<212> TYPE: DNA
<213> ORGANISM: Artificial
<220> FEATURE:
<223> OTHER INFORMATION: sequence used to generate exemplary nanoprobe.

<400> SEQUENCE: 13
gtacgtcgaa ttcaggagcg                                         20

<210> SEQ ID NO 14
<211> LENGTH: 20
<212> TYPE: DNA
<213> ORGANISM: Artificial
<220> FEATURE:
<223> OTHER INFORMATION: sequence used to generate exemplary nanoprobe.

<400> SEQUENCE: 14
cgagatcgga tcccttactg                                         20

<210> SEQ ID NO 15
<211> LENGTH: 20
<212> TYPE: DNA
<213> ORGANISM: Artificial
<220> FEATURE:
<223> OTHER INFORMATION: sequence used to generate exemplary nanoprobe.

<400> SEQUENCE: 15
agtcattaag cttcgcgctg                                         20

<210> SEQ ID NO 16
<211> LENGTH: 20
<212> TYPE: DNA
<213> ORGANISM: Artificial
<220> FEATURE:
<223> OTHER INFORMATION: sequence used to generate exemplary nanoprobe.

<400> SEQUENCE: 16
ggccttcctg cagactgaat                                                   20

<210> SEQ ID NO 17
<211> LENGTH: 45
<212> TYPE: DNA
<213> ORGANISM: Artificial
<220> FEATURE:
<223> OTHER INFORMATION: sequence used to generate exemplary nanoprobe.
<220> FEATURE:
<221> NAME/KEY: misc_feature
<222> LOCATION: (21)..(23)
<223> OTHER INFORMATION: n is PEG18
<220> FEATURE:
<221> NAME/KEY: misc_feature
<222> LOCATION: (44)..(44)
<223> OTHER INFORMATION: n is PEG9
<220> FEATURE:
<221> NAME/KEY: misc_feature
<222> LOCATION: (45)..(45)
<223> OTHER INFORMATION: n is NH2

<400> SEQUENCE: 17
gtacgtcgaa ttcaggagcg nnntactgcc gaggacggag gccnn                       45

<210> SEQ ID NO 18
<211> LENGTH: 45
<212> TYPE: DNA
<213> ORGANISM: Artificial
<220> FEATURE:
<223> OTHER INFORMATION: sequence used to generate exemplary nanoprobe.
<220> FEATURE:
<221> NAME/KEY: misc_feature
<222> LOCATION: (1)..(1)
<223> OTHER INFORMATION: n is NH2
<220> FEATURE:
<221> NAME/KEY: misc_feature
<222> LOCATION: (2)..(2)
<223> OTHER INFORMATION: n is PEG9
<220> FEATURE:
<221> NAME/KEY: misc_feature
<222> LOCATION: (23)..(25)
<223> OTHER INFORMATION: n is PEG 18

<400> SEQUENCE: 18
nnatgcatga caggcattat cgnnncgaga tcggatccct tactg                       45

<210> SEQ ID NO 19
<211> LENGTH: 45
<212> TYPE: DNA
<213> ORGANISM: Artificial
<220> FEATURE:
<223> OTHER INFORMATION: sequence used to generate exemplary nanoprobe.
<220> FEATURE:
<221> NAME/KEY: misc_feature
<222> LOCATION: (1)..(1)
<223> OTHER INFORMATION: n is NH2
<220> FEATURE:
<221> NAME/KEY: misc_feature
<222> LOCATION: (2)..(2)
<223> OTHER INFORMATION: n is PEG9
<220> FEATURE:
<221> NAME/KEY: misc_feature
<222> LOCATION: (23)..(25)

```
<223> OTHER INFORMATION: n is PEG18

<400> SEQUENCE: 19
nngcgataag tctagacgtt ccnnnagtca ttaagcttcg cgctg                45

<210> SEQ ID NO 20
<211> LENGTH: 45
<212> TYPE: DNA
<213> ORGANISM: Artificial
<220> FEATURE:
<223> OTHER INFORMATION: sequence used to generate exemplary nanoprobe.
<220> FEATURE:
<221> NAME/KEY: misc_feature
<222> LOCATION: (21)..(23)
<223> OTHER INFORMATION: n is PEG18
<220> FEATURE:
<221> NAME/KEY: misc_feature
<222> LOCATION: (44)..(44)
<223> OTHER INFORMATION: n is PEG9
<220> FEATURE:
<221> NAME/KEY: misc_feature
<222> LOCATION: (45)..(45)
<223> OTHER INFORMATION: n is NH2

<400> SEQUENCE: 20
ggccttcctg cagactgaat nnncttacgg cacggagcga gagnn                45

<210> SEQ ID NO 21
<211> LENGTH: 71
<212> TYPE: DNA
<213> ORGANISM: Artificial
<220> FEATURE:
<223> OTHER INFORMATION: sequence used to generate exemplary nanoprobe.

<400> SEQUENCE: 21
cgctcctgaa ttcgacgtac gctatatatt tagtatgttg taactaaagt ccagcgcgaa   60
gcttaatgac t                                                        71

<210> SEQ ID NO 22
<211> LENGTH: 71
<212> TYPE: DNA
<213> ORGANISM: Artificial
<220> FEATURE:
<223> OTHER INFORMATION: sequence used to generate exemplary nanoprobe.

<400> SEQUENCE: 22
attcagtctg caggaaggcc gactttagtt acaacatact aaatatatag ccagtaaggg   60
atccgatctc g                                                        71

<210> SEQ ID NO 23
<211> LENGTH: 44
<212> TYPE: DNA
<213> ORGANISM: Artificial
<220> FEATURE:
<223> OTHER INFORMATION: sequence used to generate exemplary nanoprobe.
<220> FEATURE:
<221> NAME/KEY: misc_feature
<222> LOCATION: (21)..(23)
<223> OTHER INFORMATION: n is PEG18
<220> FEATURE:
<221> NAME/KEY: misc_feature
<222> LOCATION: (44)..(44)
<223> OTHER INFORMATION: n is
      [PEG9]-NH-POOH-O-POOH-CH2-POOH-deoxyadenosine

<400> SEQUENCE: 23
gtacgtcgaa ttcaggagcg nnntactgcc gaggacggag gccn                    44
```

<210> SEQ ID NO 24
<211> LENGTH: 44
<212> TYPE: DNA
<213> ORGANISM: Artificial
<220> FEATURE:
<223> OTHER INFORMATION: sequence used to generate exemplary nanoprobe.
<220> FEATURE:
<221> NAME/KEY: misc_feature
<222> LOCATION: (21)..(23)
<223> OTHER INFORMATION: n is PEG18
<220> FEATURE:
<221> NAME/KEY: misc_feature
<222> LOCATION: (44)..(44)
<223> OTHER INFORMATION: n is
    [PEG9]-NH-POOH-O-POOH-CH2-POOH-deoxythymidine

<400> SEQUENCE: 24
ggccttcctg cagactgaat nnncttacgg cacggagcga gagn            44

<210> SEQ ID NO 25
<211> LENGTH: 44
<212> TYPE: DNA
<213> ORGANISM: Artificial
<220> FEATURE:
<223> OTHER INFORMATION: sequence used to generate exemplary nanoprobe.
<220> FEATURE:
<221> NAME/KEY: misc_feature
<222> LOCATION: (1)..(1)
<223> OTHER INFORMATION: n is
    deoxyguanosine-POOH-CH2-POOH-O-POOH-NH-[PEG9]
<220> FEATURE:
<221> NAME/KEY: misc_feature
<222> LOCATION: (22)..(24)
<223> OTHER INFORMATION: n is PEG18

<400> SEQUENCE: 25
ngcgataagt ctagacgttc cnnnagtcat taagcttcgc gctg            44

<210> SEQ ID NO 26
<211> LENGTH: 44
<212> TYPE: DNA
<213> ORGANISM: Artificial
<220> FEATURE:
<223> OTHER INFORMATION: sequence used to generate exemplary nanoprobe.
<220> FEATURE:
<221> NAME/KEY: misc_feature
<222> LOCATION: (1)..(1)
<223> OTHER INFORMATION: n is
    deoxycytidine-POOH-CH2-POOH-O-POOH-NH-[PEG9]
<220> FEATURE:
<221> NAME/KEY: misc_feature
<222> LOCATION: (22)..(24)
<223> OTHER INFORMATION: n is PEG18

<400> SEQUENCE: 26
natgcatgac aggcattatc gnnncgagat cggatccctt actg            44

<210> SEQ ID NO 27
<211> LENGTH: 22
<212> TYPE: DNA
<213> ORGANISM: Artificial
<220> FEATURE:
<223> OTHER INFORMATION: sequence used to generate exemplary nanoprobe.
<220> FEATURE:
<221> NAME/KEY: misc_feature
<222> LOCATION: (1)..(1)
<223> OTHER INFORMATION: n is Cy3
<220> FEATURE:
<221> NAME/KEY: misc_feature
<222> LOCATION: (2)..(2)
<223> OTHER INFORMATION: n is Cy5

```
<400> SEQUENCE: 27
nnggcctccg tcctcggcag ta                                              22

<210> SEQ ID NO 28
<211> LENGTH: 22
<212> TYPE: DNA
<213> ORGANISM: Artificial
<220> FEATURE:
<223> OTHER INFORMATION: sequence used to generate exemplary nanoprobe.
<220> FEATURE:
<221> NAME/KEY: misc_feature
<222> LOCATION: (21)..(21)
<223> OTHER INFORMATION: n is Cy3
<220> FEATURE:
<221> NAME/KEY: misc_feature
<222> LOCATION: (22)..(22)
<223> OTHER INFORMATION: n is Texas Red

<400> SEQUENCE: 28
cgataatgcc tgtcatgcat nn                                              22

<210> SEQ ID NO 29
<211> LENGTH: 22
<212> TYPE: DNA
<213> ORGANISM: Artificial
<220> FEATURE:
<223> OTHER INFORMATION: sequence used to generate exemplary nanoprobe.
<220> FEATURE:
<221> NAME/KEY: misc_feature
<222> LOCATION: (21)..(21)
<223> OTHER INFORMATION: n is Cy3
<220> FEATURE:
<221> NAME/KEY: misc_feature
<222> LOCATION: (22)..(22)
<223> OTHER INFORMATION: n is Rhodamine Red

<400> SEQUENCE: 29
ggaacgtcta gacttatcgc nn                                              22

<210> SEQ ID NO 30
<211> LENGTH: 23
<212> TYPE: DNA
<213> ORGANISM: Artificial
<220> FEATURE:
<223> OTHER INFORMATION: sequence used to generate exemplary nanoprobe.
<220> FEATURE:
<221> NAME/KEY: misc_feature
<222> LOCATION: (1)..(1)
<223> OTHER INFORMATION: n is Cy5
<220> FEATURE:
<221> NAME/KEY: misc_feature
<222> LOCATION: (2)..(2)
<223> OTHER INFORMATION: n is Texas Red
<220> FEATURE:
<221> NAME/KEY: misc_feature
<222> LOCATION: (3)..(3)
<223> OTHER INFORMATION: n is Rhodamine Red

<400> SEQUENCE: 30
nnnctctcgc tccgtgccgt aag                                             23

<210> SEQ ID NO 31
<211> LENGTH: 66
<212> TYPE: DNA
<213> ORGANISM: Artificial
<220> FEATURE:
<223> OTHER INFORMATION: oligonucleotide that can form a haipin
<220> FEATURE:
<221> NAME/KEY: misc_feature
<222> LOCATION: (1)..(1)
<223> OTHER INFORMATION: n is Alexa Flour 488
```

<400> SEQUENCE: 31
ntcgagtttg ctcagaattc gatcacgatc gcgcgaagcg cgatcgtgat cgaattctga        60
gcaaac                                                                   66

<210> SEQ ID NO 32
<211> LENGTH: 67
<212> TYPE: DNA
<213> ORGANISM: Artificial
<220> FEATURE:
<223> OTHER INFORMATION: oligonucleotide that can form a haipin
<220> FEATURE:
<221> NAME/KEY: misc_feature
<222> LOCATION: (1)..(1)
<223> OTHER INFORMATION: n is Alexa Flour 488
<220> FEATURE:
<221> NAME/KEY: misc_feature
<222> LOCATION: (67)..(67)
<223> OTHER INFORMATION: n is a dUTP labeled with Alexa Fluor 594

<400> SEQUENCE: 32
ntcgagtttg ctcagaattc gatcacgatc gcgcgaagcg cgatcgtgat cgaattctga        60 gcaaacn                                                                  67

<210> SEQ ID NO 33
<211> LENGTH: 66
<212> TYPE: DNA
<213> ORGANISM: Artificial
<220> FEATURE:
<223> OTHER INFORMATION: oligonucleotide that can form a haipin
<220> FEATURE:
<221> NAME/KEY: misc_feature
<222> LOCATION: (1)..(1)
<223> OTHER INFORMATION: n is Alexa Fluor 555

<400> SEQUENCE: 33
ntcgagtttg ctcagaattc gatcacgatc gcgcgaagcg cgatcgtgat cgaattctga        60
gcaaac                                                                   66

<210> SEQ ID NO 34
<211> LENGTH: 30
<212> TYPE: DNA
<213> ORGANISM: Artificial
<220> FEATURE:
<223> OTHER INFORMATION: oligonucleotide that can form a haipin

<400> SEQUENCE: 34
tttgcagtcg gactaccgcg gtagtccgac                                         30

<210> SEQ ID NO 35
<211> LENGTH: 31
<212> TYPE: DNA
<213> ORGANISM: Artificial
<220> FEATURE:
<223> OTHER INFORMATION: oligonucleotide that can form a haipin

<400> SEQUENCE: 35
tttgcagtcg gactaccgcg gtagtccgac t                                       31

<210> SEQ ID NO 36
<211> LENGTH: 32
<212> TYPE: DNA
<213> ORGANISM: Artificial
<220> FEATURE:
<223> OTHER INFORMATION: oligonucleotide that can form a haipin -continued

```
<400> SEQUENCE: 36
tttgcagtcg gactaccgcg gtagtccgac tg                                  32

<210> SEQ ID NO 37
<211> LENGTH: 33
<212> TYPE: DNA
<213> ORGANISM: Artificial
<220> FEATURE:
<223> OTHER INFORMATION: oligonucleotide that can form a haipin

<400> SEQUENCE: 37
tttgcagtcg gactaccgcg gtagtccgac tgc                                 33

<210> SEQ ID NO 38
<211> LENGTH: 36
<212> TYPE: DNA
<213> ORGANISM: Artificial
<220> FEATURE:
<223> OTHER INFORMATION: oligonucleotide that can form a haipin

<400> SEQUENCE: 38
tttgcagtcg gactaccgcg gtagtccgac tgcaaa                              36

<210> SEQ ID NO 39
<211> LENGTH: 9
<212> TYPE: DNA
<213> ORGANISM: Artificial
<220> FEATURE:
<223> OTHER INFORMATION: exemplary target sequence

<400> SEQUENCE: 39 acgttcagt                                                             9
```

PROBE FOR NUCLEIC ACID SEQUENCING AND METHODS OF USE

CROSS-REFERENCE TO RELATED APPLICATIONS

This is the U.S. National Stage of International Application No. PCT/US2006/047534, filed Dec. 12, 2006 (published in English under PCT Article 21(2)), which claims the benefit of U.S. Provisional Application Nos. 60/749,729 and 60/749,858 both filed Dec. 12, 2005 and herein incorporated by reference.

FIELD

This disclosure relates to probes and methods for sequencing nucleic acid molecules, such as DNA and RNA, which can be used for research and the diagnosis of disease in clinical applications.

BACKGROUND

Numerous methods have been used to sequence nucleic acid molecules. The traditional Maxam-Gilbert chemical degradation method involves the chemical-specific cleavage of DNA (Maxam and Gilbert, *Proc. Natl. Acad. Sci., USA* 74:560, 1977). In this method, radio-labeled DNA molecules are incubated in four separate reaction mixtures, each of which partially cleaves the DNA at one or two nucleotides of a specific identity (G, A+G, C or C+T). The resulting DNA fragments are separated by polyacrylamide gel electrophoresis, with each of the four reactions fractionated in a separate lane of the gel. The DNA sequence is determined after autoradiography by observing the macromolecular separation of the fragments in the four lanes of the gel.

The Sanger dideoxy chain termination method involves generating DNA molecules of differing lengths by enzymatic extension of a synthetic primer, using DNA polymerase and a mixture of deoxy- and dideoxy-nucleoside triphosphates (Sanger et al., *Proc. Natl. Acad. Sci.*, USA 74:5463, 1977). The reactions are separated in four parallel lanes on polyacrylamide gels and the sequence determined after autoradiography.

The use of fluorescent nucleotides has eliminated the need for radioactive nucleotides, and provides a means to automate DNA sequencing (for example see U.S. Pat. No. 5,124,247 to Ansorge, U.S. Pat. No. 5,242,796 to Prober et al., U.S. Pat. No. 5,306,618 to Prober et al., U.S. Pat. No. 5,360,523 to Middendorf et al., U.S. Pat. No. 5,556,790 to Pettit, and U.S. Pat. No. 5,821,058 to Smith et al.). However, methods that use fluorophores generally still require gels or capillary electrophoresis, and thus are slow and macroscopic.

Another potential obstacle with using fluorescently labeled dNTPs is that no one has been able to synthesize a fully fluorescently labeled DNA molecule. Therefore, sequencing methods that permit the synthesis of the complementary nucleic acid strand are still needed.

SUMMARY

The present disclosure provides an improved probe that can be used in the sequencing of nucleic acid molecules, and methods for using the probe. In particular examples the probe can be used to determine the transcription levels of one or more genes. For example, the probe can be used to count individual RNA transcripts, thereby providing an estimate of the number produced in a cell. In particular examples, the probes and methods disclosed herein are used as an alternative to currently available microarray technologies.

In particular examples, the probe, named "Medusa", includes a polymerizing agent with one or more (such as a plurality of) molecular linkers attached to the polymerizing agent to link (and in some examples space) one or more chemical moieties (such as a nonhydrolyzable nucleotide) to the polymerizing agent. The chemical moieties are capable of reversibly binding to the template strand of a nucleic acid molecule, without being detached from the linker, by specifically binding with a complementary nucleotide in the target nucleic acid molecule. In disclosed examples the reversible incorporation occurs at the active site of the polymerizing agent. However, ideally the chemical moieties are not capable of being permanently incorporated into a growing nucleic acid strand. The specific binding of the chemical moiety on the linker with a complementary nucleotide in the target nucleic acid molecule is indicated by emission of a characteristic signal that indicates pairing of the chemical moiety on the linker with its complementary nucleotide.

The polymerizing agent includes an active site that is capable of binding to the target nucleic acid molecule to be sequenced, and in some examples is capable of promoting synthesis of a nucleic acid molecule complementary to the target nucleic acid molecule, wherein the complementary nucleic acid molecule elongates as complementary nucleotides are incorporated into the complementary nucleic acid molecule. Polymerizing agents include compounds capable of reacting monomer molecules (such as nucleotides) together in a chemical reaction to form linear chains (such as a complementary nucleic acid molecule). Exemplary polymerizing agents include but are not limited to, DNA polymerase, RNA polymerase, and reverse transcriptase. In particular examples, the polymerase is a GFP-polymerase. The choice of polymerizing agent can depend on the nucleic acid to be sequenced. For example, if the target nucleic acid molecule is DNA, the polymerizing agent can be a DNA or RNA polymerase, while if the target nucleic acid molecule is RNA, the polymerizing agent can be a reverse transcriptase.

The chemical moiety that is capable of reversibly binding to a complementary nucleotide in the template strand of the target nucleic acid molecule, without being detached from the linker, can include a nucleotide analog, such as a non-hydrolyzable nucleotide analog. Such analogs can pair with a complementary nucleotide in the target nucleic acid molecule, but are not permanently incorporated into the elongating complementary nucleic acid strand. Non-hydrolyzable nucleotide analogs are known in the art, and include non-hydrolyzable triphosphate nucleotide analogs, such as a non-hydrolyzable triphosphate nucleotide analog with an alpha-beta bond that is non-hydrolyzable.

In particular examples, the probe includes at least four independent linkers, each of which carries a different chemical moiety capable of specifically pairing with a different nucleotide in the target nucleic acid molecule, but not capable of being permanently incorporated into the elongating complementary nucleic acid molecule. In other examples, the probe includes a plurality of linkers that are joined to form a branched structure, wherein each branch carries a different chemical moiety capable of specifically pairing with a different nucleotide in the target nucleic acid molecule, but not capable of being permanently incorporated into the elongating complementary nucleic acid molecule. For example, the branched structure may only attach to the polymerizing agent at one point.

The molecular linker links the polymerizing agent to one or more chemical moieties that are capable of reversibly binding to the template (or target) strand of a nucleic acid molecule. In particular examples, the molecular linker maintains the polymerizing agent and the chemical moieties sufficiently spaced a distance from one another to avoid substantial entanglement of the polymerizing agent and the chemical moieties in the absence of the target or template nucleic acid molecule, while allowing interaction of the polymerizing agent and the chemical moieties in the presence of the target nucleic acid molecule. For example, the molecular linkers can be spaced around the polymerizing agent a sufficient distance to inhibit entanglement of the linkers, and are of sufficient length to reach the active site of the polymerizing agent. In some examples, the molecular linker (or at least a portion thereof) is of sufficient rigidity to reduce interaction of the polymerizing enzyme and the chemical moieties in the absence of the target nucleic acid molecule.

The molecular linker (or a portion thereof, such as a molecular rod that is part of the molecular linker) has a sufficient length in view of its flexibility to space the polymerizing agent and the chemical moieties sufficiently apart to avoid the undesired interaction in the absence of the target nucleic acid molecule, but retain sufficient flexibility to allow the polymerizing agent and the chemical moieties to interact with each other and with the target nucleic acid molecule, for example when the polymerizing agent binds to the target nucleic acid molecule. For example, at least part of the molecular linker can have a persistence length that permits at least a portion of the molecular linker to be of sufficient rigidity and length to reduce interaction of the polymerizing agent (such as a tag associated with the polymerizing agent) and the chemical moieties in the absence of the target nucleic acid molecule, and allows interaction of the polymerizing agent and the chemical moieties in the presence of the target nucleic acid molecule.

In particular examples, the total length of the molecular linker is different than (such as greater or less than) the persistence length of one or more components that make up the linker, such as a double- or single-stranded nucleic acid molecule. However, in particular examples, the total length of the molecular linker does not exceed a length beyond which significant interaction occurs between the polymerizing agent and the chemical moieties in the absence of the target nucleic acid molecule, while allowing significant interaction of the polymerizing agent and the chemical moieties, as well as the target nucleic acid molecule, in the presence of the target nucleic acid molecule. Such interactions can be measured using methods known in the art, for example by measuring acceptor emission fluorescence when the polymerizing agent includes a donor fluorophore and one or more chemical moieties include a corresponding acceptor fluorophore of a FRET pair. In other examples, a polymerizing agent is substantially maintained at a distance of at least twice the Förster radius (such as a Förster radius of 22 to 90 Å) from the chemical moieties in the absence of the target.

Persistence length (lp) is the average local conformation for a linear chain, which reflects the sum of the average projections of all chain segments on a direction described by a given segment. Therefore, persistence length is a measure of the rigidity or stiffness of a polymer chain. In particular examples, persistence length is the degree of bending (and hence the effective stiffness of the chain) which, in effect, measures the contour distance over which there occurs, on the average, a 68.40° bend. Therefore, the persistence length will vary depending on the composition of the molecular linker. For example, the persistence length for a double-stranded DNA (dsDNA) molecule will differ from that of a single-stranded DNA (ssDNA) molecule and from polyethylene glycol (PEG). In particular examples, dsDNA has a persistence length of about 400-500 Å (such as 450-500 Å), and dsRNA has a persistence length of 700-750 Å, for example at an ionic strength of about 0.2 M and at a temperature of 20° C. In particular examples, ssDNA has a persistence length of about 40 Å (for example at 20° C.) (Clossey and Carlon, *Phys. Rev. E. Stat. Nonlin. Soft. Matter. Phys.* 68(6 Pt 1):061911, 2003). In particular examples, PEG has a persistence length of about 3.8 Å.

In particular examples, the molecular linkers include linear polymers, such as polymers of nucleic acids, amino acids, sugar, PEG, or combinations thereof. For example, molecular linkers include, but are not limited to, tethers, molecular rods, or combinations thereof. For example, the molecular linker of sufficient rigidity can include a molecular rod, for example a molecular rod composed of a dsDNA. In some examples, the molecular linker of sufficient rigidity includes multiple molecular rods linked by tethers, or multiple tethers linked by molecular rods. One particular example of a tether is a molecule composed of (or in some examples consisting of) polyethylene glycol (PEG).

The polymerizing agent and the chemical moieties can be linked in a spatially separated orientation by one or more molecular linkers so that the polymerizing agent and the chemical moieties do not interact to provide the reaction in the absence of the target nucleic acid molecule. However, the molecular linker permits the polymerizing agent and the chemical moieties, under predetermined conditions, to be brought into sufficient proximity with one another to interact and produce a predetermined reaction, such as a detectable signal or interaction with the target nucleic acid molecule. For example, at least one of the tags associated with the polymerizing agent or the chemical moiety can be activated when brought into sufficient proximity to another tag, such as the excitation of an acceptor fluorophore tag by a donor fluorophore tag when the donor and acceptor are in sufficient proximity with one another.

Also provided by the present disclosure is a polymerizing agent that includes an active site capable of binding to a target nucleic acid molecule and promoting synthesis of a complementary nucleic acid molecule that elongates as complementary nucleotides are incorporated into the complementary nucleic acid molecule. The polymerizing agent further includes one or more molecular linkers spaced apart on the polymerizing agent to inhibit entanglement, wherein each linker carries a different chemical moiety (such as a nonhydrolyzable nucleotide analog) that is capable of reversibly binding to the template strand of a nucleic acid molecule, without being detached from the linker, by specifically binding with a complementary nucleotide in the target nucleic acid molecule. In particular examples, the polymerizing agent further includes a tag associated with each chemical moiety that identifies the chemical moiety carried by the linker. In addition, the polymerase can be associated with a tag that interacts with the tag associated with the chemical moiety to emit a characteristic signal that identifies the chemical moiety carried by the linker.

Also provided by the present disclosure are methods of using the disclosed nanoprobes, for example to determine the nucleic acid sequence of a target nucleic acid molecule. In particular examples, the method is used to determine if a particular target molecule is present in a sample, and in some examples includes quantitating the amount of target nucleic acid molecule present. For example, methods are provided for using the probe to diagnose a subject having a disease that is associated with one or more nucleic acid mutations.

Sequencing can be done in vitro or in situ (for example on a microscope slide) and in vivo (for example by introducing the probe into a cell and observing the sequences of mRNA as they are produced). The method allows several nucleic acids to be sequenced simultaneously at the molecular level. For example, a plurality of sequencing reactions can be performed substantially simultaneously, and the signals from the plurality of sequencing reactions detected and converted into a nucleic acid sequence.

In particular examples, the method includes exposing the target nucleic acid molecule to the probes disclosed herein in the presence of an oligonucleotide primer and a mixture of hydrolyzable nucleotides (such as dATP, dCTP, dGTP, and dTTP or ATP, CTP, GTP and UTP) that are capable of being incorporated into an elongating nucleic acid molecule by base pairing with a complementary nucleotide in the target nucleic acid molecule, and replacing the chemical moiety carried by the linker that reversibly binds to the template strand of the nucleic acid molecule. The emission of a sequence of signals is detected, wherein the signals include the emission of a plurality of the characteristic signals that indicates pairing of the chemical moiety on the linker with its complementary nucleotide. In some examples, the emission of a sequence of signals is converted into a nucleic acid sequence.

In particular examples, the polymerizing agent is associated with a tag (such as a donor fluorophore), and each different type of chemical moiety (such as a non-hydrolyzable A, T/U, C or G nucleotide analog) is associated with a unique tag that identifies the particular chemical moiety carried by the linker, wherein interaction of the tag associated with the polymerizing agent with the tag associated with the chemical moiety induces emission of the characteristic signal that indicates pairing of the chemical moiety on the linker with its complementary nucleotide. In particular examples, the tag is directly attached to the polymerizing agent or the chemical moiety. However, the tag need not be directly attached, and instead can be found on a molecular linker in sufficient proximity to the polymerizing agent or the chemical moiety to produce an emission of the characteristic signal when the chemical moiety on the linker pairs with its complementary nucleotide.

For example, the tag associated with the polymerizing agent can be a donor fluorophore and the tag that identifies a particular chemical moiety can include one or more acceptor fluorophores, wherein interaction of the polymerizing agent and the chemical moiety that cannot be incorporated into a synthesized nucleic acid molecule brings the acceptor fluorophore into a proximity with a donor fluorophore that permits excitation of the acceptor fluorophore by the donor fluorophore. In such an example, detecting the signal can include detecting a fluorescent signal emitted from the acceptor fluorophore (or a decreased emission signal from the donor fluorophore). In particular examples, the method further includes exciting the donor fluorophore by a source of electromagnetic radiation (such as a laser) that specifically excites the donor fluorophore and not the acceptor fluorophores. Alternatively, the donor fluorophore is a chemiluminescent molecule, for example aequorin. In this example, the donor fluorophore does not require excitation by a source of electromagnetic radiation, because the chemiluminescent donor fluorophore is naturally in an excited state. This excitation induces the donor to emit light at a wavelength that can transfer energy a distance only sufficient to excite the acceptor fluorophore(s) associated with the chemical moiety that is pairing with the target nucleic acid molecule.

In particular examples, the probe is attached or fixed to a substrate, for example in an addressable location via a linker molecule that attaches the polymerase component to the substrate. Exemplary linkers include streptavidin-biotin, histidine-Ni, S-tag-S-protein, and glutathione-glutathione-S-transferase (GST). In another example, the target nucleic acid molecule to be sequenced is attached or fixed to a substrate, for example in an addressable location. In particular examples the oligonucleotide primer is fixed to a substrate, for example at its 5' end. For example, a nucleic acid molecule can be attached to the substrate by its 5' end, 3' end or anywhere in between. In particular examples, the sequencing reaction is performed in a three dimensional polyacrylamide gel, wherein all of the reagents needed for sequencing are present in the gel.

In some examples, a plurality of probes, primers, or nucleic acid molecules are fixed directly or indirectly to the substrate in a predetermined pattern, for example in an addressable location. For example, the agents can be deposited into channels which have been etched in an orderly array or by micropipetting droplets containing the agent onto a slide, for example either by manually pipetting or with an automated arrayer. Such methods permit simultaneous (or substantially simultaneous) sequencing on a single substrate, in which case signals are detected from each of the sequencing reactions. The unique emission signals can be detected, for example with a charge-coupled device (CCD) camera, which can detect a sequence of signals from a predetermined position on the substrate and convert them into the nucleic acid sequence. The unique emission signals can be stored in a computer-readable medium.

The foregoing and other features and advantages of the disclosure will become more apparent from the following detailed description of several examples which proceeds with reference to the accompanying figures.

(B) tether length 60 Å; (C) tether length 120 Å; (D) tether length 240 Å. The data of the graphs of FIG. 4 can be obtained from the lower left part of FIG. 5 (such as FIG. 5C, with a tether length of 120 Å) by taking vertical slices at rod lengths of 0 Å, 60 Å and 120 Å. The data were generated using the bite program and graphed using programs genhis and denplo.

Figure 6:
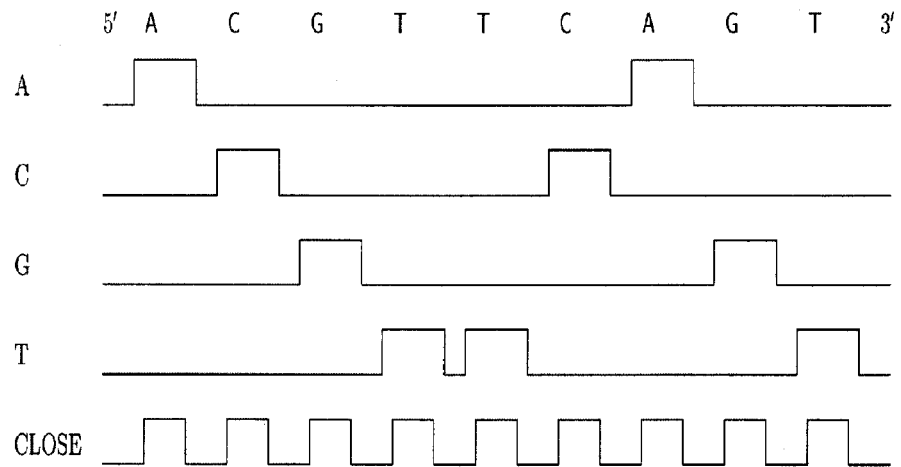

FIG. 6 is a trace showing an example result for a target sequence.

Figures 7, 8:
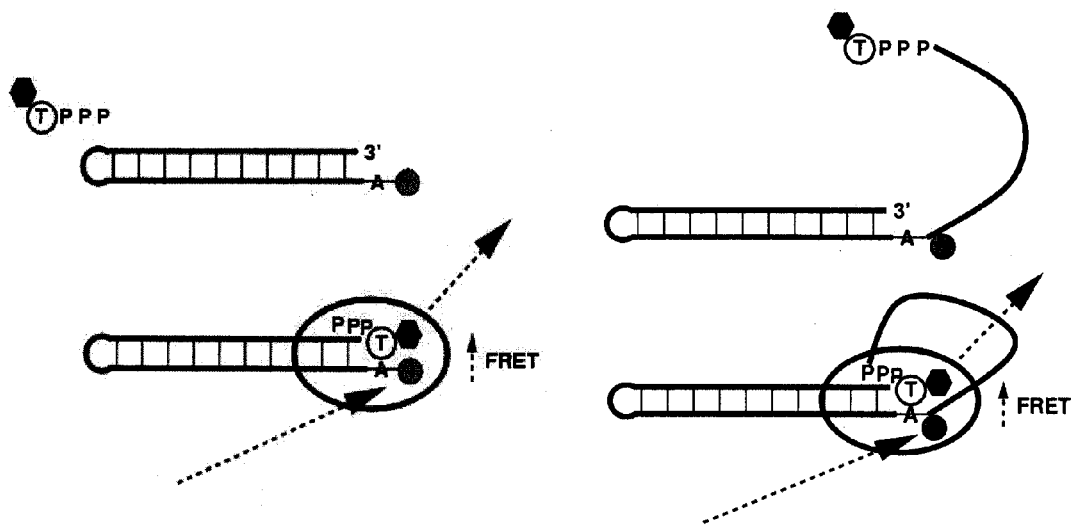

FIG. 7 is a schematic drawing illustrating (top) a hairpin oligonucleotide having a 5' overhang and fluorescent donor label (circle), and a 3' dideoxynucleotide. A freely diffusing dTTP is labeled with a FRET acceptor (hexagon). The labeled dTTP can bind to the first base of the overhang, but the dTTP cannot be incorporated into the oligonucleotide. The bottom shows FRET between the donor and acceptor when the labeled dTTP is held to the hairpin by a polymerase (ellipse). This dwell can be measured using methods known in the art, for example using fluorescence correlation spectroscopy (FCS).

FIG. 8 is a schematic drawing illustrating (top) a hairpin oligonucleotide ending with a dideoxynucleotide at the 3' end and having a donor fluorophore near the 5' end. An acceptor-labeled dTTP is attached via a PEG tether. Although the first base in the overhang is an A, the tethered dTTP will not stay close to the "A" and little or no FRET should occur. The bottom shows that when a DNA polymerase (ellipse) binds to the DNA hairpin, the tethered dTTP should dwell in the enzyme-DNA pocket, allowing FRET between the two fluorophores.

SEQUENCE LISTING

The nucleic acid sequences listed in the accompanying sequence listing are shown using standard letter abbreviations for nucleotide bases. In particular examples, only one strand of a nucleic acid sequence is shown, but the complementary strand is understood as included by any reference to the displayed strand (for example in the case of a dsDNA molecular rod).

SEQ ID NO: 1 is an exemplary target sequence.
SEQ ID NO: 2 is the compressed version of SEQ ID NO: 1.
SEQ ID NOS: 3-26 are sequences that can be used to generate the probe shown in FIG. 2C.
SEQ ID NOS: 27-30 are sequences that can be substituted for SEQ ID NOS: 3, 5, 7, and 9, respectively.
SEQ ID NOS: 31-38 are sequences that can form hairpin loops.
SEQ ID NO: 39 is an exemplary target sequence.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "a molecular linker" includes one or a plurality of such molecular linkers, and reference to "the probe" includes reference to one or more probes and equivalents thereof known to those skilled in the art, and so forth. The term "or" refers to a single element of stated alternative elements or a combination of two or more elements, unless the context clearly indicates otherwise. For example, the phrase "a tether or a molecular rod" refers to one or more tethers, one or more molecular rods, or a combination of both one or more tethers and one or more molecular rods.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features and advantages of the disclosure are apparent from the following detailed description and the claims.

| | |
|---|---|
| Å | angstrom |
| dsDNA | double-stranded DNA |
| FRET | Förster resonance energy transfer |
| GFP | green fluorescent protein |
| LNA | locked nucleic acid |
| PEG | polyethylene glycol |
| PNA | peptide nucleic acid |
| RT | reverse transcriptase |
| ssDNA | single-stranded DNA |

Acceptor fluorophore: Compounds which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher), than the maximum absorbance wavelength of the donor fluorophore, and have a fluorescence emission maximum at a wavelength ranging from about 400 to 900 nm. Acceptor fluorophores have an excitation spectrum which overlaps with the emission of the donor fluorophore, such that energy emitted by the donor can excite the acceptor. Ideally, an acceptor fluorophore is capable of being attached to the disclosed nanoprobes.

Exemplary acceptor fluorophores include, but are not limited to, rhodamine and its derivatives (such as N,N,N',N'-tetramethyl-6-carboxyrhodamine (TAMRA), 6-carboxy-X-rhodamine (ROX)), fluorescein derivatives (such as 5-carboxyfluorescein (FAM) and 2'7'-dimethoxy-4'5'-dichloro-6-carboxyfluorescein (JOE)), green fluorescent protein (GFP), BODIPY (4,4-difluoro-4-bora-3a,4a-diaza-s-indacene) and cyanine dyes. In particular examples, an acceptor fluorophore is capable of being attached to a nucleotide analog, such as the base, sugar, or phosphate ($\alpha$, $\beta$, or $\gamma$) of the nucleotide.

In a particular example, an acceptor fluorophore is a dark quencher, such as, Dabcyl, Black Hole Quenchers™ from Glen Research, Eclipse™ Dark Quencher from Epoch Biosciences, Iowa Black™ from Integrated DNA Technologies. In such an example, instead of detecting an increase in emission signal from the acceptor fluorophore when in sufficient proximity to the donor fluorophore, a decrease in the emission signal from the donor fluorophore can be detected when in sufficient proximity to the quencher.

Active site: The catalytic site of an enzyme or antibody, such as the region of a polymerase where the chemical reaction occurs. The active site includes one or more residues or atoms in a spatial arrangement that permits interaction with the substrate to effect the reaction of the latter.

Binding: An association between two or more molecules, such as the formation of a complex. Generally, the stronger the binding of the molecules in a complex, the slower their rate of dissociation. Specific binding refers to a preferential binding between an agent and a target.

Particular examples of specific binding include, but are not limited to, hybridization of one nucleic acid molecule to a complementary nucleic acid molecule, and the association of a protein (such as a polymerase) with a target protein or nucleic acid molecule.

In a particular example, a protein is known to bind to a nucleic acid molecule if a sufficient amount of the protein forms non-covalent chemical bonds to the nucleic acid molecule, for example a sufficient amount to permit detection of that binding.

In one example, an oligonucleotide molecule (such as an primer) is observed to bind to a target nucleic acid molecule if a sufficient amount of the oligonucleotide molecule forms base pairs or is hybridized to its target nucleic acid molecule to permit detection of that binding. The binding between an oligonucleotide and its target nucleic acid molecule is frequently characterized by the temperature ($T_m$) at which 50% of the oligonucleotide is melted from its target. A higher ($T_m$) means a stronger or more stable complex relative to a complex with a lower ($T_m$).

In a particular example, binding is assessed by detecting labels present on the nanoprobe. For example, the fluorescent signal generated following the interaction of donor and acceptor fluorophores can be measured as an indication of binding between a nucleotide analog on the nanoprobe and a complementary nucleotide in the target nucleic acid molecule.

Chemical moiety: A portion or functional group of a molecule. Examples include an agent, such as a nucleotide, that is capable of reversibly binding to the template strand of a target nucleic acid molecule by specifically binding with a complementary nucleotide in the target nucleic acid molecule. In particular examples, the chemical moiety is attached to a probe via a molecular linker, and does not detach from the linker when the chemical moiety specifically binds to a complementary nucleotide on the target nucleic acid molecule.

Particular examples of chemical moieties include, but are not limited to, nucleotide analogs that cannot be incorporated into a growing complementary nucleic acid strand, such as a non-hydrolyzable nucleotide analog.

cDNA (complementary DNA): A piece of DNA lacking internal, non-coding segments (introns) and regulatory sequences which determine transcription. cDNA is complementary to an mRNA and can be synthesized using reverse transcriptase.

Complementary: A double-stranded DNA or RNA strand consists of two complementary strands of base pairs. Since there is one complementary base for each base found in DNA/RNA (such as A/T, and C/G), the complementary strand for any single strand can be determined.

Detect: To determine if an agent is present or absent. In some examples this can further include quantification. For example, use of the disclosed probes in particular examples permits detection of a chemical moiety, for example as the chemical moiety binds to a complementary nucleotide in the target nucleic acid molecule without being detached from the linker.

Detection can be in bulk, so that a macroscopic number of molecules (such as at least $10^{23}$ molecules) can be observed simultaneously. Detection can also include identification of signals from single molecules using microscopy and such techniques as total internal reflection to reduce background noise. The spectra of individual molecules can be obtained by these techniques (Ha et al., *Proc. Natl. Acad. Sci. USA.* 93:6264-8, 1996).

Donor Fluorophore: Fluorophores or luminescent molecules capable of transferring energy to an acceptor fluorophore, thereby generating a detectable fluorescent signal. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$. A variety of compounds can be employed as donor fluorescent components, including fluorescein (and derivatives thereof), rhodamine (and derivatives thereof), GFP, phycoerythrin, BODIPY, DAPI (4',6-diamidino-2-phenylindole), Indo-1, coumarin, dansyl, terbium (and derivatives thereof), and cyanine dyes. In particular examples, a donor fluorophore is a chemiluminescent molecule, such as aequorin.

Electromagnetic radiation: A series of electromagnetic waves that are propagated by simultaneous periodic variations of electric and magnetic field intensity, and that includes radio waves, infrared, visible light, ultraviolet light, X-rays and gamma rays. In particular examples, electromagnetic radiation is emitted by a laser, which can possess properties of monochromaticity, directionality, coherence, polarization, and intensity. Lasers are capable of emitting light at a particular wavelength (or across a relatively narrow range of wavelengths), such that energy from the laser can excite a donor but not an acceptor fluorophore.

Emission signal: The light of a particular wavelength generated from a fluorophore after the fluorophore absorbs light at its excitation wavelengths.

Emission spectrum: The energy spectrum which results after a fluorophore is excited by a specific wavelength of light. Each fluorophore has a characteristic emission spectrum. In one example, individual fluorophores (or unique combinations of fluorophores) are associated with a nucleotide analog and the emission spectra from the fluorophores provide a means for distinguishing between the different nucleotide analogs.

Entangled: To be twisted together, for example in a tangled mass. In particular examples, entanglement of a nanoprobe would reduce or prevent the chemical moieties (such as nucleotide analogs) from interacting with the complementary nucleotide of a target nucleic acid molecule, in the presence of the target molecule. In other particular examples, entanglement of a nanoprobe results in an undesirable interaction between the chemical moieties (such as nucleotide analogs) or between the chemical moieties and the polymerizing agent, for example an interaction that prevents interaction with the target nucleic acid molecule.

Excitation or excitation signal: The light of a particular wavelength necessary to excite a fluorophore to a state such that the fluorophore will emit a different (such as a longer) wavelength of light.

Fluorophore: A chemical compound, which when excited by exposure to a particular stimulus such as a defined wavelength of light, emits light (fluoresces), for example at a different wavelength.

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules eliminates the need for an external source of electromagnetic radiation, such as a laser. Examples of chemiluminescent molecules include, but are not limited to, aequorin (Tsien, 1998, *Ann. Rev. Biochem.* 67:509).

Examples of particular fluorophores that can be used in the nanoprobes disclosed herein are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include thiol-reactive europium chelates which emit at approximately 617 nm (Heyduk and Heyduk, *Analyt. Biochem.* 248:216-27, 1997; *J. Biol. Chem.* 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. In one example, the fluorophore is a large Stokes shift protein (see Kogure et al., *Nat. Biotech.* 24:577-81, 2006). Other fluorophores known to those skilled in the art can also be used, for example those available from Molecular Probes (Eugene, Oreg.).

In particular examples, a fluorophore is used as a donor fluorophore or as an acceptor fluorophore. Ideally, fluorophores have the ability to be attached to a nanoprobe component without sufficiently interfering with the ability of the nanoprobe to interact with the target biomolecule, are stable against photobleaching, and have high quantum efficiency. In examples where multiple acceptor fluorophores are used, for example on a single nanoprobe or for example on different nanoprobes that are used together, the fluorophores are advantageously selected to have distinguishable emission spectra, such that emission from one fluorophore (or combination of two or more fluorophores) is distinguishable from another fluorophore (or combination of two or more fluorophores).

The fluorophores disclosed herein can be used as donor fluorophores or as acceptor fluorophores. Particularly useful fluorophores have the ability to be attached to a nanoprobe (for example to a polymerase, a molecular linker, or to a nucleotide analog), are stable against photobleaching, and have high quantum efficiency. In addition, the fluorophores associated with different sets of nucleotide analogs (such as those that correspond to A, T/U, G, and C) are advantageously selected to have distinguishable emission spectra, such that emission from one fluorophore (such as one associated with A) is distinguishable from the fluorophore associated with another nucleotide analog (such as one associated with T).

Förster (or fluorescence) resonance energy transfer (FRET): A process in which an excited fluorophore (the donor) transfers its excited state energy to a lower-energy light absorbing molecule (the acceptor). This energy transfer is non-radiative, and due primarily to a dipole-dipole interaction between the donor and acceptor fluorophores. This energy can be passed over a distance, for example a limited distance such as 10-100 Å. FRET efficiency drops off according to $1/(1+(R/R0)^6)$ where R0 is the distance at which the FRET efficiency is 50%.

FRET pairs: Sets (such as pairs) of fluorophores that can engage in fluorescence resonance energy transfer (FRET). Examples of FRET pairs that can be used are listed below. However, one skilled in the art will recognize that numerous other combinations of fluorophores can be used.

FAM is most efficiently excited by light with a wavelength of 488 nm, emits light with a spectrum of 500 to 650 nm, and has an emission maximum of 525 nm. FAM is a suitable donor fluorophore for use with JOE, TAMRA, and ROX (all of which have their excitation maxima at 514 nm, and will not be significantly stimulated by the light that stimulates FAM).

The GFP mutant H9-40 (Tsien, 1998, *Ann. Rev. Biochem.* 67:509), which is excited at 399 nm and emits at 511 nm, can serve as a suitable donor fluorophore for use with BODIPY, fluorescein, rhodamine green and Oregon green. In addition, the fluorophores tetramethylrhodamine, Lissamine™, Texas Red and naphthofluorescein can be used as acceptor fluorophores with this GFP mutant.

The fluorophore 3-(ε-carboxy-pentyl)-3'-ethyl-5,5'-dimethyloxacarbocyanine (CYA) is maximally excited at 488 nm and can therefore serve as a donor fluorophore for rhodamine derivatives (such as R6G, TAMRA, and ROX) which can be used as acceptor fluorophores (see Hung et al., *Analytical Biochemistry*, 243:15-27, 1996). However, CYA and FAM are not examples of a good FRET pair, because both are excited maximally at the same wavelength (488 nm).

One particular example of a FRET pair is GFP2 and YFP.

One of ordinary skill in the art can easily determine, using art-known techniques of spectrophotometry, which fluorophores will make suitable donor-acceptor FRET pairs. In addition, Grant et al. (*Biosens Bioelectron.* 16:231-7, 2001) provide particular examples of FRET pairs that can be used in the nanoprobes disclosed herein.

Fusion Protein: A protein that includes two amino acid sequences that are not found joined together in nature. The term "GFP-polymerase fusion protein" refers to a protein that includes a first amino acid sequence and a second amino acid sequence, wherein the first amino acid sequence is a GFP molecule (mutant or wild-type) and the second amino acid sequence is a polymerase. Similarly, the term "GFP-aequorin fusion protein" refers to a protein that includes a first amino acid sequence and a second amino acid sequence, wherein the first amino acid sequence is a GFP molecule (mutant or wild-type) and the second amino acid sequence is an aequorin. GFP-aequorin fusion proteins can be generated using the method of Baubet et al. (*Proc. Natl. Acad. Sci. USA* 97:7260-5, 2000, herein incorporated by reference).

These fusion proteins can be represented by the formula X-Y wherein X is a tag, such as GFP, and Y is a polymerizing agent, such as a polymerase. In some examples, an amino acid chain can be used to link the first and second domains of the fusion protein.

Green fluorescent protein (GFP): The source of fluorescent light emission in *Aequorea victoria*. As used herein, GFP refers to both the wild-type protein, and spectrally shifted mutants thereof, for example as described in Tsien, 1998, *Ann. Rev. Biochem.* 67:509 and in U.S. Pat. Nos. 5,777,079 and 5,625,048 to Tsien and Heim, herein incorporated by reference. In particular examples, GFP is excited using a laser. In other examples, GFP is excited using aequorin, for example using a GFP-aequorin fusion protein.

GFP-polymerase: Recombinant fusion protein containing both a functional GFP molecule and a functional polymerase. The GFP can be located at the N- or C-terminus of the polymerase, or anywhere within the polymerase, as long as the polymerase retains significant polymerizing activity (for example retaining the ability to catalyze the elongation of a complementary nucleic acid strand). GFP-polymerase can also include a linker (linker-GFP-polymerase), for example to aid in its purification or its attachment to a substrate. Furthermore, GFP-polymerase can also include a functional aequorin sequence, for example if the use of LRET is desired.

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the Na$^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

| Very High Stringency (detects sequences that share at least 90% identity) | |
|---|---|
| Hybridization: | 5x SSC at 65° C. for 16 hours |
| Wash twice: | 2x SSC at room temperature (RT) for 15 minutes each |
| Wash twice: | 0.5x SSC at 65° C. for 20 minutes each |

| High Stringency (detects sequences that share at least 80% identity) | |
|---|---|
| Hybridization: | 5x-6x SSC at 65° C.-70° C. for 16-20 hours |
| Wash twice: | 2x SSC at RT for 5-20 minutes each |
| Wash twice: | 1x SSC at 55° C.-70° C. for 30 minutes each |

| Low Stringency (detects sequences that share at least 50% identity) | |
|---|---|
| Hybridization: | 6x SSC at RT to 55° C. for 16-20 hours |
| Wash at least twice: | 2x-3x SSC at RT to 55° C. for 20-30 minutes each. |

20×SSC is 3.0 M NaCl/0.3 M trisodium citrate.

Linker: A structure that joins one molecule to another, such as attaches a probe of the present disclosure to a substrate, wherein one portion of the linker is operably linked to a substrate, and wherein another portion of the linker is operably linked to the probe.

One particular type of linker is a molecular linker, such as tethers, rods, or combinations thereof, which can attach a polymerizing agent to one or more chemical moieties (such as one or more nucleotide analogs) wherein one portion of the linker is operably linked to the polymerizing agent, and wherein another portion of the linker is operably linked to one or more chemical moieties.

Locked Nucleic Acid (LNA™): A bicyclic nucleic acid where a ribonucleoside is linked between the 2'-oxygen and the 4'-carbon atoms with a methylene unit. This link restricts the flexibility of the ribofuranose ring of the nucleotide analog and locks it into the rigid bicyclic N-type conformation. The LNA also induces adjacent bases to adopt a conformation of the more thermodynamically stable form of the A duplex.

LNA oligonucleotides can be synthesized by standard phosphoramidite chemistry using DNA-synthesizers. In addition, LNA can be mixed with DNA, RNA as well as other nucleic acid analogs. In particular examples, LNAs are included as part of a molecular linker.

Luminescence Resonance Energy Transfer (LRET): A process similar to FRET, in which the donor molecule is a luminescent molecule, or is excited by a luminescent molecule, instead of for example by a laser. Using LRET can decrease the background fluorescence. In particular examples, a chemiluminescent molecule can be used to excite a donor fluorophore (such as GFP), without the need for an external source of electromagnetic radiation. In other examples, the luminescent molecule is the donor, wherein the excited resonance of the luminescent molecule excites one or more acceptor fluorophores.

Examples of luminescent molecules that can be used include, but are not limited to, aequorin and luciferase. The bioluminescence from aequorin, which peaks at 470 nm, can be used to excite a donor GFP fluorophore (Tsien, 1998, *Ann. Rev. Biochem.* 67:509; Baubet et al., 2000, *Proc. Natl. Acad. Sci. U.S.A.*, 97:7260-5). GFP then excites an acceptor fluorophore disclosed herein. In this example, both aequorin and GFP can be attached to a nanoprobe of the present disclosure. The bioluminescence from *Photinus pyralis* luciferase, which peaks at 555 nm, can excite an acceptor fluorophore disclosed herein. In this example, both luciferase and GFP can be attached to a nanoprobe of the present disclosure. In some examples where luciferase is used, the dipole of the acceptor fluorophore is aligned with the polarization of the luciferase light. In other examples, a large number of luciferase molecules are aligned next to or even surrounding the nanoprobe. For example, a sphere, a dendrimer or a sheet could be made that has many molecules of luciferase inside or on the surface.

Nanoprobe or probe: A molecular device that can be used to sequence a nucleic acid molecule. In particular examples, a nanoprobe or probe includes one or more tags that permit detection of the sequence, such as an acceptor and donor fluorophore pair.

Nucleic acid molecule (or sequence): A deoxyribonucleotide or ribonucleotide polymer including without limitation, cDNA, mRNA, genomic DNA, and synthetic (such as chemically synthesized) DNA or RNA. The nucleic acid molecule can be double stranded (ds) or single stranded (ss). Where single stranded, the nucleic acid molecule can be the sense strand or the antisense strand. Nucleic acid molecules can include natural nucleotides (such as A, T/U, C, and G), and can also include analogs of natural nucleotides. A set of bases linked to a peptide backbone, as in a peptide nucleic acid (PNA), can be used as a substitute for a nucleic acid molecule.

A target nucleic acid molecule is a nucleic acid to be sequenced, and can be obtained in purified form, by any method known to those skilled in the art (for example, as described in U.S. Pat. No. 5,674,743 to Ulmer). A complementary nucleic acid molecule is complementary to the target nucleic acid molecule and is the nucleic acid strand that is elongated when sequencing the target nucleic acid molecule.

Nucleotide: A monomer that includes a base, such as a pyrimidine, purine, or synthetic analogs thereof, linked to a sugar and one or more phosphate groups. A nucleotide is one monomer in a polynucleotide. A nucleotide sequence refers to the sequence of bases in a polynucleotide.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

The choice of nucleotide precursors is dependent on the nucleic acid to be sequenced. If the template is a single-stranded DNA molecule, deoxyribonucleotide precursors (dNTPs) are used in the presence of a DNA-directed DNA polymerase. Alternatively, ribonucleotide precursors (NTPs) are used in the presence of a DNA-directed RNA polymerase. However, if the nucleic acid to be sequenced is RNA, then dNTPs and an RNA-directed DNA polymerase are used.

The nucleotides disclosed herein also include nucleotides containing modified bases, modified sugar moieties and modified phosphate backbones, for example as described in U.S. Pat. No. 5,866,336 to Nazarenko et al. (herein incorporated by reference). Such modifications however, can allow for incorporation of the nucleotide into a growing nucleic acid chain or for binding of the nucleotide to the complementary nucleic acid chain. Modifications described herein do not result in the termination of nucleic acid synthesis.

Nucleotides can be modified at any position on their structures. Examples include, but are not limited to, the modified nucleotides 5-fluorouracil, 5-bromouracil, 5-chlorouracil, 5-iodouracil, hypoxanthine, xanthine, acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl)uracil, and 2,6-diaminopurine.

Examples of modified sugar moieties which can be used to modify nucleotides at any position on their structures include, but are not limited to: arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Nucleotide analog: A nucleotide containing one or more modifications of the naturally occurring base, sugar, phosphate backbone, or combinations thereof. Such modifications can result in the inability of the nucleotide to be incorporated into a growing nucleic acid chain. A particular example includes anon-hydrolyzable nucleotide. Non-hydrolyzable nucleotides include mononucleotides and trinucleotides in which the oxygen between the alpha and beta phosphates has been replaced with nitrogen or carbon (Jena Bioscience). HIV-1 reverse transcriptase cannot hydrolyze dTTP with the oxygen between the alpha and beta phosphates replaced by nitrogen (Ma et al., *J. Med. Chem.*, 35: 1938-41, 1992).

A "type" of nucleotide analog refers to one of a set of nucleotide analogs that share a common characteristic that is to be detected. For example, the sets of nucleotide analogs can be divided into four types: A, T, C and G analogs (for DNA) or A, U, C and G analogs (for RNA). In this example, each type of nucleotide analog can be associated with a unique tag, such as one or more acceptor fluorophores, so as to be distinguishable from the other nucleotide analogs in the set (for example by fluorescent spectroscopy or by other optical means).

An exemplary nucleotide analog that can be used in place of "C" is a G-clamp (Glen Research). G-clamp is a tricyclic Aminoethyl-Phenoxazine 2'-deoxycytidine analogue (AP-dC). The G-clamp is available as a phosphoramidite and so can be synthesized into DNA structures. Such an analog can be used in the nanoprobes provided herein (for example as one of the chemical moieties 22, 24, 26, 28 of the probe shown in FIG. 1A or it can be substituted for the dCTP 22 shown in FIG. 1B).

Oligonucleotide: A linear polynucleotide (such as DNA or RNA) sequence of at least 6 nucleotides, for example at least 9, at least 15, at least 18, at least 24, at least 30, at least 50, at least 100, at least 200 or even at least 500 nucleotides long. An oligonucleotide can contain non-naturally occurring portions, such as altered sugar moieties or inter-sugar linkages, such as a phosphorothioate oligodeoxynucleotide. In particular examples, an oligonucleotide containing non-naturally occurring portions can bind to RNA or DNA, and include peptide nucleic acid (PNA) molecules.

ORF (open reading frame): A series of nucleotide triplets (codons) coding for amino acids without any termination codons. These sequences are usually translatable into a peptide.

Pairing: The process of joining into a pair, such as the binding of a chemical entity (such as a nucleotide analog) to its complementary nucleotide on a target nucleic acid molecule. In particular examples, pairing results in the formation of covalent bonds. In other examples, pairing does not result in the formation of chemical bonds.

Peptide Nucleic Acid (PNA): A class of informational molecules containing a neutral peptide-like backbone with nucleobases allowing it to hybridize to complementary RNA or DNA with higher affinity and specificity than conventional oligonucleotides. The structure of a PNA molecule is analogous with DNA, wherein the deoxyribose phosphate backbone has been replaced by a backbone similar to that found in peptides. In particular examples, PNA is resistant to nucleases and proteases. PNAs can include a functional group at the N(5)-terminus, such as a fluorophore (for example an acceptor fluorophore).

Persistence length (lp): The average local conformation for a linear chain, reflecting the sum of the average projections of all chain segments on a direction described by a given segment. In particular examples, persistence length is the degree of bending (and hence the effective stiffness of the chain) which, in effect, measures the contour distance over which there occurs, on the average, a 68.40° bend.

Polyethylene glycol (PEG): A polymer of ethylene compounds, $H(OCH_2CH_2)_nOH$. Pegylation is the act of adding a PEG structure to another molecule, for example, a functional molecule such as a targeting or activatable moiety. PEG is soluble in water, methanol, benzene, dichloromethane and is insoluble in diethyl ether and hexane.

Particular examples of PEG that can be used in the disclosed nanoprobes include, but are not limited to: 1-7 units of Spacer 18 (Integrated DNA Technologies, Coralville, Iowa), such as 3-5 units of Spacer 18, C3 Spacer phosphoramidite (such as 1-10 units), Spacer 9 (such as 1-10 units), PC (Photo-Cleavable) Spacer (such as 1-10 units), (all available from Integrated DNA Technologies). In other examples, lengths of PEG that can be used in the disclosed nanoprobes include, but are not limited to, 1 to 40 monomers of PEG.

Polymerizing agent: A compound capable of reacting monomer molecules (such as nucleotides) together in a chemical reaction to form linear chains or a three-dimensional network of polymer chains. A particular example of a polymerizing agent is polymerase, an enzyme which synthesizes a nucleic acid strand complementary to a nucleic acid template. Examples of polymerases that can be used to sequence a nucleic acid molecule include, but are not limited to the E. coli DNA polymerase I, specifically the Klenow fragment which has 3' to 5' exonuclease activity, Taq polymerase, reverse transcriptase (such as HIV-1 RT or reverse transcriptase of the L1 retrotransposon), E. coli RNA polymerase, and wheat germ RNA polymerase II.

The choice of polymerase is dependent on the nucleic acid to be sequenced. If the template is a single-stranded DNA molecule, a DNA-directed DNA or RNA polymerase can be used; if the template is a single-stranded RNA molecule, then a reverse transcriptase (such as an RNA-directed DNA polymerase) can be used.

Primer: Short nucleic acid molecules, for example sequences of at least 9 nucleotides, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, individual primers can be used for nucleic acid sequencing, wherein the sequence of the primer is specific for the target nucleic acid molecule, for example so that the primer will hybridize to the target nucleic acid molecule under stringent hybridization conditions.

In particular examples, a primer is at least 10 nucleotides in length, such as at least contiguous nucleotides complementary to a target nucleic acid molecule to be sequenced. In order to enhance specificity, longer primers can be employed, such as primers having at least 12, at least 15, at least 20, or at least 30 contiguous nucleotides complementary to a target nucleic acid molecule to be sequenced. Methods for preparing and using primers are described in, for example, Sambrook et al. (1989) *Molecular Cloning: A Laboratory Manual*, Cold Spring Harbor, N.Y.; Ausubel et al. (1987) *Current Protocols in Molecular Biology*, Greene Publ. Assoc. & Wiley-Intersciences.

Purified: The term purified does not imply absolute purity; rather, it is intended as a relative term. Thus, for example, a purified GFP-polymerase protein preparation is one in which the GFP-polymerase protein is more pure than the protein in its environment within a cell. In particular examples, a preparation of a GFP-polymerase protein is purified such that the GFP-polymerase protein represents at least 50% of the total protein content of the preparation, but can be, for example 90 or even 98% of the total protein content.

Quantum dots: Engineered, inorganic semiconductor crystalline nanoparticles that fluoresce stably and possess a uniform surface area that can be chemically modified to attach biomolecules (such as one or more nanoprobes) to them. Although generally spherical, quantum dots attached to nanoprobes of the present disclosure can be of any shape (such a spherical, tubular, pyramidal, conical or cubical), but particularly suitable nanoparticles are spherical.

Generally, quantum dots can be prepared with relative monodispersity (for example, with the diameter of the core varying approximately less than 10% between quantum dots in the preparation), as has been described previously (Bawendi et al., *J. Am. Chem. Soc.* 115:8706, 1993). Quantum dots known in the art have, for example, a core selected from the group consisting of CdSe, CdS, and CdTe (collectively referred to as "CdX").

Recombinant: A recombinant nucleic acid molecule or protein sequence is one that has a sequence that is not naturally occurring or has a sequence that is made by an artificial combination of two otherwise separated segments of sequence. In particular examples, this artificial combination is accomplished by chemical synthesis or by the artificial manipulation of isolated segments of nucleic acid or protein sequences, for example by genetic engineering techniques. In particular examples, a molecular rod composed of a dsDNA is a recombinant molecule.

Reverse Transcriptase: A template-directed DNA polymerase that generally uses RNA but can use DNA as its template.

Reversibly binding to a target nucleic acid molecule: Temporary binding that exists in a reversible equilibrium. For example, includes transient pairing of a nucleotide to its complement at the active site of a polymerase, wherein the nucleotide does not undergo a chemical reaction (such as hydrolysis or covalent bond formation) that covalently incorporates the nucleotide into the nucleic acid molecule being formed by the polymerase.

RNA polymerase: An enzyme that catalyzes the polymerization of ribonucleotide precursors that are complementary to the DNA template.

Rod or molecular rod: A structure that can be included in a nanoprobe's molecular linker to increase the rigidity of a portion of the nanoprobe, such as a portion of the molecular linker. Molecular rods are sufficiently rigid to reduce the interaction of chemical moieties, polymerizing agents, or combinations thereof, in the absence of the target nucleic acid molecule. In addition, molecular rods are of a length that permits the chemical moieties, polymerizing agents, or combinations thereof to interact in the presence of the target biomolecule.

In a particular example, a molecular rod present in a molecular linker has a length shorter than its persistence length, thereby significantly reducing the interaction of the chemical moieties, polymerizing agents, or combinations thereof in the absence of the target biomolecule. In one example, a molecular rod consisting of dsDNA has a length of 10-140 nucleotides, which is shorter than the persistence length of dsDNA, about 150 nucleotides.

Exemplary molecular rods include, but are not limited to, dsDNA molecules, peptide nucleic acids (PNAs), carbon nanotubes, locked nucleic acid molecules (LNAs), a microtubule, a bacterium, a linear virus particle, virus tail fibers or other protein structures (such as protein components containing alpha helices or beta barrels or other protein structures, such as a leucine zipper structure). A molecular rod can be a portion of a three-dimensional molecular construct, such as a cube or octahedron built from DNA (for example see Seeman, *Sci. Am.* 290:64-9 and 72-5, 2004). In a particular example, a molecular rod is a dsDNA molecule of at least 10 nucleotides, at least 35 nucleotides, or 150 nucleotides or less, such as 10-150 nucleotides, 10-140 nucleotides, 20-100 nucleotides, 20-50 nucleotides, 20-40 nucleotides, 30-50 nucleotides, or about 20, 30, or 40 nucleotides.

Sample: Biological specimens such as samples containing biomolecules, such as nucleic acid molecules (for example genomic DNA, cDNA, RNA, or mRNA). Exemplary samples are those containing cells or cell lysates from a subject, such as those present in peripheral blood (or a fraction thereof such as serum), urine, saliva, tissue biopsy, cheek swabs, surgical specimen, fine needle aspirates, amniocentesis samples and autopsy material.

Sequence of signals: The sequential series of emission signals, including electromagnetic signals such as light or spectral signals, which are emitted upon specific binding of chemical moieties (such as a nucleotide analog) with complementary nucleotides in the target nucleic acid molecule, which indicates pairing of the chemical moiety with its complementary nucleotide. In a particular example, the sequence of signals are a series of acceptor fluorophore emission signals, wherein each unique signal is associated with a particular chemical moiety.

Signal: A detectable change or impulse in a physical property that provides information. In the context of the disclosed methods, examples include electromagnetic signals such as light, for example light of a particular quantity or wavelength. In certain examples the signal is the disappearance of a physical event, such as quenching of light. A characteristic signal is the particular signal expected when a particular nucleotide analog on the nanoprobe specifically binds with a complementary nucleotide in the target nucleic acid molecule. For example, a characteristic signal can be the resulting signal emitted from a fluorescently tagged non-hydrolyzable nucleotide analog, which can be predicted by the fluorophore(s) attached to or associated with the nucleotide analog.

Subject: Living multi-cellular vertebrate organisms, including human and veterinary subjects, such as cows, pigs, horses, dogs, cats, birds, reptiles, and fish.

Substrate: A material or surface to which other molecules (such as proteins or nucleic acid molecules) can be attached or embedded within. In particular examples, the substrate is made of biocompatible material that is transparent to light, including glass and quartz. For example, the substrate can be a 3 cm long by 1 cm wide by 0.25 cm thick glass microscope slide. In yet another example, for example when LRET is used, the substrate can be opaque. In one example, the substrate is a gel matrix. In a specific example, the substrate is a microfluidic device having a parabolic flow channel profile.

In particular examples, a substrate is treated before attaching other molecules. For example, glass microscope slides can be washed by ultrasonication in water for 30 minutes, soaked in 10% NaOH for 30 minutes, rinsed with distilled water and dried at 80° C. for 10 minutes or air-dried overnight.

Tag: An agent capable of being detected, for example by spectrophotometry, flow cytometry, or microscopy. For example, one or more tags can be attached to a nanoprobe, thereby permitting sequencing of a nucleic acid molecule. Exemplary tags include radioactive isotopes, fluorophores, chemiluminescent agents, charges, enzymes, and combinations thereof.

Tether: A structure that can be included in a nanoprobe to link one or more chemical entities (such as a nucleotide analog) to a polymerizing agent, directly or indirectly. For example, one or more tethers, in combination with one or more molecular rods, can be used to link one or more chemical entities (such as a nucleotide analog) to a polymerizing agent. Ideally, the tether is a length that reduces the likelihood that the tether will tangle with itself or with other components of the nanoprobe, while still allowing the chemical entities (such as a nucleotide analog), polymerizing agent, tags, or combinations thereof to interact in the presence of the target nucleic acid molecule.

Exemplary tethers include water soluble long chain molecules, such as PEG, peptides (such as a peptide of at least 30 amino acids, for example at least 30 contiguous amino acids of the RecB protein 70-amino acid-long flexible tether connecting the helicase to the nuclease (Singleton et al., *Nature* 432:187-93, 2004)), sugar chains (such as 2000-14000 residues), a basic phosphodiester spacers (such as the IDT 5' dSpacer), carbohydrate chains (such as at least 10 sugar molecules), and polycaprolactone chains (such as at least 10 monomers). In a particular example, a tether is composed of PEG, for example a PEG length of about 23-164 Å.

Target nucleic acid sequence or molecule: A pre-selected nucleic acid molecule, for example whose detection or sequence is desired. The nucleic acid molecule need not be in a purified form. Various other biomolecules can also be present with the target nucleic acid molecule. For example, the target nucleic acid molecule can be present in a cell or a biological sample (which can include other nucleic acid molecules and proteins).

Transformed: A transformed cell is a cell into which has been introduced a nucleic acid molecule by molecular biology techniques. As used herein, the term transformation encompasses all techniques by which a nucleic acid molecule can be introduced into such a cell, including transfection with viral vectors, transformation with plasmid vectors, and introduction of naked DNA by electroporation, lipofection, injection, and particle gun acceleration. In particular examples, a cell is transformed with a probe disclosed herein.

Under conditions sufficient for: A phrase that is used to describe any environment that permits the desired activity.

An example includes contacting a probe with a sample under conditions sufficient to allow sequencing of a target nucleic acid molecule in the sample, for example to determine whether the target nucleic acid molecule is present in the sample, such as a target nucleic acid molecule containing one or more mutations.

Unique Emission Signal: An emission signal that conveys information about a specific event, such as the emission spectrum for a particular fluorophore, which can be distinguished from other signals (such as other emission spectrum signals). Examples in association with the disclosed methods include associating one or more individual fluorophores or other tags with each type of chemical moiety (such as an A, T/U, C or G non-hydrolyzable nucleotide analog), such that pairing of the chemical moiety with its complementary base on the target nucleic acid molecule results in a unique signal or a combination of signals (such as fluorophores that emit at different unique wavelengths).

Each chemical moiety will have a unique emission signal that in the examples is based on the tag(s) associated with that chemical moiety. This signal can be used to determine which type of chemical moiety (such as an A, T/U, C or G nonhydrolyzable nucleotide analog) has been paired with the complementary nucleotide in the target nucleic acid, and these signals in combination indicate the nucleic acid sequence.

A signal can be characterized not only by different wavelengths but also by different intensities at various wavelengths, to form a unique spectrum. In particular, two signals having the same set of wavelengths can be distinguished if they have some different intensities at particular wavelengths.

General Strategy

The disclosed nanoprobes that can be used to sequence a target nucleic acid molecule include a polymerizing agent and one or more molecular linkers that space one or more chemical moieties that are capable of binding to a complementary nucleotide in a target nucleic acid molecule. The chemical moieties are generally not capable of being permanently incorporated into the elongating nucleic acid molecule. The linker has a combination of length and flexibility that substantially maintains the polymerizing agent and chemical moieties spaced a desired distance in the absence of the target nucleic acid molecule, but permits them to substantially interact in the presence of the target biomolecule. In addition, the molecular linker(s) substantially avoid entanglement of the molecular linkers with one another, and substantially avoid entanglement of the chemical moieties at the ends of the linkers. Table 1 illustrates some combinations of polymerizing agents and chemical moieties that can be used. Also provided are exemplary tags that can be associated with the polymerizing agent and chemical moieties.

flexibility of the molecular linker is sufficient to permit the polymerizing agent and the chemical moieties to interact (for example interaction of a nonhydrolyzable nucleotide analog with the active site of a polymerase).

Nanoprobes for Sequencing a Nucleic Acid Molecule

The present disclosure provides nanoprobes for sequencing target nucleic acid molecules. In particular examples, the disclosed nanoprobes are used in vitro, ex vivo, in situ, or even in vivo. The probes, referred to as "Medusa" probes, include a polymerizing agent and one or more molecular linkers spaced apart on the polymerizing agent, wherein the linkers carry a chemical moiety that is capable of reversibly binding to the template strand of a nucleic acid molecule, without being detached from the linker, by specifically binding with a complementary nucleotide in the target nucleic acid molecule. The reversible incorporation of the chemical moiety on the linker with a complementary nucleotide in the target nucleic acid molecule is indicated by emission of a characteristic signal (such as a decrease in donor fluorophore emission or an increase in acceptor fluorophore emission) that indicates pairing of the chemical moiety on the linker with its complementary nucleotide in the target nucleic acid molecule.

The polymerizing agent, such as a polymerase, includes an active site capable of binding to a target nucleic acid molecule and promoting synthesis of a complementary nucleic acid molecule that elongates as complementary nucleotides are incorporated into the complementary nucleic acid molecule. In particular examples, the complementary nucleotides are hydrolyzable nucleotides that are capable of being permanently incorporated into the elongating nucleic acid molecule that is complementary to the target nucleic acid molecule. For example, this is in contrast to a chemical moiety (such as a nonhydrolyzable nucleotide analog, for example a nonhydrolyzable dNTP) which may reversibly bind to the target

TABLE 1

Exemplary polymerizing agent/chemical moiety/tag combinations.

| Target | Polymerizing Agent/Tag | Chemical Moieties/Tag |
| --- | --- | --- |
| DNA | DNA polymerase/donor fluorophore | Nonhydrolyzable dNTPs/acceptor fluorophores |
| DNA | Klenow/donor fluorophore | Mononucleotides/acceptor fluorophores |
| DNA | HIV-1-reverse transcriptase/fluorescein | dGMPCPP/Cy3 dAMPCPP/Cy5 dCMPCPP/Texas Red TMPCPP/Rhodamine Red |
| RNA | RNA polymerase/donor fluorophore | Nonhydrolyzable dNTPs/acceptor fluorophores |
| RNA | reverse transcriptase/donor fluorophore | Mononucleotides/acceptor fluorophores |

The probes need only to maintain potential interactions of the polymerizing agent and the chemical moieties outside of a minimum distance. Also, since the location of the molecular components can only be expressed in terms of statistical probabilities, it is understood that absences of interaction are not absolute but instead refer to restriction of dynamic molecular movements in a manner that reduces undesired interactions between the polymerizing agent and the chemical moieties (and between the chemical moieties themselves) to a desired level. Once the polymerizing agent binds to a target nucleic acid molecule in the presence of a primer, the nucleic acid molecule (for example by forming hydrogen bonds with a complementary nucleotide), but cannot be permanently incorporated into the elongating complementary nucleic acid molecule.

The chemical moiety that is capable of reversibly binding to the template strand of a nucleic acid molecule, without being detached from the linker, is one that does not become permanently incorporated into the elongating nucleic acid molecule that is complementary to the target nucleic acid molecule. For example, the chemical moiety may form one or more non-covalent chemical bonds (such as hydrogen binding) with the template strand of the target nucleic acid molecule, but such bonds exist in reversible equilibrium at a rate that permits replacement of the chemical moiety by a nucleotide that permits elongation of the complementary strand, such as a hydrolyzable nucleotide (such as ATP, GTP, CTP, UTP, dATP, dGTP, dCTP, dTTP) that is covalently incorporated into the elongating strand. The chemical moieties can specifically and reversibly bind with a complementary nucleotide in the target nucleic acid molecule to bring an acceptor label associated with the chemical moiety into sufficient proximity with a donor label to stimulate the acceptor label. Such pairing can result in the emission of a signal that is characteristic for the particular chemical moiety that paired. For example, all of the different chemical moieties may initially bind to the active site of a polymerizing agent at the same rate, since this binding will be related to the diffusion of the chemical moieties. However, since the kinetics of release of the different chemical moieties are related to the number and strength of the bonds formed, the chemical moiety that is complementary to the exposed nucleotide in the target strand will bind stronger and will stay bound in the active site longer than the other chemical moieties. This increased binding time permits generation and detection of the signal that is characteristic for the particular chemical moiety that paired.

A particular example of such a chemical moiety is a nucleotide analog, for example a nonhydrolyzable nucleotide analog. The chemical moiety can be attached to the molecular linker by any means that does not substantially interfere with the ability of the chemical moiety to interact with the active site of the polymerizing agent, to pair with a complementary nucleotide in the target nucleic acid strand, and the ability to reversibly non-covalently bind (usually by stacking) to the elongating nucleic acid molecule. For example, if the chemical moiety is a nucleotide analog, it can be attached to the molecular linker via the base, sugar, or phosphate. In a particular example, if the chemical moiety is a mononucleotide, it can be attached to the molecular linker on the base or the 3' ribose carbon.

In particular examples, the molecular linkers used to attach chemical moieties to the polymerizing agent include a plurality of individual linkers attached at multiple points to the polymerizing agent. For example, at least four independent molecular linkers, each of which carries a different type of chemical moiety capable of specifically binding with a different nucleotide in the target nucleic acid molecule, can be attached to the polymerizing agent. In a specific example, at least eight independent molecular linkers, each of which carries a different fluorophore or combination of fluorophores associated with a particular chemical moiety capable of specifically binding with a different nucleotide in the target nucleic acid molecule, can be attached to the polymerizing agent. For example two of the eight linkers can include a dCTP, wherein each dCTP is associated with a different acceptor fluorophore or combination of fluorophores such that each dCTP produces a distinct detectable signal. This allows runs of bases, G in this case, to be more easily distinguished. However, in other examples, the molecular linkers are attached at one point to the polymerizing agent, for example through a single covalent bond that allows free rotation, thereby allowing the chemical moieties on the ends of the linkers to have equal access to the polymerizing agent active site. For example, the molecular linkers can be joined and attached to the polymerizing agent in one location. In a particular example, the molecular linkers are joined and attached to another agent (such as a linker), which is then attached to the polymerizing agent. The molecular linkers used to attach chemical moieties to the polymerizing agent can include a plurality of molecular linkers that form a branched structure, which is attached to the polymerizing agent. For example, each branch can carry a different chemical moiety capable of specifically binding with a different nucleotide in the target nucleic acid molecule. In a specific example, the branch structure includes at least four branches, wherein each branch carries a different chemical moiety. In some examples, the branched molecular linker attaches at a single point to the polymerizing agent.

In particular examples, the polymerizing agent is associated with a tag, and each of the chemical moieties is associated with a tag that identifies a particular chemical moiety carried by the linker, wherein interaction of the tag associated with the polymerizing agent with the tag associated with the chemical moiety induces emission of the characteristic signal that indicates pairing of the chemical moiety on the linker with its complementary nucleotide. Association of the tag with a component of the probe can include direct attachment of the tag with the component. For example, the polymerizing agent can be a GFP-polymerase fusion protein. Similarly, if the chemical moiety is a nucleotide analog, the tag can be attached to the base, sugar, or a phosphate of the nucleotide analog. Ideally, direct or indirect attachment of a tag to a polymerizing agent or a chemical moiety of the probe does not significantly inhibit the biological activity of that component. For example, attachment of a tag to a polymerizing agent ideally does not decrease the polymerase activity by more than 20%. In other examples, association of the tag with a polymerizing agent or a chemical moiety does not require direct attachment of the tag with the component. For example, the tag can be on another part of the probe, such as a molecular linker (for example on a tether or on a rod). In such examples, the tag is in sufficient proximity to the polymerizing agent or the chemical moiety to permit detection of the chemical moiety in the active site of the polymerizing agent, and the pairing of the chemical moiety with its complementary nucleotide.

In particular examples, the tag associated with the polymerizing agent forms a donor-acceptor pair with the tag associated with each chemical moiety, whereby interaction of the donor-acceptor pair stimulates emission of the characteristic signal. In some examples, the donor is stimulated by application of an external stimulus (such as a laser or chemiluminescent molecule) to emit a stimulus to which the acceptor reacts to emit the characteristic signal. For example, the tag associated with the polymerizing agent can be a donor fluorophore, and each of the tags associated with the chemical moiety includes one or more acceptor fluorophores that emits a unique emission signal for a particular chemical moiety.

In particular examples, the molecular linkers include linear polymers, such as nucleotides. For example, the molecular linker can include a tether, a rod, or combinations thereof. The molecular linkers can be spaced around the polymerizing agent a sufficient distance to inhibit entanglement of the linkers, and be of sufficient length for the chemical moiety to reach the active site of the polymerizing agent. In addition, the molecular linker can maintain the polymerizing agent and the chemical moiety sufficiently spaced a distance from one another to avoid substantial entanglement of the polymerizing agent and the chemical moiety in an absence of the target nucleic acid strand. In some examples, at least a portion of the molecular linker (a rod) is of a sufficient rigidity to reduce interaction of the polymerizing agent and the chemical moiety in the absence of the target nucleic acid molecule, such as a molecular rod having a length at least as great as its persistence length, for example a dsDNA rod having a length at 10-150 nucleotides. In a particular example, the molecular rod is a dsDNA sequence of 10 to 140 nucleotides, such as 20-100 nucleotides, for example 40 nucleotides. In a specific example the molecular rod is 120 angstroms (Å) long.

For example, to increase the rigidity of the molecular linker, the molecular linker can include one or more molecular rods, such as at least two tethers linked by a molecular rod. The inclusion of a molecular rod, such as a double-stranded DNA molecule, can be included to increase the rigidity of the probe, and can also further separate the functional groups. For example, a molecular linker that includes a molecular rod with tethers on both ends can have at least two points about which the chemical moieties and polymerizing agent will move by Brownian motion. That is, there will be at least two cloud spheres each of which represents all the possible locations of a chemical moiety with respect to the end of a rod as allowed by tethers. These spheres will intersect to some degree. In the absence of a target nucleic acid molecule, the nanoprobe can have the spheres not substantially intersecting. In some examples, the distance between the two ends of the molecular rod is less than the sum of the two tether lengths. In particular examples, the molecular rod is used to decrease FRET between the donor and acceptor fluorophores on the nanoprobe in the absence of the target nucleic acid molecule.

The polymerizing agents disclosed herein include an active site capable of binding to a target nucleic acid molecule and promoting synthesis of a complementary nucleic acid molecule that elongates as complementary nucleotides are incorporated into the complementary nucleic acid molecule. The polymerizing agent also includes one or more molecular linkers spaced apart on the polymerizing agent a sufficient distance to significantly avoid entanglement. Each linker carries a different chemical moiety (such as a nonhydrolyzable nucleotide analog) that is capable of reversibly binding to the template strand of a nucleic acid molecule, without being detached from the linker, by specifically binding with a complementary nucleotide in the target nucleic acid molecule. The polymerizing agent can further include a tag, for example a tag associated with the polymerizing agent, and a tag associated with each chemical moiety that identifies the chemical moiety carried by the linker. The tag associated with the polymerase can interact with each tag associated with the chemical moieties to emit a characteristic signal that identifies the chemical moiety carried by the linker.

As noted above, in particular examples the length of the molecular linker is one that maintains the polymerizing agent and the chemical moieties sufficiently spaced from one another such that the polymerizing agent (for example a tag associated with the polymerizing agent) and the chemical moieties do not substantially interact in an absence of the target biomolecule. Methods are known in the art for determining whether one part of the probe interacts with one or more other parts of the probe, for example in the presence or absence of a target molecule. In one example, to determine if a particular length molecular linker is appropriate, a probe of the present disclosure having a particular molecular linker length is generated using the methods disclosed herein. In particular examples, multiple probes are generated, each having a different molecular linker length. To identify lengths of molecular linkers that are suitable for use, a donor fluorophore is attached to the polymerizing agent at one end of the molecular linker and an appropriate acceptor fluorophore is attached to the chemical moiety at the other end of the molecular linker. In particular examples, the donor and acceptor are a FRET pair. To determine if the ends of the molecular linkers are capable of interacting with one another, the molecular linker can be placed in a solution in the presence and absence of the target nucleic acid molecule and an appropriate primer, and acceptor emission fluorescence detected, for example by spectrophotometry or fluorescence microscopy. In particular examples, lengths of molecular linkers that only produce significant acceptor emission fluorescence (for example above a predetermined threshold) when the target nucleic acid molecule and the primer are present, and produce no more than background levels of acceptor emission fluorescence in the absence of the target nucleic acid molecule and the primer, can be used in the probes of the present disclosure. In contrast, in particular examples, lengths of molecular linkers that do not produce significant acceptor emission fluorescence when the target nucleic acid molecule and the primer is present, or produce levels of acceptor emission fluorescence that are significantly above background in the absence of the target nucleic acid molecule and the primer, are not used in the probes of the present disclosure. In some examples, the length of the molecular linker that produces a desirable result can vary depending on the particular FRET pair used. For example, the length of the molecular linker used if a GFP/fluorescein FRET pair is part of the probe, may be different than the length of the molecular linker used if an Alexa Fluor 430/BODIPY 630 FRET pair is part of the probe.

To reduce interaction of the polymerizing agent and the chemical moieties in the absence of the target nucleic acid molecule, the molecular linker (or a portion thereof) can have a persistence length that permits the molecular linker to be of sufficient rigidity to reduce the interaction of the polymerizing agent (such as a tag associated with the polymerizing agent) and the chemical moieties in the absence of the target nucleic acid molecule (as well as interaction between the chemical moieties themselves in the presence or absence of the target nucleic acid molecule). Other portions of the molecular linker, such as tethers, allow interaction of the polymerizing agent (such as its tag) and the chemical moieties (or interaction of polymerizing agent and the chemical moieties with the target nucleic acid molecule) in the presence of the target nucleic acid molecule.

The total length of the molecular linker can be the same or a different length than the persistence length for a particular component of the molecular linker, as long as the length differential is insufficient to yield undesired interaction of the polymerizing agent and the chemical moieties (or interaction between the chemical moieties themselves). For example, if the molecular linker includes a molecular rod that has a particular persistence length, the molecular linker can be shorter or longer than that persistence length. In addition, the molecular rod length itself can be shorter or greater than the persistence length of the polymer used to generate the molecular rod. In particular examples, a molecular linker includes a molecular rod, and the total length of the rod is shorter than the persistence length of the molecule composing the molecular rod (such as 0.1-times, 0.5-times, or 1-times the persistence length of the molecule composing the molecular rod). In yet other particular examples, the length of the linker can be greater or less than the persistence length of any one of its components. For example, for a molecular linker that includes a molecular rod, the total length of the molecular linker is not more than 5-times shorter or longer than the persistence length of the molecule composing the molecular rod (such as 1-5 times, 1-4 times, or 1-3 times the persistence length of the molecular linker that includes the molecular rod). In one example, the molecular rod is composed of dsDNA (which has a persistence length of 400-500 Å) and the length of the molecular rod is greater than 400-500 Å (such as 550-700 Å or 550-1000 Å) or shorter than the persistence length (such as 100-350 Å or 200-350 Å).

Those skilled in the art will recognize that at one persistence length the far end of a rod is often still substantially pointing in the same direction (68.40°) as the original direction and that a rod of this length, and hence flexibility, can still provide a useful functional rigidity. Rods of lengths greater than the persistence length provide a further degree of flexibility that can be acceptable in some applications. In other applications a single linker can consist of a single molecule of a uniform kind (as 1000 bp of dsDNA, which is substantially longer than the persistence length) wherein certain portions of that linker are sufficiently close (for example 40 bp) that they may act as molecular rods locally and provide nanoprobe functions locally, while longer portions of the linker are sufficiently far apart as to act as molecular tethers that allow the parts to come together or not depending on Brownian motion and the presence of target molecules that can be bound. Such a situation occurs when local transcription factors bind to DNA in essentially rigid positions relative to each other, while further pieces of DNA can 'loop' around to supply, for example, an enhancer, activator or repressor (as for example in the GalR binding sites of *E. coli*, Semsey et al., *Genes Dev.* 18:1898-907, 2004). Although such nanoprobe constructions are possible, in general the constructions described herein distinguish clearly between molecular rods as being not substantially larger than the persistence length and molecular tethers as being substantially longer than their corresponding persistence length. Unlike the dsDNA transcriptional control systems found in nature, generally in the nanoprobes described herein the molecular rods and tethers are constructed by connecting different kinds of molecules that have substantially different persistence lengths as for example dsDNA with PEG.

The persistence length will vary depending on the composition. For example, the persistence length for a double-stranded DNA (dsDNA) molecule differs from that of a single-stranded DNA (ssDNA) molecule and from polyethylene glycol (PEG). For example, dsDNA has a persistence length of 400-500 Å. In particular examples, ssDNA has a persistence length of about 40 Å. In particular examples, PEG has a persistence length of about 3.8±0.02 Å (Kienberger et al., *Single Molecules* 1: 123-8, 2000).

To substantially avoid interaction of the polymerizing agent and the chemical moieties in the absence of the target nucleic acid molecule (as well as interaction between the chemical moieties themselves in the presence or absence of the target nucleic acid molecule), and allow interaction of the polymerizing agent and the chemical moieties in the presence of the target biomolecule, the length of the linker is at least sufficient to maintain the functional groups spaced at least the Förster radius for the particular donor and acceptor fluorophores used, such as a distance of 22 to 90 Å. In some examples, the length of the linker is sufficient to separate charges on the polymerizing agent and the chemical moieties, such as a distance of 10 to 1000 Å. In particular examples, the total length of the molecular linker is about 10 to 500 Å, such as 10 to 300 Å, 10 to 200 Å, 20 to 200 Å, 20 to 187 Å, 20 to 150 Å, 60 to 120 Å, or 60 to 200 Å.

Figure 1A:
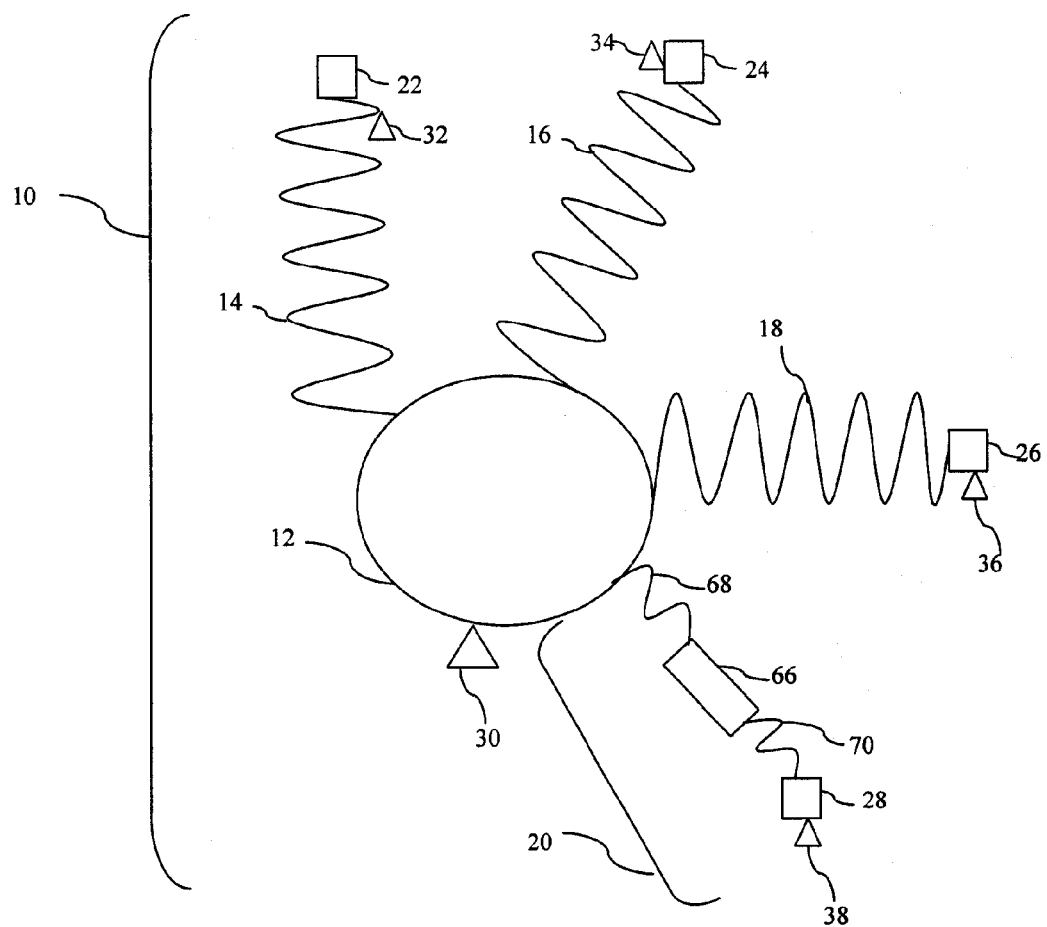
FIG. 1A is a schematic drawing showing a nanoprobe that includes a polymerizing agent with four molecular linkers to attach the chemical moieties to the polymerizing agent.

Examples of molecular linkers include, but are not limited to, tethers, molecular rods, or combinations thereof. For example, the molecular linker can include multiple molecular rods linked by tethers or multiple tethers linked by molecular rods. One particular example is shown in FIG. 1A, where the nanoprobe 10 includes a polymerizing agent 12 and a chemical moiety 28 that are linked and spaced by the molecular linker 20, wherein the molecular linker 20 is composed of a molecular rod 66 linked by tethers 68, 70. In a specific example, the molecular rod is about 100 to 200 Å (such as about 120-140 Å), and each tether is about 23 to 187 Å (such as about 60 Å).

The polymerizing agent and the chemical moieties can interact with one another and with the target nucleic acid molecule to provide a predetermined reaction, such as a detectable signal. The polymerizing agent and the chemical moieties can be maintained in a spatially separated orientation by a molecular linker so that the polymerizing agent and the chemical moieties do not interact to provide the reaction in the absence of the target molecule. However, the molecular linker permits the polymerizing agent and the chemical moieties, under predetermined conditions, to be brought into sufficient proximity with one another to interact and produce a predetermined reaction, such as a detectable signal.

In one example, each of the molecular linkers is the same or nearly identical length. In another example, two or more of the molecular linkers are different lengths. A probe with molecular linkers of varied lengths can be used to control the binding frequency of the chemical moieties. For example, if A and T nonhydrolyzable nucleotide analogs are attached to shorter molecular linkers, while C and G nonhydrolyzable nucleotide analogs are attached to longer molecular linkers, it will be easier for the A and T nucleotide analogs to get to the active site of the polymerizing agent and thereby produce a stronger emission signal.

Polymerizing Agents

Medusa probes include a polymerizing agent. Polymerizing agents are compounds (such as enzymes) that are capable of reacting monomer molecules (such as nucleotides) together in a chemical reaction to form linear chains.

Particular examples of polymerizing agents are polymerases, such as a DNA or RNA polymerase, and a ribosome. The choice of polymerase is dependent on the nucleic acid to be sequenced. For example, if the template is a single-stranded DNA molecule, a DNA-directed DNA or RNA polymerase can be used; if the template is a single-stranded RNA molecule, then a reverse transcriptase (such as an RNA-directed DNA polymerase) can be used.

Particular non-limiting examples of polymerases include *E. coli* DNA polymerase I (such as the Klenow fragment which has 3' to 5' exonuclease activity), Taq polymerase, reverse transcriptase (such as HIV-1 RT, for example the single chain HIV RT disclosed in see Le Grice et al., *J. Virol.* 62:2525:9, 1988), *E. coli* U RNA polymerase, and wheat germ RNA polymerase II.

In one example, the polymerase is HIV reverse transcriptase, which can be used to provide sequence for both DNA and RNA, and the chemical moiety is a nucleotide analog wherein the oxygen between the α and β phosphates is replaced by a nitrogen. Such nucleotide analogs can bind to a complementary nucleotide on the target nucleic acid molecule, but cannot be incorporated into the elongating complementary strand.

In one example, a polymerase is a modified polymerase. Such modification can be used to alter the biological activity of the polymerase, for example alter its substrate specificity, processivity, or accuracy. For example, the fidelity of a DNA polymerase can be increased by mutations (Wisniewski et al., *J. Biol. Chem.* 274:28175-84, 1999). For example, such a polymerase can be used to sequence double-stranded genomic DNA, as well as unfolded chromatin regions. In another example, the processivity of a DNA polymerase can be improved by covalently linking the polymerase domain to a sequence non-specific dsDNA binding protein (such as Sso7d) (for example see Wang et al., *Nucleic Acids Res.* 32(3):1197-207, 2004). In another example, an HIV-1 RT includes a mutation at position K65 to alter the nucleotide-binding specificity of the enzyme.

As described herein, in particular examples the polymerizing agent includes a tag, such as a donor fluorophore. Although the tag need not be directly attached to the polymerase (for example is attached to the polymerase via a linker), in particular examples the tag is attached to the polymerase. For example, a GFP-polymerase fusion protein can be generated using standard molecular biology methods (for example see Liu et al., *J. Biol. Chem.* 277:46712-9, 2002; and Kratz et al., *Proc. Natl. Acad. Sci. USA*, 96:1915-20, 1999).

Therefore, a polymerase can be modified (for example includes one or more amino acid substitutions) to permit attachment of a tag. For example, one or more amino acids can be substituted with a Cys using standard methods known in the art (such as site-directed mutagenesis using PCR), to permit attachment of a tag. Ideally, altering the amino acid sequence of the polymerase does not significantly interfere with the biological activity of the polymerase, such as the ability to promote synthesis of a complementary nucleic acid molecule. If desired, solvent-accessible cysteine residues can be replaced by serine residues. For example, the HIV RT p66 subunit can be mutated to K287C or W24C to permit attachment of a tag at these positions, such as the fluorophore Alexa 488 (for example see Rothwell et al., *Proc. Natl. Acad. Sci. USA*. 100:1655-60, 2003 and Kensch et al., *J. Mol. Biol.* 301:1029-39; 2000).

In a specific example, the polymerizing agent is mutant HIV-1 RT(K287C)-Tus fusion protein, with a donor fluorophore attached to the RT at cysteine 287.

In one example, the polymerizing agent is a fusion protein that includes streptavidin. Such a fusion protein can be generated using standard molecular biology methods. Attachment of a biotin to the molecular linker can be used to attach one or more molecular linkers to the streptavidin-polymerase fusion protein.

In one example, a polymerase includes both a donor fluorophore and an acceptor fluorophore. By including both fluorophores, movement or a change in conformation of the polymerase can be monitored, for example as a timing signal. In a particular example, a donor fluorophore is attached to one side of the polymerase (such as the "fingers") and an acceptor fluorophore is attached to the other side of the polymerase (such as the "thumb"). As the polymerase closes, the donor and acceptor fluorophore are brought into sufficient proximity for the donor to excite the acceptor, resulting in the production of a detectable acceptor emission signal (or a decrease in detectable donor emission signal). As the polymerase opens, the donor and acceptor fluorophore are brought sufficiently apart so that the donor cannot sufficiently excite the acceptor, resulting in a decrease in detectable acceptor emission signal (or an increase in detectable donor emission signal). If the emission from the acceptor is monitored, the increase in signal followed by a decrease in emission signal (or vice versa if the donor emission is monitored) can be used as a timing signal.

In a particular example, the donor fluorophore is EGFP (excitation 484 nm; emission 510 nm) and the acceptor fluorophore is EYFP (excitation 512 nm; emission 529 nm), wherein irradiation at 480 nm of the probe that includes such a labeled polymerase will result in emission of EGFP at 510 nm that will excite EYFP at 512 nm.

In one example, the HIV RT p66 subunit is mutated to K287C or W24C, to permit attachment of a donor fluorophore to K287C and an acceptor fluorophore to W24C (or vice versa). These two amino acid residues are on the fingers and the thumb of the polymerase, respectively, and so the distance between them can vary depending on the state of the polymerase. Therefore, such a polymerase can be used to obtain a timing signal. (Antibodies to the epitope around positions 24 or 287 can be used to block attachment of one fluorophore while the other is being attached. Alternatively other chemistries could be used to uniquely attach the donor and acceptor fluorophores.)

Table 2 shows the amino acids on a Klentaq 1 DNA polymerase whose spatial mobility changes to the greatest extent during normal polymerase activity (Li et al., *EMBO J.* 17: 7514-25, 1998). Such residues are examples of residues to which a donor or acceptor fluorophore can be attached to. For example, TRP24 is on the fingers and LYS287 is on the thumb of HIV-1 RT. During the transition from open to closed states of the polymerase, their distance will change by about 15 Å.

TABLE 2

Amino acids whose spatial mobility is altered in a Klentaq 1 DNA polymerase

| Å | Amino Acid and number |
|---|---|
| 10.232 | ARG 660 |
| 10.915 | ALA 661 |
| 11.259 | ALA 643 |
| 12.658 | SER 644 |
| 12.925 | MET 658 |
| 14.166 | PRO 656 |
| 15.050 | LEU 657 |
| 15.085 | ASP 655 |

Chemical Moieties

As described above, the chemical moieties linked to the polymerase via molecular linkers are agents that are capable of binding to the template nucleic acid molecule, without being detached from the linker, by pairing with the exposed complementary nucleotide in the target nucleic acid molecule. For example, chemical moieties will enter the polymerase active site for a sufficient amount of time to generate a detectable signal, without being permanently incorporated into the elongating complementary strand. Although the chemical moiety may form one or more chemical bonds with the active site, base pair with the elongating complementary strand and bind with the template nucleic acid, such bonds are reversible to permit replacement of the chemical moiety by a hydrolyzable nucleotide, wherein the hydrolyzable nucleotide becomes non-reversibly incorporated into the elongating complementary strand. This steps the polymerizing agent forward one base. Since the chemical moieties are not removed from the linker, the probe can be used again.

Particular examples of such chemical moieties include nucleotide analogs, such as a nonhydrolyzable nucleotide analog (for example a nonhydrolyzable triphosphate nucleotide analog), for example those available from Molecular Probes, such as BODIPY FL AMPPNP (B22356) and BODIPY FL GMPPNP (B22355) as well as mononucleotides. In a specific example, the nonhydrolyzable triphosphate nucleotide analog is a nonhydrolyzable triphosphate nucleotide analog with an alpha-beta bond that is nonhydrolyzable.

Nonhydrolyzable nucleotide analogs are commercially available (for example Jena Bioscience (Jena, Germany) sells nonhydrolyzable analogs for all four dNTP bases, such as α, β-methylene-ATP; α, β-N-dUTP; α, β-C-GTP). In addition, all four dNTP analogs containing —NH— or —CH$_2$— groups between the α and β-phosphates can be commercially produced (for example by Jena Bioscience).

In a particular example, the nanoprobes disclosed herein include a large number of nucleotides (such as hydrolyzable nucleotides), thereby providing a self-contained sequencing probe. This can allow the sequencing probe to report a limited number of bases in a sequence. The nucleotides can be present on the molecular linkers. For example, once a nucleotide that was originally attached on the γ-phosphate has been used, it would be incorporated into the nucleic acid molecule to be sequenced, and therefore that molecular linker would no longer participate in the sequencing reaction.

Tethers

Molecular linkers can include one or more tethers, which can provide flexibility to the probe. Ideally, tethers are flexible enough to allow movement of the chemical moieties, for example to permit the chemical moieties to interact with the polymerizing agent and with the target nucleic acid molecule (such as the exposed base on the target nucleic acid molecule). The length of the tether should be sufficient to substantially avoid interaction of the chemical moieties and the polymerizing agent in the absence of the target nucleic acid molecule, and allow interaction of the chemical moieties and the polymerizing agent in the presence of the target nucleic acid molecule. However, the tether is ideally not so long as to result in entanglement of the tether or the chemical moieties (for example with each other, or with the polymerizing agent). In particular examples, tethers are water soluble and non-toxic.

In particular examples, the length of the tether is long enough to separate the chemical moieties in the absence of the target nucleic acid molecule, but not so long as to result in tangling of the nanoprobe or the chemical moieties, and short enough to allow the chemical moieties to interact with the target nucleic acid molecule and the polymerizing agent.

Examples of particular materials that can be used as tethers include, but are not limited to, single-stranded DNA molecules, sugar chains, peptides (such as the connector between two parts of the RecB protein), and polyethylene glycol (PEG) or any other flexible polymer having the properties disclosed herein. In a particular example, a tether is composed of two or more of these agents. In a specific example a tether includes, or in some examples consists of, PEG.

In particular examples, the tether is about 10-500 Å, such as 20-200 Å, 23-187 Å, 100-140 Å, or 70-94 Å, for example 120 Å. In one example, the tether is less than 187 Å in length.

In particular examples, the tether is composed of PEG, such as 3 to 7 units of 18-atom PEG spacers that are 23.4 Å long, such as 2-4 or 3-4 of such spacers. PEG is non-toxic, flexible, hydrophilic, and can be inserted as spacers during DNA synthesis (SyntheGen, Glen Research).

In one example, the tether is a single-stranded DNA (ssDNA) molecule, for example having a length of 10-40 nucleotides, such as 10-30 nucleotides, 10-20 nucleotides, for example 10 nucleotides, 20 nucleotides, or 40 nucleotides. In particular examples, a ssDNA tether can anneal to another nucleic acid strand, thereby converting a flexible tether into a rigid molecular rod. Ideally, the sequence is one that does not specifically hybridize to itself, the functional groups, or to a nucleic acid sequence in the sample to be analyzed.

In one example, the tether is a sugar chain (for example having a length of 10-100 sugar moieties, such as 10-75, 10-50, or 20-40 sugar moieties).

In one example, tethers include charges (such as a —COO$^-$ or —NH$_3^+$), to reduce entanglement of the molecular linkers that include the charged tethers.

Molecular Rods

Molecular linkers can include one or more molecular rods, which can provide sufficient rigidity to the probe to reduce interaction of the chemical moieties and the polymerizing agent in the absence of the target nucleic acid molecule (or interaction of the chemical moieties themselves in the presence or absence of the target nucleic acid molecule, for example due to entanglement of the molecular linkers). However, the length of the rod is sufficient to permit interaction of the chemical moieties and the polymerizing agent in the presence of the target nucleic acid molecule. In some examples, the presence of a molecular rod in the nanoprobe reduces the likelihood of entanglement and can increase the speed of the binding of the chemical moieties to the active site of the polymerizing agent.

The disclosed nanoprobes can include one or more molecular rods, such as at least two molecular rods, for example 1, 2, 3, 4, 5, 6, 7, 8, 9, or 10 molecular rods. In one example, use of one or more molecular rods reduces the required tether length, thereby reducing the cost and size of the device.

In a particular example, the molecular rod is a dsDNA sequence. The length of the dsDNA is one that allows interaction of the chemical moieties and the polymerizing agent in the presence of the target nucleic acid molecule, but reduces their interaction in the absence of the target nucleic acid molecule. If the nanoprobe includes donor and acceptor fluorophores, the length of the dsDNA is one that allows interaction of the fluorophores in the presence of the target nucleic acid molecule, but reduces their interaction in the absence of the target nucleic acid molecule. In specific examples, the dsDNA molecular rod is a length that is about equal to the persistence length of 400-500 Å. However, one skilled in the art will recognize that lengths shorter or greater can be used, as long as the rod reduces the interaction of functional groups in the absence of the target biomolecule, and does not result in significant entanglement of a molecular linker. In specific examples, the dsDNA molecular rod is 150 to 200 nucleotides, such as 10-150 nucleotides, such as 10-140 nucleotides, 20-140 nucleotides, 20-100 nucleotides, 20-50 nucleotides, 30-50 nucleotides, or 3040 nucleotides, for example 35, 36, 37, 38, 39, 40, 41, 42, 43, 44, or 45 nucleotides. In specific examples, the dsDNA molecular rod is at least 10 nucleotides, such as at least 20 nucleotides. In a particular example, the molecular rod is a dsDNA of 40 bases. Bases are 3.38 Å thick so 40 base pairs is 135 Å long, which is greater than the typical FRET distance. In a particular example, the sequence of the dsDNA is chosen using the NANEV program (Goodman et al., *BioTechniques*, 38:548-50, 2005).

In other particular examples, the molecular rod is composed of DNA molecules containing modifications or variants of the DNA, such as peptide backbone DNA (Peptide Nucleic Acid, PNA) or locked nucleic acids (LNAs). In particular examples, such DNA variants are used to alter the helix thermal stability and resistance to nucleases. In yet another example the molecular rod is composed of carbon nanotubes (for example nanotubes that are 100-200 Å in length). In yet other examples, the molecular rod includes bacteria, virus particles, or viral tail fibers.

Branched Molecular Linkers

Figure 1B:
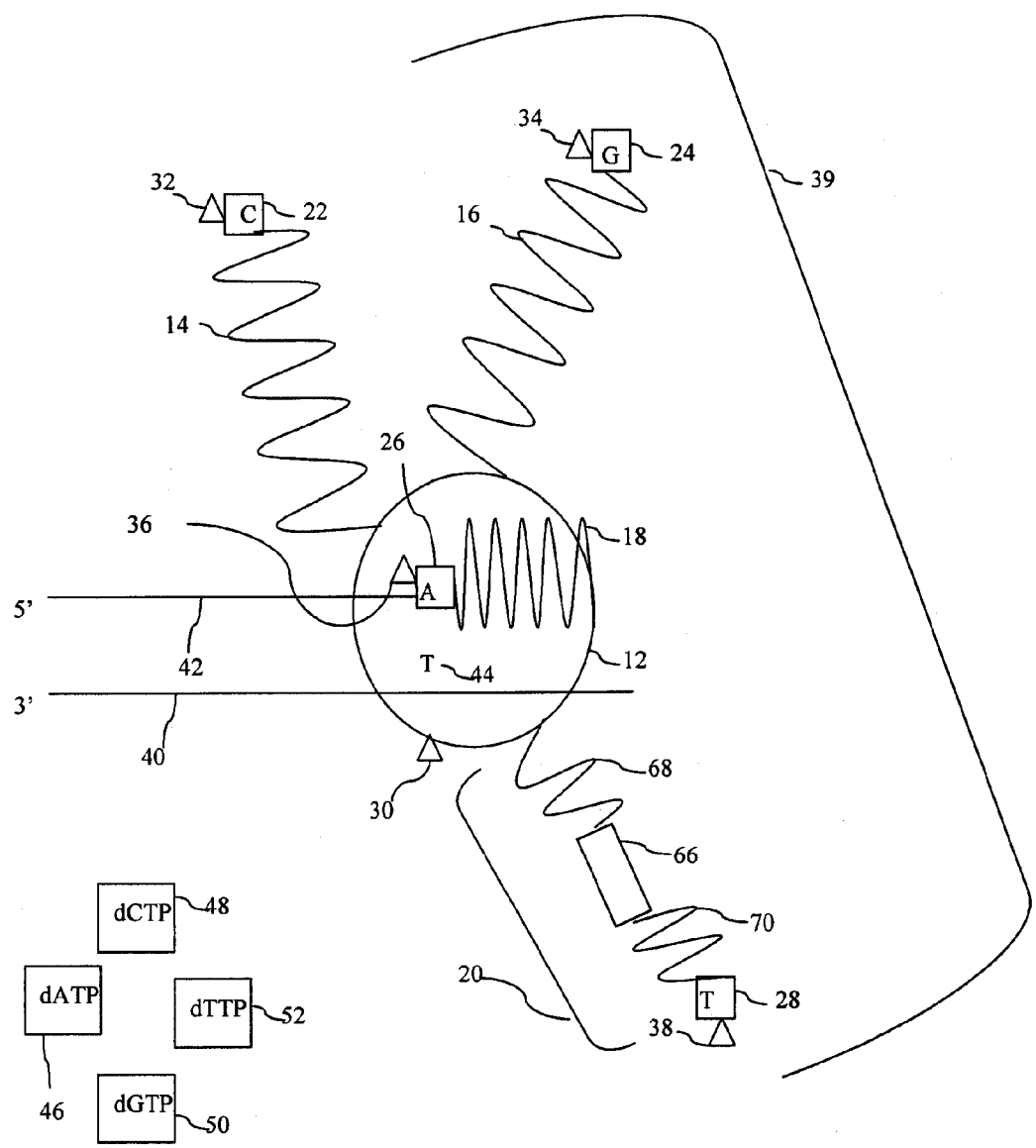
FIG. 1B is a schematic drawing showing the nanoprobe attached to a target nucleic acid strand and a complementary primer, and the pairing of one of the chemical moieties with its complementary nucleotide in the target nucleic acid strand.
Figure 1C:
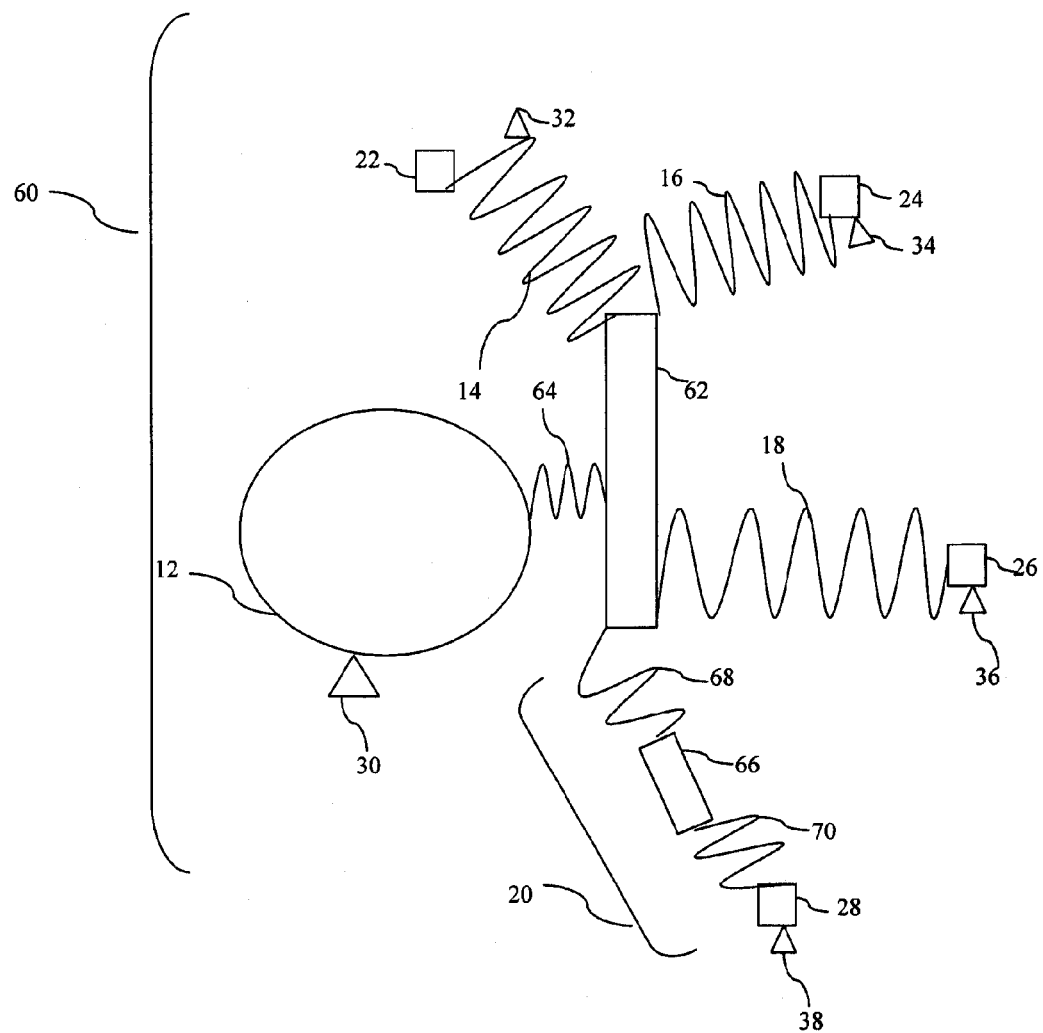
FIG. 1C is a schematic drawing showing a nanoprobe that includes a polymerizing agent with chemical moieties linked to a "hub" created by a molecular linker attached at a single point on the polymerase via a tether.

In particular examples, the molecular linker is composed of multiple parts that form a branched structure, for example as shown in FIG. 1C. Such a structure can be created by appropriately annealing single strands of synthetic DNA as described herein.

Alternatively, 5-Me-dC Brancher Phosphoramidites are available for use in oligonucleotide synthesis. Synthesis of a first strand can be performed such that a 5-Me-dC Brancher Phosphoramidite is incorporated in the middle of the strand. The end of the strand is then capped, the 5-Me-dC Brancher is then unblocked and synthesis then proceeds on the second branch. This creates a Y shaped molecule. Two such molecules can be synthesized that have complementary sequences so that they form a single rod in the center flanked by four arms. By appropriate the choice of sequences in the arms and design of other oligonucleotides complementary to those arms, a structure like that shown in FIG. 1C can be created.

Tags

In particular examples, nanoprobes disclosed herein include one or more tags, such as a detectable label, for example to permit sequencing of a target nucleic acid molecule. Exemplary tags that can be used include fluorophores, chemiluminescent agents, and charge. In particular examples, a change in charge is detected as the target nucleic acid molecule approaches a capacitor.

In a particular example, a nanoprobe includes an acceptor fluorophore and one or more donor fluorophores. In the figures that only show a single donor or single acceptor fluorophore on the nanoprobe, one skilled in the art will appreciate that multiple fluorophores can be included on the nanoprobe, for example to increase the signal or to provide combinations of spectra. Ideally, the acceptor and donor fluorophores are attached to the nanoprobe in a position that decreases their interaction in the absence of the target biomolecule (thereby reducing detectable signal). However, in the presence of the target biomolecule, the interaction of the polymerizing agent and the chemical moieties with each other and with the exposed base on the target nucleic acid molecule allows the acceptor and donor fluorophores to interact, such that the donor fluorophore excites the acceptor fluorophore and the acceptor emits at its characteristic wavelengths, thereby generating a detectable signal.

In a particular example, the donor fluorophore has a large Stokes shift. This decreases the excitation of the acceptor fluorophore by the donor excitation light frequency. Appropriate filtration can also reduce or remove the excitation wavelength, leaving only the emission spectrum from the acceptor to be detected.

In a particular example, the donor fluorophore is Green Fluorescent Protein (GFP), or a variant thereof. For example, one or more GFP molecules can be cloned onto a polymerizing agent (for example to generate a GFP-polymerase fusion protein) using standard molecular biology methods. In another particular example, the donor fluorophore is a chemiluminescent molecule, such as aequorin. Chelated lanthanides provide bright, large stokes shift, non-bleaching luminophores with sharp emission spectra, and can therefore be used as donors. The use of a chemiluminescent molecule as the donor fluorophore eliminates the need for an external light source. Similar to GFP, chemiluminescent molecules such as aequorin can be cloned onto a polymerizing agent using standard molecular biology methods (for example to generate an aequorin-polymerase fusion protein).

Each different type of chemical moiety linked to the polymerizing enzyme can be associated with one or more different tags, such as one or more fluorophores. In a particular example, each different type of chemical moiety is associated with one or more different acceptor fluorophores, which can be excited by a donor fluorophore (or luminescent molecule associated with the polymerizing agent).

Particular examples of acceptor and donor fluorophore pairs that can be used include, but are not limited to: GFP mutant H9-40 (Tsien, 1998, *Ann. Rev. Biochem.* 67:509) as a suitable donor fluorophore for use with BODIPY, fluorescein, rhodamine green, Oregon green, tetramethylrhodamine, Lissamine™, Texas Red and naphthofluorescein as acceptor fluorophores, and fluorophore 3-($\epsilon$-carboxy-pentyl)-3'-ethyl-5,5'-dimethyloxacarbocyanine (CYA) as a donor fluorophore for fluoresce in or rhodamine derivatives (such as R6G, TAMRA, and ROX) as acceptor fluorophores. Other particular examples of acceptor and donor fluorophore pairs include, but are not limited to: 7-dimethylaminocoumarin-4-acetic acid (DMACA) and fluorescein-5-isothiocyanate (FITC); 7-amino-4-methyl-3-coumarinylacetic acid (AMCA) and fluorescein-5-isothiocyanate (FITC); and fluorescein-5-isothiocyanate (FITC) and tetramethylrhodamine isothiocyanate (TRITC).

Particular examples of fluorescent tags that can be used include the Alexa Fluor series (Molecular Probes, Eugene, Oreg.). Alexa Fluor 430 absorbs at 430 nm and, because of its high Stokes shift, emits far away at 540 nm, and can therefore be used as a donor fluorophore. Alexa Fluor 430 can be used in particular examples with Alexa Fluors 546, 555, 568, 594, 647, and BODIPY 630 as acceptor fluorophores since their excitation spectra overlap the 540 nm emission peak of Alexa Fluor 430.

Donor and acceptor molecules can also be designed using bimolecular fluorescence complementation (BiFC) (Hu et al., *Nat. Biotechnol.* 21:539-45, 2003; Hu et al., *Mol. Cell.* 9:789-98, 2002). Two partial GFP fragments join to give a complementation and hence fluorescence. The complementation takes only a few moments but formation of the chromophore takes a long time, $t_{1/2}$=300 seconds. So the method can be slower than FRET. Because the chromophore forms permanently, it can be used in a nanoprobe to provide a long-lasting result.

In one example, the tag is a quencher. For example, if a quencher is used in combination with an acceptor fluorophore, the decreased acceptor signal is the detectable signal. In another example, a quencher is used in combination with a donor fluorophore, the decreased acceptor signal is the detectable signal.

Quantum Dots

In one example, one or more Medusa probes disclosed herein are attached to fluorescent nanoparticles referred to as quantum dots. The quantum dot or Cornell dot (silica coated fluorophores) can be the donor fluorophore, while the nanoprobes attached to the quantum dot can include one or more corresponding acceptor fluorophores (for example associated with the chemical moieties). In particular examples, the nanoprobes are attached to the quantum dot directly, or via a linker, such as with antibodies coating the quantum dot.

The quantum dots can be tethered together, for example with a molecular linker of a sufficient length to prevent significant FRET. In another example, quantum dots are tethered together using a molecular linker (such as tetrahedron constructions) that keep the chemical moieties a significant distance from the surface of the quantum dot. Then when a chemical moiety on the nanoprobe pairs with the complementary exposed base on the target nucleic acid molecule, the chemical moiety is detected by FRET.

Attachment of Probe to a Substrate

In particular examples, the probes of the present disclosure are attached to a substrate, for example via a linker. Therefore, provided by the present disclosure are probes attached to a substrate.

In particular examples, the polymerizing agent of the probe is attached to a substrate, such as glass or a plastic material. Methods of attaching proteins to a substrate are known in the art. For example, a linker can be used to attach the polymerizing agent to a substrate. Ideally, the linker does not significantly interfere with the biological activity of the polymerizing agent. The linker can be a covalent or non-covalent means of attachment.

In one example, the linker is a pair of molecules, having high affinity for one another, one molecule on the polymerase (such as an affinity tag), the other on the substrate. Such high-affinity molecules include streptavidin and biotin, histidine and nickel (Ni), histidine and Si, and GST and glutathione. When the polymerase and substrate are brought into contact, they bind to one another due to the interaction of the high-affinity molecules. For example, a polymerase can be engineered to include a 6X His-tag (for example using standard molecular biology methods), and then attached to a surface that includes Si (for example see Cha et al., *Proteomics* 4:1965-76, 2004). Similarly, a polymerase can be engineered to include an S-tag, glutathione-S-transferase (GST), or streptavidin.

In another example, the linker is a straight-chain or branched amino- or mercapto-hydrocarbon with more than two carbon atoms in the unbranched chain. Examples include aminoalkyl, aminoalkenyl and aminoalkynyl groups. Alternatively, the linker is an alkyl chain of 10-20 carbons in length, and may be attached through a Si—C direct bond or through an ester, Si—O—C, linkage (see U.S. Pat. No. 5,661,028 to Foote, herein incorporated by reference). Other linkers are provided in U.S. Pat. No. 5,306,518 to Prober et al., column 19; and U.S. Pat. No. 4,711,955 to Ward et al., columns 8-9; and U.S. Pat. No. 5,707,804 to Mathies et al. columns 6-7 (all herein incorporated by reference).

Exemplary Nanoprobes for Sequencing

The present disclosure provides multiple examples of nanoprobes that can be used to sequence one or more target nucleic acid sequences.

One particular example of a probe of the present disclosure is shown in, FIG. 1A. The probe 10 includes polymerizing agent 12, and four molecular linkers 14, 16, 18, 20 that attach the chemical moieties 22, 24, 26, 28 to the polymerizing agent 12. The chemical moieties 22, 24, 26, 28 are capable of interacting with one another or with polymerizing agent 12 in a predetermined reaction, wherein the molecular linkers 14, 16, 18, 20 maintain the chemical moieties 22, 24, 26, 28 sufficiently spaced from one another and from the polymerizing agent 12 in the absence of a target nucleic acid. In particular examples, the chemical moieties 22, 24, 26, 28 are spaced a distance from one another to avoid substantial entanglement of the chemical moieties 22, 24, 26, 28.

In some examples, the probe 10 includes a tag 30 that is associated with the polymerizing agent 12 and different tags 32, 34, 36, 38 that are associated with the chemical moieties 22, 24, 26, 28, respectively. Probe 10 shows the tag 30 directly attached to the polymerizing agent 12 and the tags 34, 36, 38 directly attached to the chemical moieties 24, 26, 28, respectively. In contrast, tag 32 is not attached directly to chemical moiety 22 but is attached to linker 14 in sufficient proximity to chemical moiety 22 to emit a signal when chemical moiety 22 pairs with its complementary nucleotide in the target nucleic acid molecule. Similarly, tag 30 could be attached to the polymerizing agent 12 via a linker.

The molecular linkers 14, 16, 18, 20 are of a length and/or rigidity such that the chemical moieties 22, 24, 26, 28 do not substantially interact with one another or with the polymerizing agent 12 in an absence of the target nucleic acid molecule. However, in the presence of the target nucleic acid molecule, the molecular linkers 14, 16, 18, 20 permit the chemical moieties 22, 24, 26, 28 to sufficiently interact with the polymerizing agent 12 in the presence of the target nucleic acid molecule in the predetermined reaction. For example, in the presence of the target nucleic acid molecule the polymerizing agent 12 attaches to the target and its complementary primer to permit the tags 32, 34, 36, 38 on or near the chemical moieties 22, 24, 26, 28 to interact with the tag 30 of polymerizing agent 12 (for example when tag 30 is adjacent to the active site of the polymerizing agent) and with the target nucleic acid molecule, to yield a signal (such as light). For example, as shown in FIG. 1B, probe 39 can bind to a target nucleic acid molecule 40 (not part of the probe) and to its complementary primer 42 (not part of the probe), from which the complementary strand elongates. As shown in FIG. 1B, the next nucleotide on the target nucleic acid molecule 40 is a "T" 44, which can specifically pair with the complementary chemical moiety (shown here as mononucleotide "A" 26). The molecular linker 18 is of a sufficient length and flexibility to bend towards polymerizing agent 12 and permit the mononucleotide "A" 26 to reversibly interact with the complementary strand 42, and pair with complementary nucleotide T 44. However, "A" 26 will not be incorporated permanently into the complementary strand 42. Instead, "A" 26 will be replaced with a hydrolyzable dATP 46 (not part of the probe) that is present in the sequencing reaction (along with other nucleotides dCTP 48, dGTP 50, dTTP 52 that are not part of the probe) that can be incorporated into the elongating complementary strand 42. The pairing of "A" 26 with "T" 44 on the target nucleic acid molecule 40 will generate a detectable signal due to the interaction of the tag 30 associated with the polymerizing agent 12 and the tag 36 associated with "A" 26. However, the other chemical moieties 22, 24, 28 will not be present in the active site of the polymerizing agent for a sufficient amount of time to generate a detectable signal as they are not complementary to the "T" 44 in the target nucleic acid molecule 40.

The probe 10 shown in FIG. 1A is an example of showing the attachment of a plurality of molecular linkers 14, 16, 18, 20, to multiple points on the polymerizing enzyme 12. An alternative example showing the attachment of a plurality of molecular linkers to a single point on the polymerizing enzyme is shown in FIG. 1C. The probe 60 includes a polymerizing enzyme 12 and a molecular linker composed of multiple tethers 14, 16, 18, 20 attached to a molecular rod 62 which acts as a "hub". The molecular linker is attached to the polymerizing enzyme 12 at one point via a linker 64 which allows the "hub" 62 to rotate freely, thereby providing equal access to the polymerizing enzyme 12.

FIGS. 2A-D show Medusa nanoprobes that can be used to sequence a nucleic acid molecule, wherein the molecular linker is a branched structure attached to the polymerizing agent at a single point. However, one skilled in the art will appreciate that multiple branched molecular linkers can be attached to a single polymerizing agent.

Figure 2A:
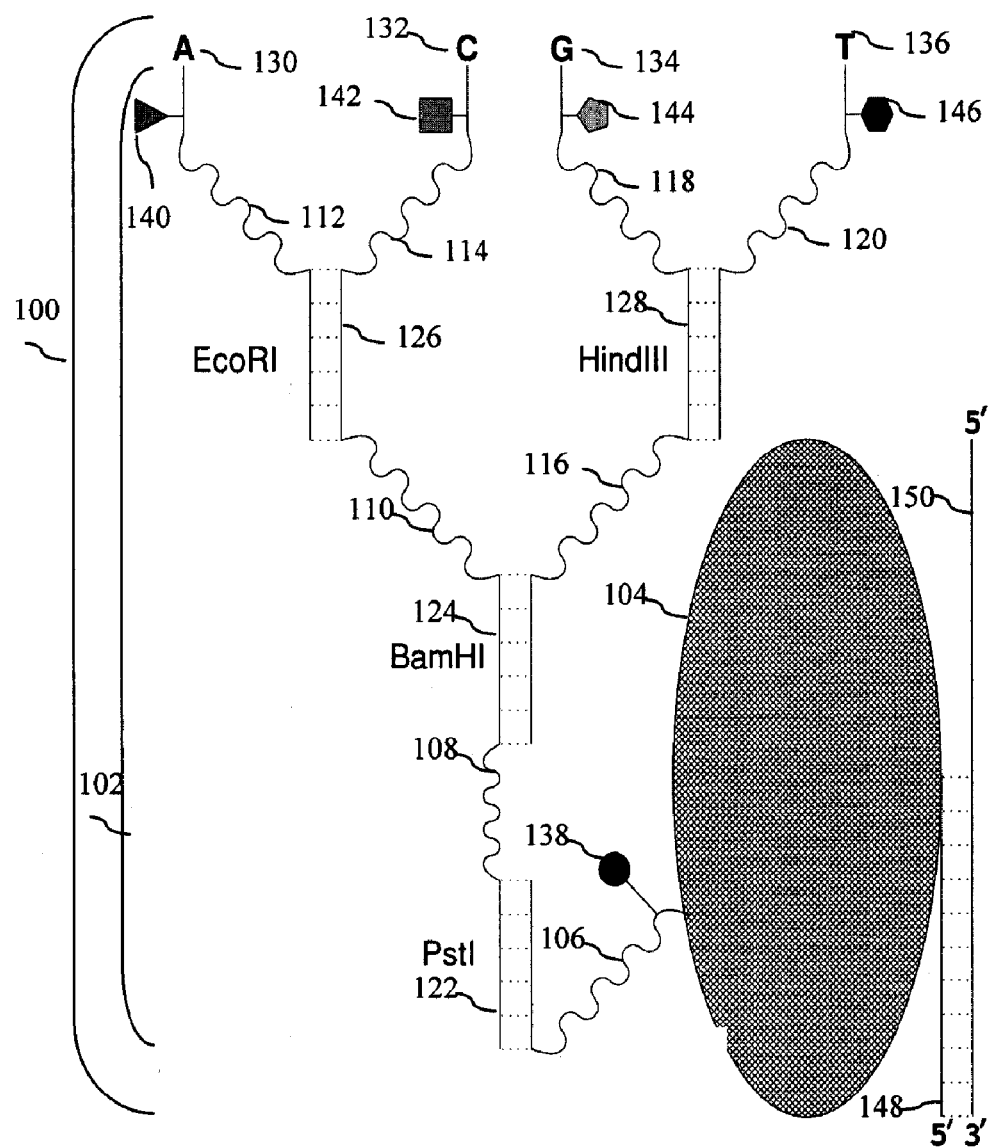
FIGS. 2A-D are schematic drawings of nanoprobes having the molecular linkers attached to the polymerizing agent at a single location in a variety of different configurations.

The probe 100 shown in FIG. 2A includes a molecular linker 102 having a branched structure. The molecular linker 102 is attached to the polymerizing agent 104 at a single point via tether 106. The molecular linker 102 includes multiple tethers 106, 108, 110, 112, 114, 116, 118, 120 and multiple molecular rods 122, 124, 126, 128. The tethers 106, 108, 110, 112, 114, 116, 118, 120 provide flexibility to the probe, and the molecular rods 122, 124, 126, 128 provide rigidity, for example to decrease entanglement of the branches of the molecular linker 102. The chemical moieties 130, 132, 134, 136 shown here as nonhydrolyzable A 130, C 132, G 134, and T 136 analogs, are attached to the molecular linker 102 at the ends of the tethers 112, 114, 118, 120 respectively. For example, the four nonhydrolyzable nucleotide analogs 130, 132, 134, 136 can be attached by their γ-phosphate to an amino terminated polyethylene glycol (PEG) tether 112, 114, 118, 120. The tethers 112, 114, 118, 120 allow free rotation of each segment, so that each of the four chemical moieties 130, 132, 134, 136 has equal access to the polymerizing agent 104. Tethers 112, 114, are attached to molecular rod 126 and tethers 118, 120 are attached to molecular rod 128. The molecular rods 126, 128 are connected together by tethers 110, 116 that are joined by another molecular rod 124. Molecular rod 124 is connected to tether 108, which is connected to molecular rod 122, which is connected to tether 106 that attaches to the polymerizing agent 104. For example, tether 106 can include an amino terminus that is attached to the polymerizing agent 104 via a cysteine or a different chemically modified residue on the polymerizing agent 104. In particular examples, the tethers 106, 108, 110, 112, 114, 116, 118, 120 are composed of PEG, and the molecular rods 122, 124, 126, 128 are composed of dsDNA. If desired, the dsDNA can include restriction sites as indicated in FIG. 2A, (such as EcoRI, BamHI, PstI or HindIII) which can be used to confirm the proper construction of the probe.

Probe 100 also includes a tag 138 associated with the polymerizing agent 104, and different tags 140, 142, 144, 146 associated with each chemical moiety 130, 132, 134, 136 respectively. In probe 100, the tags 138, 140, 142, 144, 146 are not directly attached to the polymerizing agent 104 or the chemical moieties 130, 132, 134, 136. Instead, the tags 138, 140, 142, 144, 146 are located on part of the molecular linker 106, 112, 114, 118, 120. The probe 100 is shown bound to a primer 148, which is hybridized to a target nucleic acid molecule 150. However, the primer 148 and the target nucleic acid molecule 150 are not part of the probe 100. The molecular rods 122, 124, 126, 128 can provide rigidity, for example to reduce the interaction of the chemical moieties 130, 132, 134, 136 with the polymerizing agent 104 in the absence of the target nucleic acid molecule 150, or to reduce the interaction of tag 138 with tags 140, 142, 144, 146 in the absence of the target nucleic acid molecule 150. In addition, the molecular rods 122, 124, 126, 128 reduce the interaction of the three non-complementary chemical moieties when the complementary chemical moiety is bound to the target nucleic acid molecule 150 in the binding pocket of the polymerizing agent 104.

Figure 2B:
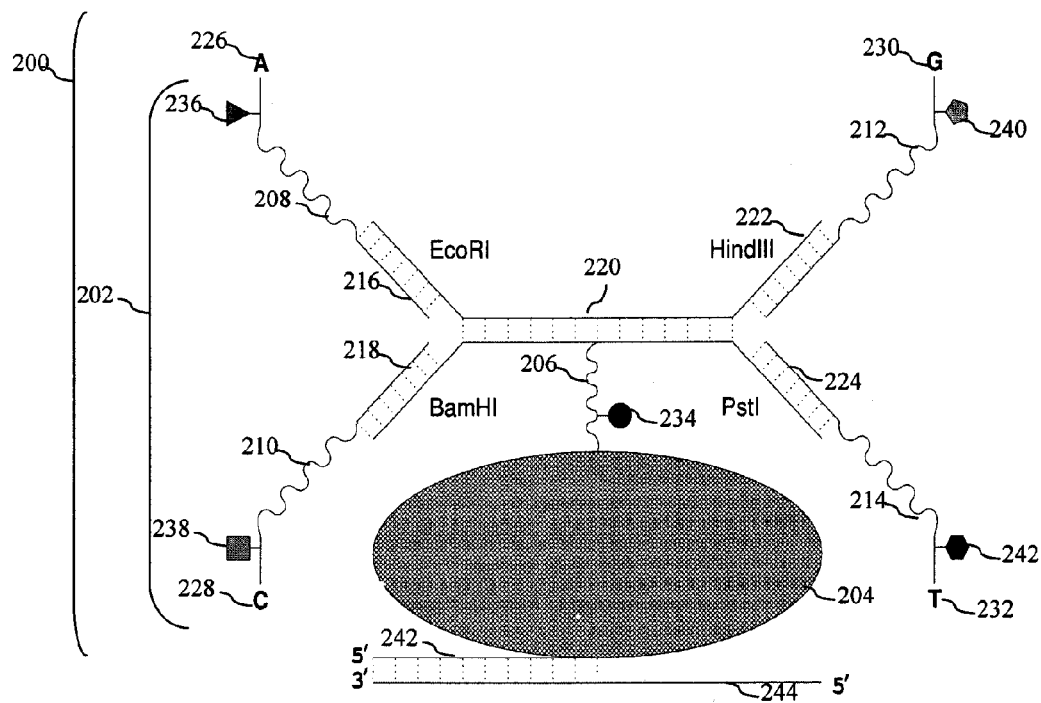

A variant of probe 100 is shown in FIG. 2B. Probe 200 also includes a molecular linker 202 having a branched structure; however the branched structure is more symmetrical. For example, in probe 100, when one of the chemical moieties (such as 130) is bound to the active site of the polymerizing agent 104, one of the other chemical moieties (such as 132) is closer than the other chemical moieties (such as 134, 136). This may increase background signal, for example if donor and acceptor fluorophores are included in the probe 100. In contrast, probe 200 allows all chemical moieties the same access to the polymerizing agent.

The molecular linker 202 is attached to the polymerizing agent 204 at a single point via tether 206. The molecular linker 202 includes multiple tethers 206, 208, 210, 212, 214 and multiple molecular rods 216, 218, 220, 222, 224. The tethers 206, 208, 210, 212, 214 provide flexibility to the probe, and the molecular rods 216, 218, 220, 222, 224 provide rigidity, for example to decrease entanglement of the branches of the molecular linker 202. The chemical moieties 226, 228, 230, 232, shown here as nonhydrolyzable A 226, C 228, G 230, and T 232 analogs, are attached to the molecular linker 202 at the ends of the tethers 208, 210, 212, 214, respectively. For example, the four nonhydrolyzable nucleotide analogs 226, 228, 230, 232 can be attached by their γ-phosphate to an amino-terminated polyethylene glycol (PEG) tether 208, 210, 212, 214. The tethers 206, 208, 210, 212, 214 allow free rotation of each Medusa "arm", so that each of the four chemical moieties 226, 228, 230, 232 has equal access to the polymerizing agent 204. Tethers 208, 210 are attached to molecular rods 216, 218, respectively, and molecular rods 216, 218 are attached to molecular rod 220. In particular examples, molecular rods 216, 218, 222, 224 are each 20 nucleotides of ds DNA. Molecular rod 220 is also attached to molecular rods 222, 224, which are attached to tether 212 and 214, respectively. Molecular rod 220 is connected to tether 206, which attaches to the polymerizing agent 204. In particular examples, the tethers 206, 208, 210, 212, 214 are composed of PEG, and the molecular rods 216, 218, 220, 222, 224 are composed of dsDNA. If desired, the dsDNA can include restriction sites as indicated in FIG. 2B, (such as EcoRI, BamHI, PstI or HindIII) which can be used to confirm the proper construction of the probe. In one example, the polymerizing agent 204 is attached to the molecular linker by including a ter DNA site in molecular rod 220, wherein the polymerizing agent 204 is a polymerase-Tus fusion protein. The ter DNA site will specifically bind to the Tus protein. This eliminates the need for tether 206.

Probe 200 also includes a tag 234 associated with the polymerizing agent 204, and different tags 236, 238, 240, 242 associated with each chemical moiety 226, 228, 230, 232, respectively. In probe 200, the tags 234, 236, 238, 240, 242 are not directly attached to the polymerizing agent 204 or the chemical moieties 226, 228, 230, 232. Instead, the tags 234, 236, 238, 240, 242 are located on part of the molecular linkers 206, 208, 210, 212, 214. The probe 200 is shown bound to a primer 242, which is hybridized to a target nucleic acid molecule 244. However, the primer 242 and the target nucleic acid molecule 244 are not part of the probe 200. The molecular rods 216, 218, 220, 222, 224 can provide rigidity, for example to reduce the interaction of the chemical moieties 226, 228, 230, 232 with the polymerizing agent 204 in the absence of the target nucleic acid molecule 244, or to reduce the interaction of tag 234 with tags 236, 238, 240, 242 in the absence of the target nucleic acid molecule 244. For example, molecular rod 220 can keep the individual branches of the molecular linker 202 away from the tag 234 in the absence of target nucleic acid molecule 244. In addition, the molecular rods reduce the interaction of the three non-complementary chemical moieties when the complementary chemical moiety is bound to the target nucleic acid molecule 244 in the binding pocket of the polymerizing agent 204.

Figure 2C:
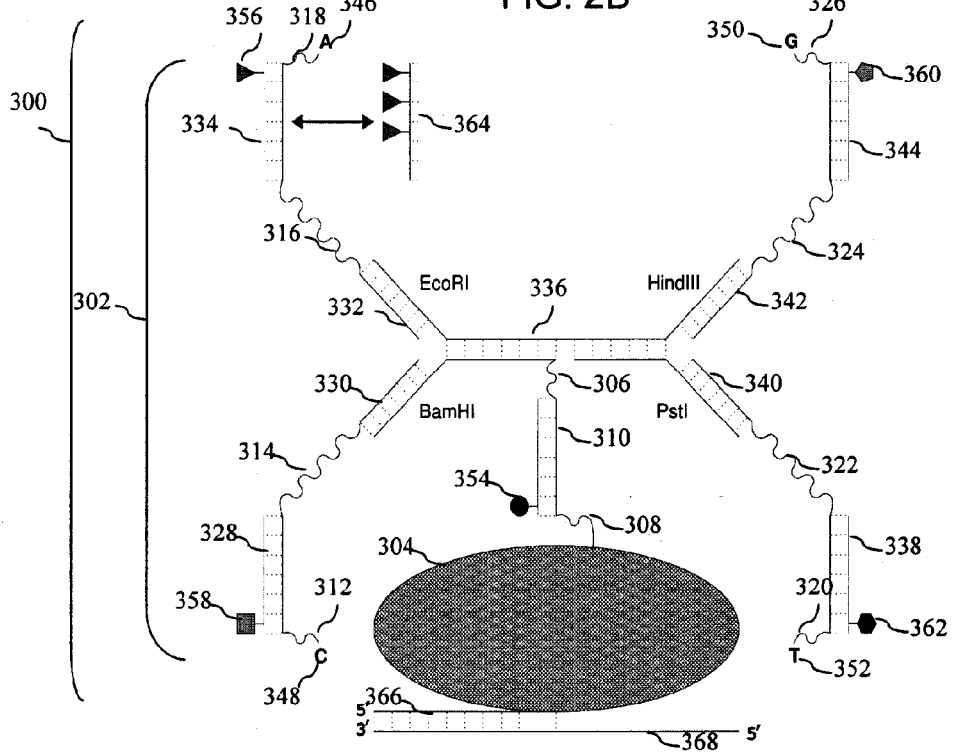

A variant of probes 100 and 200 is shown in FIG. 2C. Probe 300 also includes a molecular linker 302 having a branched structure. Probe 300 shows the use of DNA hybridization to construct a probe using only one amino group per molecular rod/tether (such as a DNA/PEG chain). The molecular linker 302 is attached to the polymerizing agent 304 at a single point via tethers 306, 308 joined by molecular rod 310. The molecular linker 302 includes multiple tethers 306, 308, 312, 314, 316, 318, 320, 322, 324, 326 and multiple molecular rods 310, 328, 330, 332, 334, 336, 338, 340, 342, 344. The tethers 306, 308, 312, 314, 316, 318, 320, 322, 324, 326 provide flexibility to the probe, and the molecular rods 310, 328, 330, 332, 334, 336, 338, 340, 342, 344 provide rigidity, for example to decrease entanglement of the branches of the molecular linker 302. The chemical moieties 346, 348, 350, 352, shown here as nonhydrolyzable A 346, C 348, G 350, and T 352 analogs, are attached to the molecular linker 302 at the ends of the tethers 318, 312, 326, 320, respectively. For example, the four nonhydrolyzable nucleotide analogs 346, 348, 350, 352 can be attached by their γ-phosphate to an amino terminated polyethylene glycol (PEG) tether 318, 312,

326, 320. The tethers 314, 316, 322, 324 allow free rotation of each segment, so that each of the four chemical moieties 346, 348, 350, 352 has equal access to the polymerizing agent 304. In particular examples, the tethers 306, 308, 312, 314, 316, 318, 320, 322, 324, 326 are composed of PEG, and the molecular rods 310, 328, 330, 332, 334, 336, 338, 340, 342, 344 are composed of dsDNA. If desired, the dsDNA can include restriction sites as indicated in FIG. 2C, (such as EcoRI, BamHI, PstI or HindIII) which can be used to confirm the proper construction of the probe.

Probe 300 also includes a tag 354 associated with the polymerizing agent 304, and different tags 356, 358, 360, 362 associated with each chemical moiety 346, 348, 350, 352, respectively. In probe 300, the tags 354, 356, 358, 360, 362 are not directly attached to the polymerizing agent 304 or the chemical moieties 346, 348, 350, 352. Instead, the tags 354, 356, 358, 360, 362 are located on part of the molecular linker 310, 334, 328, 344, 338. FIG. 2C (double-headed arrow) also shows how multiple tags can be associated with each chemical moiety (such as multiple fluorophores or dendrimers), for example to reduce loss of the signal by bleaching. For example molecular rod 334 can be formed by DNA hybridization with a ssDNA including multiple tags 364, instead of a ssDNA including only one tag. The probe 300 is shown bound to a primer 366, which is hybridized to a target nucleic acid molecule 368. However, the primer 366 and the target nucleic acid molecule 368 are not part of the probe 300. The molecular rods 310, 328, 330, 332, 334, 336, 338, 340, 342, 344 can provide rigidity, for example to reduce the interaction of the chemical moieties 346, 348, 350, 352 with the polymerizing agent 304 in the absence of the target nucleic acid molecule 368, or to reduce the interaction of tag 354 with tags 356, 358, 360, 362 in the absence of the target nucleic acid molecule 368. In addition, the molecular rods reduce the interaction of the three non-complementary chemical moieties when the complementary chemical moiety is bound to the target nucleic acid molecule 368 in the binding pocket of the polymerizing agent 304.

Figure 2D:
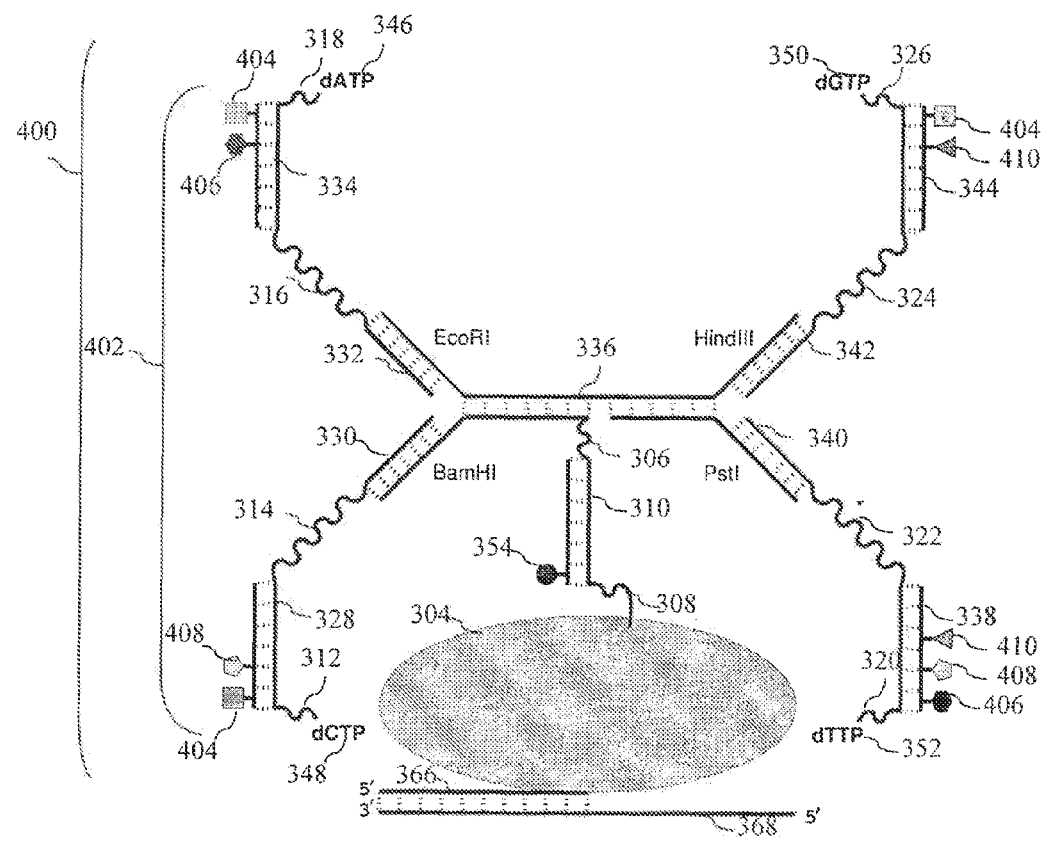

A variant of probe 300 is shown in FIG. 2D. Probe 400 is identical to probe 300, except that probe 400 includes a molecular linker 402, wherein multiple types of tags associated with each chemical moiety 346, 348, 350, 352, instead of a single tag. For example, chemical moiety 346 is associated with tags 404, 406, chemical moiety 348 is associated with tags 404, 408, chemical moiety 350 is associated with tags 404, 410, and chemical moiety 352 is associated with tags 406, 408, 410. By using several tags, corrections can be made to the signal emitted upon pairing of a chemical moiety with its complementary base in the target nucleic acid strand. For example, if the tag is an acceptor fluorophore, probe 400 permits detection and in some examples correction of fluorophore bleaching, or loss of one or more of the molecular linker branches. The probe 400 is shown bound to a primer 366, which is hybridized to a target nucleic acid molecule 368. However, the primer 366 and the target nucleic acid molecule 368 are not part of the probe 400.

In examples where the chemical moieties shown in FIGS. 1A-1C and 2A-2D are nucleotide analogs, the nucleotide analogs can be attached to the molecular linker by the base, at the 3' hydroxyl of the sugar, or at a phosphate (such as the α, β, or γ phosphate) or to any point on a nucleotide that does not interfere with specific binding to the active site of a polymerizing agent or complementary base pairing. The chemical moieties shown in FIGS. 1A-1C and 2A-2D can be different chemical moieties (as shown in FIGS. 1A-1C and 2A-2D), or can be the same chemical moieties (in which case nanoprobes with each type of chemical moiety could be included in the sequencing reaction). In particular examples, the tag associated with the polymerizing agents shown in FIGS. 1A-1C and 2A-2D is a donor fluorophore, and the tag associated with each chemical moiety includes an acceptor fluorophore. For example, if multiple types of chemical moieties are on the same probe, each chemical moiety can be associated with a unique acceptor fluorophore or combinations of fluorophores.

Generation of Nanoprobes

Many methods are available for generating the disclosed nanoprobes. For example, methods of attaching a tag to another molecule are known. In addition, methods of generating DNA-PEG structures are known. Although particular methods are provided herein, the disclosure is not limited to these methods.

DNA/PEG Synthesis and Attachments

In examples where the molecular linker includes one or more DNA molecular rods and one or more PEG tethers, the following methods can be used. DNA of any desired sequence can be obtained from a variety of commercial sources (such as Invitrogen, Synthegen, Sigma). The sequence of the DNA can be generated using the NANEV program, which employs "evolutionary methods for the design of nucleic acid nanostructures" (Goodman et al., *BioTechniques*, 38:548-50, 2005). This program can be used to design DNA sequences in a nanoprobe so that only the desired structure forms by hybridization. In particular examples a PEG tether is incorporated as a standard phosphoramidite 'spacer' anywhere within the molecular linker. It is also possible to introduce an amino group anywhere in the DNA sequence.

By appropriate use of DNA-DNA hybridization, a nanoprobe can be constructed using only one amino group per DNA/PEG linker. This allows the amino group to be used to attach a fluorophore or protein on the nanoprobe, for example as shown in FIG. 1A.

In one example a DNA-PEG-$NH_2$-dNTP is purified away from DNA-PEG-$NH_2$ using beads or another substrate to which a polymerase is attached. DNA-PEG-$NH_2$-dNTP will bind to the polymerase, while DNA-PEG-$NH_2$ will not.

Attachment of Tags to Chemical Moieties

A tag can be attached to a chemical moiety. For example, if the chemical moiety is a nucleotide analog, the tag can be attached to the base, sugar, α, β, or γ phosphate.

Attachment of Molecular Linker to Chemical Moieties

A chemical moiety can be attached to a molecular linker. For example, if the chemical moiety is a nucleotide analog, the molecular linker can be attached to the base, sugar (for example at the 3' hydroxyl of the sugar), α, β, or γ phosphate. Ideally, such attachment does not interfere with the ability of the chemical moiety to bind to the active site of the polymerizing agent or the ability to pair with a complementary nucleotide base. Methods of attaching a chemical moiety to a molecular linker are known in the art, and the disclosure is not limited to particular methods. For example, to attach the molecular linker to γ phosphate, the 5'-Amino-Modifier C6 TFA, can be used (available from Synthegen, Houston, Tex.; and IDT, Coralville, Iowa). Other methods that can be used to attach a nucleotide analog to a linker are described in U.S. Pat. No. 6,936,702 (herein incorporated by reference).

Attachment of Molecular Linker to Polymerizing Agent

In one example, one or more molecular linkers are attached to the polymerizing agent using the Tus protein to bind to a ter DNA site. For example, the Tus protein can be fused to the polymerizing agent using standard cloning techniques. Part of the molecular linker can include a ter DNA site, which will specifically bind to the Tus protein. The Tuster bond dissociation constant is $10^{-13}$ M (Neylon et al., *Microbiol. Mol. Biol. Rev.* 69:501-26, 2005).

Protein Linkers

In particular examples, the molecular linkers are composed of flexible protein chains, such as ser-gly. For example, a polymerizing agent can be extended to have flexible loops that form the molecular linkers. The chains loop back to continue the polymerase. The chemical moieties (such as dNTPs) can be added enzymatically, for example by attachment to an amino acid such as lysine or cysteine. The polymerase recognizes the particular molecular linker and attaches the appropriate base. Attachment can be, for example, on a regular dNTP if the result is non-hydrolyzable. In one example, the polymerase and the flexible molecular linker are expressed on the surface of a phage that carries the gene for the modified polymerase. A particular dNTP can be attached to a solid support, such as a column, for example on the 3' end. The phage expressing the modified polymerase is contacted with the solid support under conditions that permit binding of the polymerase to the dNTP. This permits selection of phage that express the modified polymerase. The modified polymerase can further include a donor fluorophore such as GFP, YFP, RFP, CFP and aequorin.

Methods of Sequencing a Target Nucleic Acid Molecule

The present disclosure provides methods of sequencing a target nucleic acid molecule, such as two or more target nucleic acid molecules simultaneously. Sequencing can be performed in vitro, ex vivo, in situ (for example using a biological sample obtained from a subject), or in vivo (for example by sequencing within a cell). In particular examples, the target nucleic acid strand includes one or more mutations associated with disease.

In particular examples, the target nucleic acid molecule is obtained from a subject. For example, the target nucleic acid molecule can be present in a biological sample obtained from a subject. In other examples, the target nucleic acid molecule is present in a subject, and exposing the template nucleic acid molecule to an oligonucleotide primer and the probe includes introduction of an oligonucleotide primer and the probe to a cell of the subject.

In particular examples, the method of determining the nucleic acid sequence of a target nucleic acid molecule includes exposing the target nucleic acid molecule to one or more of the probes disclosed herein, in the presence of an oligonucleotide primer and a mixture of hydrolyzable nucleotides. The hydrolyzable nucleotides are capable of being incorporated into an elongating nucleic acid molecule by pairing with a complementary nucleotide in the target nucleic acid molecule, and replacing the chemical moiety that reversibly binds to the complementary nucleotide on the target nucleic acid molecule. When the hydrolyzable nucleotide replaces the chemical moiety this steps the polymerizing agent forward one base. Since the chemical moieties are not permanently incorporated into the elongating complementary strand, they will eventually diffuse out of the active site of the polymerizing enzyme. The emission of a sequence of signals is detected, wherein the emission of a characteristic signal indicates pairing of the chemical moiety on the linker with its complementary nucleotide. Such a characteristic signal can also indicate which hydrolyzable nucleotide will be incorporated next into the elongating nucleic acid molecule that is complementary to the target nucleic acid molecule. In particular examples, the emission of a sequence of signals is converted into a nucleic acid sequence. In some examples, the emission of a sequence of signals is generated by luminescence resonance energy transfer (LRET) or Förster resonance energy transfer (FRET). In particular examples, the sequence of signals are detected with a charge-coupled device (CCD) camera and converted into the nucleic acid sequence. The sequence of signals can also be stored in a computer readable medium. Because the chemical moieties are not removed from the linker, the probe can be used again.

This method therefore solves the problem of incorporating fluorescently labeled nucleotides into an elongating complementary nucleic acid molecule, because the non-labeled hydrolyzable nucleotides are the only ones incorporated into the elongating strand. The resulting complementary nucleic acid molecule contains normal nucleotides.

In particular examples, the polymerizing agent is associated with a tag, and each of the chemical moieties is also associated with a tag that identifies a particular chemical moiety carried by the linker, wherein interaction of the tag associated with the polymerizing agent with the tag associated with the chemical moiety induces emission of the characteristic signal that indicates pairing of the chemical moiety with its complementary nucleotide. As described above, the tags can either be directly attached to the polymerizing agent and the chemical moieties, or indirectly associated with, for example present on, a molecular linker in sufficient proximity to the polymerizing agent or chemical moiety.

In some examples, the tag associated with the polymerizing agent includes a donor fluorophore and the tag that identifies a particular chemical moiety includes one or more acceptor fluorophores. Sufficient interaction of the polymerizing agent and the chemical moiety, for example the presence of the chemical moiety in the active site in the polymerizing agent and pairing of the chemical moiety with the complementary nucleotide on the target nucleic acid strand, brings the acceptor fluorophore into a proximity with a donor fluorophore to permit excitation of the acceptor fluorophore by the donor fluorophore. In such examples, detecting the signal can include detecting a fluorescent signal emitted from the acceptor fluorophore (such as an increase in fluorescence), or detecting a fluorescent signal emitted from the donor fluorophore (such as a decrease in fluorescence). In a specific example, the donor fluorophore is GFP, and the acceptor fluorophores are BODIPY, fluorescein, rhodamine green, Oregon green, or derivatives thereof. In another specific example, the donor fluorophore is Alexa Fluor 430, and the acceptor fluorophores are Alexa Fluors 546, 568, 594, and 647.

In some examples where one of the tags is a donor fluorophore, the method can further include exciting the donor fluorophore to emit an excitation signal which stimulates the one or more acceptor fluorophores to emit the characteristic signal that indicates pairing of the chemical moiety on the linker with its complementary nucleotide. For example, the donor can be excited, for example using electromagnetic radiation, such as a coherent beam of light provided by a laser which emits electromagnetic radiation of a particular wavelength, or light within a narrow range of wavelengths. In other examples, the donor is excited by a luminescent molecule (such as aequorin). In some examples, the donor is continually excited. However, not all donor fluorophores will require excitation by an external source. For example, chemiluminescent donor molecules do not require excitation by an external source. Ideally, the source of excitation of the donor fluorophore does not significantly excite the acceptor fluorophores.

The emission of the characteristic signal that indicates pairing of a particular chemical moiety (such as a nonhydrolyzable A, C, G, or T analog) on the molecular linker with its complementary nucleotide can be converted into a nucleic acid sequence. The series of emission signals, for example emitted in a microscope field as each chemical moiety is paired with its complementary nucleotide, is captured. For example, the emission signal can be collected with a microscope objective lens and a complete emission spectrum for each tag associated with a chemical moiety is generated by a spectrophotometer. The complete emission spectrum is captured by a detection device, such as CCD-camera, for each tag associated with a chemical moiety as each chemical moiety is paired with its complementary nucleotide in the microscope field of view. The CCD camera collects the emission spectrum and converts the spectrum into a set of charges. The charges for each chemical moiety pairing can be recorded by a computer, for converting the sequence of emission spectra into a nucleic acid sequence for each nucleic acid in the microscope field of view using an algorithm, such as a least-squares fit between the signal spectrum and the spectrum for the tag on each class of chemical moieties.

Although many different algorithms can be used to convert the emission spectra into a nucleic acid sequence, this specific example illustrates one approach. Four fluorescent spectra (Anm, Cnm, Gnm and T/Unm) are generated from macroscopic measurements. From the sample, an unknown noisy spectrum (Snm) is generated. The unknown spectrum is assumed to be the sum of the four known spectra with only four weights, a, c, g and t/u, representing the relative proportions of the nonhydrolyzable analogs. So at 520 nm through 523 nm, this results in five equations:

$$A520*a+C520*c+G520*g+T520*t=S520$$

$$A521*a+C521*c+G521*g+T521*t=S521$$

$$A522*a+C522*c+G522*g+T522*t=S522$$

$$A523*a+C523*c+G523*g+T523*t=S523$$

$$A524*a+C524*c+G524*g+T524*t=S524$$

Filling in the known values, such as for example A520, the unknown values a, c, g, and t/u are solved for by using a least squares linear regression.

In this particular example, the donor fluorophore associated with the polymerizing agent is GFP H9-40, and the chemical moieties are associated with acceptor fluorophores as follows: nonhydrolyzable A is labeled with BODIPY; nonhydrolyzable T is labeled with fluorescein; nonhydrolyzable C is labeled with rhodamine; nonhydrolyzable G is labeled with Oregon green. In another example, the donor fluorophore associated with the polymerase is H9-40, and the chemical moieties are associated with acceptor fluorophores as follows: nonhydrolyzable A is labeled with tetramethylrhodamine; nonhydrolyzable T/U is labeled with naphthofluorescein; nonhydrolyzable C is labeled with lissamine; nonhydrolyzable G is labeled with Texas Red. The emission spectrum of each of the acceptor fluorophores is monitored, and the spectrum of each of the fluorophores can be distinguished from each other, so that the pairing of each different type of chemical moiety with its complementary base can be detected.

The process of determining the relative proportions of the unknown tags is known in the art as 'linear unmixing' (Dickinson et al., *Biotechniques* 31:1272, 1274-6, 1278, 2001). An individual nanoprobe will give predominantly a single nucleotide sequence, while a collection of nanoprobes can give a mixture of nucleotide sequences. If the collection of nanoprobes are synchronized for a period of time or by stepping them along the sequence by adding only one hydrolyzable nucleotide at a time (as in a flow cell) then the collection will substantially report a single sequence. The relative proportions of bases in a sequence can be presented by the sequence logo technique (Schneider and Stephens, *Nucleic Acids Res.* 18:6097-100, 1990).

In particular examples, one or more components of the sequencing reaction are attached or fixed to a substrate, such as a glass, plastic, or metal substrate. For example, the probe, target nucleic acid, or primer can be fixed to a substrate. As described above, the probe can be attached to the substrate via the polymerizing agent. Nucleic acid molecules (such as the target nucleic acid or primer) can be attached to the substrate at the 5' end, the 3' end, or internally.

The method can include performing a plurality of sequencing reactions substantially simultaneously, and detecting the sequence of signals from the plurality of sequencing reactions. For example, a plurality of polymerizing agents, template nucleic acid molecules, or oligonucleotide primers can be fixed directly or indirectly to the substrate in a predetermined pattern. Detecting the sequence of signals can include correlating the signal with a nucleic acid molecule corresponding to a predetermined position within that pattern. The polymerizing agents, template nucleic acid molecules, or oligonucleotide primers can be fixed to the substrate in the predetermined pattern in channels which have been etched in an orderly array, by micropipetting droplets onto a substrate.

In some examples, the levels of nucleotides present in the sequencing reaction are controlled. For example, the probe is incubated with the primer and target nucleic acid molecule in the absence of added hydrolyzable nucleotides. The signal generated will indicate the nucleotide exposed on the target nucleic acid molecule, and thus the next nucleotide to be added. That nucleotide is then added, to step the probe forward by one or more positions. The nucleotide is removed (for example by washing), and the cycle is repeated.

FIG. 1B provides a particular example of how the disclosed probes can be used to sequence a nucleic acid molecule. One skilled in the art will appreciate that any of the disclosed probes can be substituted for probe 39. The method can include contacting a target nucleic acid sequence 40 with an oligonucleotide primer 42 and probe 39 (or any other probe shown herein, such as those shown in FIGS. 1A-B and 2A-D), in the presence of a mixture of non-labeled hydrolyzable nucleotides 46, 48, 50, 52 (such as dATP, dCTP, dGTP, and dTTP; or NTPs for an RNA polymerase). In the absence of a nucleic acid molecule to be sequenced 40 (not part of the nanoprobe) there is little detectable signal. When the polymerizing agent 12 is bound to a target nucleic acid sequence 40 at a primer 42, a base 44 (herein "T") is exposed on the target strand 40. The molecular linkers 14, 16, 18, 20 will move by Brownian motion, allowing the chemical moieties 22, 24, 26, 28 at the ends to approach and pair to the exposed base 44 on the target nucleic acid molecule 40 in the active site of the polymerizing agent 12. The chemical moieties 22, 24, 26, 28 at the ends of the molecular linkers 14, 16, 18, 20 compete for binding to base 44, but only one of the four chemical moieties (in this case 26) will be complementary to the exposed base 44. When an incorrect pairing occurs by the non-complementary chemical moieties (in this case 22, 24, 28), the chemical moiety (in this case 22, 24, or 28) will quickly dissociate. However, when a correct pairing occurs (in this example complementary chemical moiety 26), the correct chemical moiety will dwell for a substantial time in the active site of the polymerizing agent 12 and pair with the complementary base 44. During this time, the corresponding tag 36 (such as an acceptor fluorophore) on the complementary chemical moiety 26 will be in sufficient proximity to tag 30 (such as an donor fluorophore) associated with the polymerizing agent 12 for tag 30 to interact with tag 36, thereby producing a characteristic signal (such as acceptor emission signal) for that chemical moiety 26. Each of the tags 32, 34, 36, 38 produces a distinguishable emission signal. All of the chemical moieties 22, 24, 26, 28, will diffuse in and out of the active site, but the tag 36 associated with the chemical moiety 26 that is complementary to exposed base 44 will dominate the signal because it occupies the active site the longest, and can properly pair with the complementary base 44. Since the chemical moieties 22, 24, 26, 28, cannot be added to the elongating nucleic acid chain 42, the chain will not elongate until the chemical moiety in the active site of the polymerizing agent is replaced by a non-labeled hydrolyzable nucleotide (in this case 46). Thus the detectable signal indicates the next non-labeled hydrolyzable nucleotide (in this case 46) that will be incorporated into the elongating complementary strand 42. The appropriate hydrolyzable nucleotide 46 will eventually be incorporated into the elongating complementary strand 42, and the polymerizing agent 12 will step forward one position. This exposes the next complementary base on the target nucleic acid 40 and the cycle is repeated. The varying emission signals correspond to the target nucleotide sequence. During the stepping process in which the hydrolyzable nucleotide 46 is incorporated, only donor signal will be emitted.

In particular examples, the polymerizing agent 12 is attached to a substrate, such as a microscope slide (for example by a linker). The substrate can be mounted onto a microscope stage. In particular example, the sequencing reaction takes place in an aqueous environment, which can be sealed to prevent desiccation, for example by covering with a glass cover slip. In such examples, the nucleic acid to be sequenced 40 has an annealed oligonucleotide primer 42, and is bound by the anchored polymerizing agent 12. To start the sequencing reaction, a mixture of non-labeled hydrolyzable nucleotides 44, 46, 48, 50 is added along with the nanoprobes. The sequencing reaction will proceed as described above. Because all of the necessary components for sequencing are supplied and available at all times, no external pumping devices or reservoirs are required.

Therefore, the method allows for the sequencing of nucleic acids by monitoring the pairing of a chemical moiety that is reversibly bound to its complementary base on the target nucleic acid molecule on the molecular level, instead of sequencing by monitoring macromolecular events, such as a pattern on an electrophoresis gel, whose signal is representative of a large population of nucleic acid molecules. Using this method in combination with a large field of view, it is possible that 1000 or more DNA molecules could be sequenced simultaneously, at sequencing speeds of up to 750 base pairs per second, which is the rate of a fast DNA polymerase (Watson et al., *Molecular Biology of the Gene*, 4$^{th}$ *Edition*, The Benjamin/Cummings Publishing Co., Inc., Menlo Park, Calif., 1987, page 110). Each DNA molecule to be copied/sequenced, and its associated probe, can correspond to a particular portion of the field of view in which the polymerizing agent-mediated reaction is occurring.

Altering the Rate of Sequencing

In particular examples, the rate of nucleic acid sequencing is controlled. For example, the sequencing reaction can be performed at low temperatures, such as 0-30° C., for example 4° C., or room temperature (such as 20-25° C.) to decrease the rate of sequencing. At these lower temperatures, the polymerizing agent can be one that is able to function properly at lower temperatures. This temperature range allows for a more narrow spectral line and hence higher coding complexity. The lower temperature will sharpen the spectrum, allowing more distinct spectra to be read. Freezing is avoided, as it can interfere with the polymerization reaction. In another example, to decrease the rate of sequencing, the environment in which the sequencing reaction is performed is viscous, such as a viscosity of 9.95 cP in 20% Ficol 70. In addition, mutant polymerases can be used to decrease the rate of sequencing, such as a polymerase containing one or more mutations which slow the polymerase. The rate of sequencing can also be controlled by the concentration of free hydrolyzable nucleotides (such as dNTPs) present in the sequencing reaction; reducing the concentration of free dNTPs will reduce the rate of polymerization.

Compressed Sequences

The disclosed methods in particular examples provide a compressed sequence. That is, if the target sequence includes two or more of the same base in a row, the method may not detect the difference between the two or more same bases, thereby generating a compressed sequence. For example, the first 30 bases of an *E. coli* sequence:

(1)  agcttttcattctgactgcaacgggcaata  (SEQ ID NO: 1)

would be compressed by removing strings of similar bases:

(2)  agct cat ctgactgca cg ca ta  (SEQ ID NO: 2)

resulting in:

(3)  agctcatctgactgcacgcata  (SEQ ID NO: 2)

Such a compressed sequence is still usable because it is unique. For example, if RNA from *E. coli* is sequenced and this results in sequence 3 above, the location of the RNA can be determined by comparing sequence 3 above to a compressed version of the entire *E. coli* genome. When the entire human genome is sequenced, this method can be used to count individual mRNA molecules directly. The first step is to compress the entire human genomic sequence. Then, the NCBI Basic Local Alignment Search Tool (BLAST), or other program is used to search this compressed human genomic sequence using the results obtained from the sequencing methods of the present disclosure. This method does not require macroscopic handling for high-throughput analysis, and it is highly useful for studying gene expression.

However, methods are provided that permit detection of the complete, non-compressed sequence. For example, the polymerizing agent will only close on the active site when the correct chemical moiety (such as the correct base) is in the active site. The change in distance in parts of the polymerase can be measured, for example by FRET. This timing signal can be generated by including a tag on the polymerizing agent, wherein the movement of the tag is detected. For example, the polymerizing agent can include a donor and acceptor fluorophore pair, wherein opening and closing of the polymerizing agent results in a detectable signal due to the interaction of the fluorophores (such as the excitation of the acceptor by the donor, and the resulting acceptor emission that can be detected). Detection of the timing signal indicates incorporation, so it is apparent that two bases have been added to the nascent DNA polymer even if the two bases are identical.

Another method that can be used to detect the complete, non-compressed sequence is to perform the sequencing reaction in a system that permits agents to be added and removed, such as a flow cell. For example, the probes can be attached to a surface (such as a bead), and the primer/target nucleic acid molecule added. The flow can provide any of the four hydrolyzable bases (such as dNTPs). As the chemical moiety pairs with the complementary base on the target nucleic acid molecule, the resulting signal will indicate the hydrolyzable base that needs to be added next. That hydrolyzable base is added to the sequencing reaction, and the probe will step forward one base. The hydrolyzable base is then removed, and the process repeated. In the population the probes will make an exponential transition to the next missing base and stop. Therefore, the population can be monitored over time. If there are two bases to be added, then the transition will be slower. That is, the number of added bases can be determined by measuring the half life of the transition.

In another example, the probes of the present disclosure are attached to a substrate, and are bound the target nucleic acid and its primer. In such an example, the probe will include the same tag associated with each of the chemical moieties (such as the same acceptor fluorophore or combination of acceptor fluorophores). The polymerizing agent is also associated with a tag (such as a donor fluorophore). The non-labeled hydrolyzable nucleotides can be added, for example one type at a time. In the absence of non-labeled hydrolyzable nucleotides the chemical moiety will persist in the active site, producing a detectable signal (such as an acceptor fluorophore emission). Then one of the non-labeled hydrolyzable nucleotides is added. If the incorrect non-labeled hydrolyzable nucleotide is added, it will not replace the chemical moiety, and therefore not significantly change the detectable signal. In contrast, if the correct non-labeled hydrolyzable nucleotide is added, it will replace the chemical moiety, and therefore significantly change the detectable signal (for example decrease acceptor emission or increase donor emission). Since the timing of the recovery is dependent on the number of non-labeled hydrolyzable nucleotide that are added to the elongating complementary strand, if two non-labeled hydrolyzable nucleotides are added it will take longer for the detectable signal to recover than when one non-labeled hydrolyzable nucleotide is added. Therefore, by cycling through the four non-labeled hydrolyzable nucleotides, a complete sequence can be obtained.

Yet another method that can be used to detect a complete, non-compressed sequence is to use a nanoprobe having a donor fluorophore (such as a second donor fluorophore attached to the polymerizing agent) that specifically activates an acceptor fluorophore different from the acceptor fluorophores on the chemical moieties on the nanoprobe. The nucleic acid to be sequenced is labeled on at least one nucleotide with an acceptor fluorophore (such as one excitable by the second donor fluorophore). As the nanoprobe steps along the nucleic acid molecule to be sequenced, the distance between the donor on the polymerase and the acceptor-labeled template nucleic acid molecule gives a varying signal. Thus if the nanoprobe steps over two identical bases, they can be distinguished because simultaneously the acceptor to donor signal varies.

Single base steps can be resolved physically (Greenleaf and Block, Science, 313:801, 2006). Such methods can be combined with the Medusa nanoprobes disclosed herein. Stepping along DNA can be detected by the 3.4 Å step (0.34 nm) and by the 34 or so degree rotation (10.6 bp per 360 degrees). The rotation can be amplified by putting a fluorescent detector on a molecular linker attached to the nucleic acid to be sequenced (such as DNA). As the DNA rotates, a 34 degree rotation moves a greater distance with a longer arm. The longer the arm, the larger the change. Either the polymerase (such as a Medusa sequencer provided herein) moves or the DNA does. A moving polymerase can be observed (using the methods of Greenleaf and Block, Science 313:801, 2006). A moving target nucleic acid molecule can be detected by labeling the target nucleic acid molecule (for example by binding a DNA-binding GFP fusion protein). As the labeled target nucleic acid molecule rotates, the label rotate, thereby permitting detection of the stepping. If the label is bound tightly to the target nucleic acid molecule such that when target nucleic acid molecule rotates the angle of polarized light changes, this permits detection of the polymerase moving relative to the target nucleic acid molecule. Rotation will change the number of photons from each position. The GFP-DNA-binding protein is bound so that polymerase can remove it to read past it—or through a nucleosome-like object (as has been observed for T7 RNA polymerase).

Another method that can be used to detect movement of a target nucleic acid molecule (such as a target DNA molecule) is to use a nanoprobe that binds either along the target nucleic acid molecule or around the target nucleic acid molecule. A polarized FRET signal will occur when it binds. The molecular linkers can be flexible or rigid. Rigid molecular linkers allow displacing the point of detection away from the DNA, increasing the lever molecular linker. Another example is to use a 'Molecular Beacon scissors DNA detector'. This is a rigid cross-shaped molecule in which two arms bind the target DNA molecule on opposite faces of the DNA. A flexible hinge in the center permits binding of the two molecular linkers to the DNA such that when the linkers come close together a FRET signal is produced and detected. This device does not generate significant detectable FRET signal when not bound to a target nucleic acid molecule such as DNA. When bound, FRET signals are detected and when a Medusa sequencer moves the DNA, it moves around the DNA producing a varying polarized signal.

Yet another method that can be used is to contact the DNA with a DNA-intercalating dye, such as ethidium bromide. The dipole will rotate when a polymerase passes by. Alternatively, pyrrolo dC can be incorporated into the DNA as an internal fluorescent label. As the DNA rotates, the signals from the pyrrolo dC will vary because the dipole absorbing and emitting polarization angle would change. This change in the dipole axis will result in a change in signal (for example from ethidium bromide or pyrrolo dC) that can be detected.

In Vivo Sequencing

In particular examples, one or more Medusa probes are introduced into a cell, thereby permitting sequencing inside a live cell. For example, the disclosed probes can be used to observe the sequences of mRNA as they are produced (for example if the probe includes a reverse transcriptase as the polymerizing agent). In a particular example, the method is used to diagnose a genetic disease or cancer.

Methods of introducing agents into a cell are known in the art. In one example, one or more Medusa probes are incorporated into a liposome, which is introduced into the cell using standard methods known in the art. In another example, the probes are injected directly into a cell, for example using the method of Sokol et al (*Proc. Natl. Acad. Sci. USA* 95:1153843, 1998). In particular examples, the cell is obtained from a mammalian subject, such as a human. For example, cells can be obtained from a biological sample of the subject, such as a blood sample (or fraction thereof) or a cheek swab.

The nucleotides present in the cell can be the ones incorporated into the growing complementary strand (the hydrolyzable nucleotides, such as dNTPs). The primer can also be introduced into the cell with the probe. In a particular example, the primer is attached to the polymerizing agent, for example via a molecular linker. In a particular example, the sequence of the primer is determined based on the target sequence. For example, if the goal is to determine if a particular mutation is present in the target sequence, the primer sequence can be used to direct the Medusa probe to that sequence. Alternatively, the primer can consist of universal bases so that it will bind any sequence. (for example see Berger et al., *Nucleic Acids Res.* 28:2911-4, 2000).

In particular examples, the alternative splicing variants on mature RNA are identified.

EXAMPLE 1

Tagged Polymerases

This example describes methods that can be used to generate polymerases containing at least one tag, such as a fluorophore or luminescent molecule, for example a donor fluorophore. Although particular fluorophores or luminescent molecules are described, one skilled in the art will appreciate that others tags can be attached to a polymerase using similar methods.

General Attachment of Tags

Tags can be attached to a polymerizing agent using standard recombinant technologies. In general, tags are placed at the N- or C-terminus of a polymerizing agent. However, the tag can also be attached to any amino acid within the polymerizing agent, for example an amino acid exposed to the surface of the protein. Ideally, attachment of the tag does not significantly interfere with the polymerizing activity of the polymerizing agent. For example, a fusion polymerizing agent protein will still have the ability to incorporate nucleotides onto an elongating nucleic acid molecule.

Methods for making fusion proteins are known in the art (for example see Sambrook et al., *Molecular Cloning, A Laboratory Manual*, Cold Spring Harbor Laboratory, Cold Spring Harbor, N.Y., Chapter 17, 1989). To prepare a Tag-polymerase recombinant fusion protein, vectors can be constructed which contain sequences encoding the tag and the polymerase. The sequences are ordered to generate the desired Tag-polymerase recombinant fusion protein. This vector is expressed in bacteria such as *E. coli*, and the protein purified. The method of purification can depend on the tag attached. For example if an affinity tag is also attached to the polymerizing agent, the bacterial lysate is applied to a column containing a resin having high affinity for the tag on the fusion protein. After applying the lysate and allowing the tagged-fusion protein to bind, unbound proteins are washed away, and the fusion protein is subsequently eluted.

Alternatively, the tag can be attached to the polymerizing agent using chemical methods. For example, if the tag is to be attached to a Cys residue, the tag can be attached to a polymerizing agent using a thiol-reactive compound such as maleimide.

Affinity Tags

In one example, an affinity tag is attached to a polymerizing agent, such as a GFP-polymerase protein, to aid in its purification and subsequent attachment to a substrate (see Example 7). Examples of affinity tags include histidine (His), streptavidin, S-tags, and glutathione-S-transferase (GST). Other tags known to those skilled in the art can also be used. Commercially available vectors contain one or multiple affinity tags. These vectors can be used directly, or if desired, the sequences encoding the tag can be amplified from the vectors using PCR, then ligated into a different vector such as a polymerizing agent-containing vectors described above.

The six or ten consecutive histidine (His) residue moiety has high affinity for metal ions. A His-6 or His-10 moiety can be attached to a polymerizing agent by using pET vectors (Novagen, Madison, Wis.). The generation of GFP-His (Park and Raines, *Protein Sci.* 6:2344-9, 1997) and protein-GFP-His recombinant proteins have described previously (Prescott et al., *FEBS Lett.* 411:97-101, 1997). The His-containing fusion proteins can be purified as described in Paborsky et al. (*Anal. Biochem.*, 234:60-5, 1996). Briefly, the protein of interest from a cell lysate is immobilized using affinity chromatography on $Ni^{2+}$-NTA-Agarose (QIAGEN, Valencia, Calif.). After washing away unbound proteins, for example using a buffer containing 8 mM imidazole, 50 mM Tris HCl, pH 7.5, 150 mM NaCl, the bound recombinant protein is eluted using the same buffer containing a higher concentration of imidazole, for example 100-500 mM.

The S-tag system is based on the interaction of the 15 amino acid S-tag peptide with the S-protein derived from pancreatic ribonuclease A. Several vectors for generating S-tag fusion proteins, as well as kits for the purification of S-tagged proteins, are available from Novagen (Madison, Wis.). For example vectors pET29a-c and pET30a-c can be used. The S-tag fusion protein is purified by incubating the cell lysate with S-protein agarose beads, which retain S-tag fusion proteins. After washing away unbound proteins, the fusion protein is released by incubation of the agarose beads with site-specific protease, which leaves behind the S-tag peptide.

The affinity tag streptavidin binds with very high affinity to D-biotin. Vectors for generating streptavidin-fusion proteins, and methods for purifying these proteins, are described in Santo and Cantor (*Biochem. Biophys. Res. Commun.* 176: 571-7, 1991, herein incorporated by reference). To purify the fusion protein, the cell lysate is applied to a 2-iminobiotin agarose column, (other biotin-containing columns may be used), and after washing away unbound proteins, the fusion protein is eluted, for example with 6 M urea, 50 mM ammonium acetate (pH 4.0).

The enzyme glutathione-S-transferase (GST) has high affinity for gluathione. Plasmid expression vectors containing GST (pGEX) are disclosed in U.S. Pat. No. 5,654,176 to Smith and in Sharrocks (Gene, 138:105-8, 1994). pGEX vectors are available from Amersham Pharmacia Biotech (Piscataway, N.J.). The cell lysate is incubated with glutathione-agarose beads and after washing, the fusion protein is eluted, for example, with 50 mM Tris-HCl (pH 8.0) containing 5 mM reduced glutathione. After purification of the GST-polymerizing agent fusion protein, the GST moiety can be released by specific proteolytic cleavage. If the GST-fusion protein is insoluble, it can be purified by affinity chromatography if the protein is solubilized in a solubilizing agent that does not disrupt binding to glutathione-agarose, such as 1% Triton X-100, 1% Tween 20, 10 mM dithiothreitol or 0.03% $NaDodSO_4$. Other methods used to solubilize GST-fusion proteins are described by Frangioni and Neel (*Anal Biochem.* 210:179-87, 1993).

Recombinant GFP-Polymerase

Green fluorescent protein (GFP) includes a chromophore formed by amino acids in the center of the GFP. Wild-type GFP is excited at 393 nm or 476 nm to produce an emission at 508 nm. GFP mutants have alternative excitation and emission spectra. GFP mutant H9-40 has only a single absorption at 398 nm and emits at 511 nm. A red-shifted GFP mutant RSGFP4 (Delagrave et al., *Biotechnology* 13:1514, 1995) has an excitation at 490 nm and emission at 505 nm. The blue-shifted GFP mutant BFP5 absorbs at 385 nm and emits at 450 nm (Mitra et al., *Gene*, 173:13-7, 1996).

A polymerizing agent can be attached to GFP to generate a fusion protein, such as GFP-polymerase, by recombinant techniques known to those skilled in the art. Plasmids containing the wild-type or mutant GFP gene sequences and a multiple cloning site (MCS) into which the polymerase sequence can be inserted (such as pGFP), are available from Clontech (Palo Alto, Calif.).

Briefly, both the polymerase DNA and the GFP plasmid are digested with the appropriate restriction enzyme(s) which allow for the insertion of the polymerase into the MCS of the GFP plasmid in the sense orientation. The resulting fragments are ligated and expressed in bacteria, such as *E. coli*. The expressed recombinant GFP-polymerase is then purified using methods known by those skilled in the art. The GFP can be placed at the N- or C-terminus of the polymerase, or anywhere in between (such as an exposed Cys residue). Ideally, GFP-polymerases retain their polymerizing activity, and the fluorescent properties of the GFP.

Recombinant GFP-Aequorin-Polymerase

Recombinant GFP-aequorin-polymerase can be generated using methods known to those skilled in the art, for example the method disclosed by Baubet et al. (*Proc. Natl. Acad. Sci. USA* 97:7260-5, 2000, herein incorporated by reference).

Briefly, aequorin cDNA (for example Genbank Accession No. L29571), polymerase DNA, and a GFP plasmid are digested with the appropriate restriction enzyme(s) which allow for the insertion of the aequorin and polymerase into the MCS of a GFP plasmid in the sense orientation. The resulting fragments are ligated and expressed in bacteria, such as *E. coli*. The expressed recombinant GFP-aequorin-polymerase is then purified as described above. Affinity tags can also be added.

The ordering of the GFP, aequorin, and polymerase sequences can be optimized. The resulting GFP-aequorin-polymerases are tested to determine which has the optimal properties for sequencing. Such properties can include: ease of protein purification, amount of protein produced, amount of chemiluminescent signal emitted, amount of fluorescent signal emitted after excitation, minimal alteration of the fluorescent properties of the GFP and aequorin, and amount of polymerase activity.

Attachment of Fluorophores to a Polymerase

As an alternative to generating a GFP-polymerase fusion protein, other fluorophores can be used. In particular examples, fluorescently labeled polymerizing agents have a high fluorescence yield and retain the biological activity of the polymerizing agent, primarily the ability to synthesize a complementary strand of a nucleic acid molecule. The polymerizing agent can therefore have a less-than-maximal fluorescence yield to preserve the function of the polymerizing agent. Methods for labeling proteins with reactive dyes are well known to those well skilled in the art. In addition, the manufacturers of such fluorescent dyes, such as Molecular Probes (Eugene, Oreg.), provide instructions for carrying out such reactions. Following conjugation of one or more fluorophores to the polymerizing agent, unconjugated dye can be removed, for example by gel filtration, dialysis or a combinations thereof.

For example, amine-reactive fluorophores can be attached to a polymerizing agent. Examples of amine-reactive probes that can be used include, but are not limited to: fluorescein, BODIPY, rhodamine, Texas Red and their derivatives. Such dyes will attach to lysine residues within the polymerase, as well as to the free amine at the N-terminus. Reaction of amine-reactive fluorophores usually proceeds at pH values in the range of pH 7-10.

Alternatively, thiol-reactive probes can be used to generate a fluorescently-labeled polymerase. In proteins, thiol groups are present in cysteine residues. Reaction of fluors with thiols usually proceeds rapidly at or below room temperature in the physiological pH range (pH 6.5-8.0) to yield chemically stable thioesters. Examples of thiol-reactive probes that can be used include, but are not limited to: fluorescein, BODIPY, cumarin, rhodamine, Texas Red and their derivatives.

Other functional groups on the protein including alcohols (serine, threonine, and tyrosine residues), carboxylic acids and glutamine, can be used to conjugate other fluorescent probes to the polymerase.

Another fluorophore which can be attached to the polymerase is 4-[N-[(iodoacetoxy)ethyl]-N-methylamino]-7-nitrobenz-2-oxa-1,3-diazole (IANBD), as described by Allen and Benkovic (*Biochemistry*, 1989, 28:9586).

EXAMPLE 2

Tagged Chemical Moieties

This example describes how to attach one or more tags to a chemical moiety, such as a nonhydrolyzable nucleotide analog (for example a dNMP or dNDP). In addition, one skilled in the art will recognize that commercially available tagged chemical moieties can be used in the probes of the present disclosure.

Tags, such as one or more acceptor fluorophores, can be attached to any part of the chemical moiety. For example, if the chemical moiety is a nucleotide analog, the tag can be directly or indirectly attached to a base, sugar, or phosphate (such as an α, β, or γ-phosphate). Ideally, such attachment does not interfere with the ability of the chemical moiety to be reversibly bound to the template strand, and to pair with a complementary nucleotide in the target nucleic acid strand. In addition, ideally the tag is capable of being attached to the chemical moiety to provide a detectable signal.

In one example a tag, such as an acceptor fluorophore, is attached indirectly to the chemical moiety by a linker molecule. For example, a streptavidin linkage can be used. The linkage can be peptidase sensitive, allowing the tag to be released after the emission signal is detected as a result of pairing between the chemical moiety and its complementary base on the target nucleic acid strand. U.S. Pat. Nos. 5,047,519 and 5,151,507 to Hobbs et al. (herein incorporated by reference) teach the use of linkers to separate a nucleotide from a fluorophore. Examples of linkers may include a straight-chained alkylene, $C_1$-$C_{20}$, optionally containing within the chain double bonds, triple bonds, aryl groups or heteroatoms such as N, O or S. Substituents on the diradical moiety can include $C_1$-$C_6$ alkyl, aryl, ester, ether, amine, amide or chloro groups.

Jena BioScience offers multiple different nucleotide analogs that are not hydrolyzable, such as dGMPCPP, dAMPCPP, dCMPCPP, TMPCPP, dGMPNPP, dAMPNPP, dCMP- NPP, and TMPNPP where C represents a $CH_2$ group and N represents an NH group instead of the oxygen between the alpha and beta phosphates.

In examples where the tag associated with each different type of chemical moiety (such as dAMP, dCMP, dGMP and dTMP) is a different donor fluorophore, ideally the frequency used to excite a donor fluorophore on the polymerizing agent does not significantly overlap the excitation spectra of the acceptor fluorophores. However, each chemical moiety should possess at least one acceptor fluorophore having an excitation spectrum which overlaps the emission spectrum of the donor fluorophore attached to the polymerizing agent, such that the emission from the donor fluorophore excites the acceptor fluorophore. In addition, each type of chemical moiety (such as dAMP, dCMP, dGMP and dTMP) will have a unique tag (or a unique combination of tags) attached, such that each type (such as dAMP, dCMP, dGMP and dTMP) will have a distinct emission signal (such as an emission spectrum) from the other types of (such as dAMP, dCMP, dGMP and dTMP). Hence a chemical moiety that is complementary to "A" will give a different emission signal from a chemical moiety that is complementary to "C", "G", or "T"; a chemical moiety that is complementary to "C" will give a different emission signal from a chemical moiety that is complementary to "T", "G", or "A"; a chemical moiety that is complementary to "G" will give a different emission signal from a chemical moiety that is complementary to "C", "A", or "T"; and a chemical moiety that is complementary to "T" will give a different emission signal from a chemical moiety that is complementary to "C", "G", or "A". In the case of RNA, U will be substituted for T in this example.

To help ensure that a tagged chemical moiety can pair with a complementary nucleotide on the target nucleic acid, the tagged chemical moiety can be tested, for example using a fluorescence spectrophotometer if the tag is an acceptor fluorophore.

A 5' fluorescein labeled oligonucleotide is synthesized that contains a high Tm hairpin such that the oligonucleotide will anneal to itself to form a dsDNA with a 4 base overhang (Lyakhov et al., *Nucl. Acid Res.* 29: 4892-4900, 2001). A hairpin oligonucleotide allows exactly equimolar amounts of the top and bottom strands of the DNA and it does not require any annealing preparation step. A polymerase can fill in the overhang and the next base to be added is dTTP. In one version of this oligonucleotide the 3' end has a normal dC with a hydroxyl terminus that can be extended by one base using dTTP conjugated to Cy3. By filling in, the fluorescein is close to the Cy3 and FRET is measured between the two fluorophores using a fluorescence spectrophotometer. This demonstrates that the polymerase can bind to the DNA and polymerize under the given conditions. Another 5' fluorescein labeled oligonucleotide is synthesized that terminates in a dideoxy C (IDT, Coralville, Iowa). Fill in reaction conditions are set up as with the first oligonucleotide. When the polymerase is present FRET is observed between the 5' fluorescein and the dTTP-Cy3 which cannot be covalently attached to the dideoxy terminated oligonucleotide. Without the polymerase, no FRET is observed, demonstrating that the observed FRET (when the polymerase is present) is caused by the polymerase holding the Cy3-dTTP to its complementary base on the DNA hairpin. Under these same conditions dATP, dGTP, dCTP do not compete off the FRET but dTTP will, demonstrating a preference by the polymerase-hairpin complex for binding the correct next nucleotide but not the incorrect ones.

EXAMPLE 3

Attachment of a Linker to a Chemical Moiety

This example describes a method that can be used to attach a linker (such as PEG) to a chemical moiety (such as a nucleotide analog), such as the attachment of chemical moieties 22, 24, 26, 28 to molecular linkers 14, 16, 18, 20, respectively, shown in FIG. 1.

The end of a tether can include an amino group, which can be joined to the γ-phosphate of a non-hydrolyzable dNTP analog through a phosphoramidite linkage:

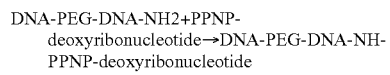

where PPNP means that the α, β-P-O-P bond is replaced by an imido group, P-N-P. The reaction uses 1 M 1-ethyl-3-(dimethylaminopropyl)carbodiimide (EDC), pH 6.5, 20° C. for 10-12 hours (Chatterji et al., *Methods Enzymol.* 274:456-78, 1996).

In addition, Jena BioScience offers dUTP with a tether attached on the γ phosphate that terminates in an amino group (γ-[(8-Aminooctyl)-imido]-dUTP).

EXAMPLE 4

Exemplary Molecular Linker

This example describes an exemplary molecular linker with a specific bend. This would allow the probe to have only very specific motions and it can remove the possibility of entanglement.

Figure 3:
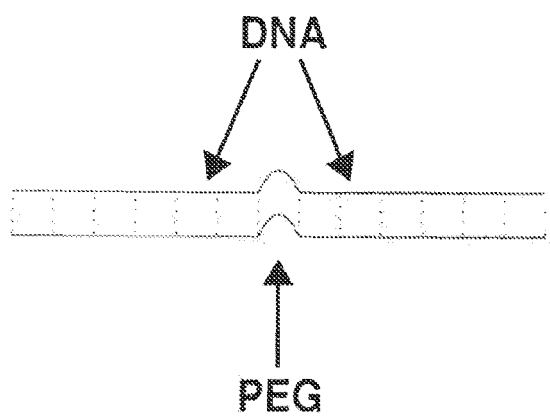
FIG. 3 is a schematic drawing illustrating a molecular linker composed of dsDNA and PEG.

In a particular example, a molecular linker includes a dsDNA with bulges, missing bases, or a nick within the dsDNA (for example near or at the middle). In another example, a dsDNA includes a short PEG tether at the same location on both strands (FIG. 3). Such a molecular linker can be used to further control the flexibility and rigidity of the molecular linker. For example, a bend can be designed with a range of particular angles to direct the bending of the molecular linker to guide the chemical moietie's tips to the active site of the polymerizing agent. In particular examples, both the 3' and 5' end of the dsDNA are attached to the polymerase, to avoid rotation.

EXAMPLE 5

Probe for Sequencing Nucleic Acid Molecules

This example describes a particular probe that can be used to sequence a target nucleic acid molecule. Although particular fluorophores, molecular linkers, and polymerases are described, one skilled in the art will appreciate that variations to these can be made, based on the teachings herein.

The design is based on FIG. 2C, but the method of attachment of the molecular linker to the polymerase is changed by removing the tether 306, dsDNA 310, and tether 308. dsDNA 336 is replaced by a continuous dsDNA, without any break, that contains a binding site (ter) for the Tus protein. The Tus protein is translationally fused to HIV-1 RT (for example using the methods described in Example 1).

The DNA sequences were designed using the NANEV program and checked to ensure that the restriction sites shown in FIG. 2C are unique. In addition, a MaeIII restriction site naturally appears in the ter sequence and this is unique in the probe. The Tus sequence used is the consensus bases from nine known Tus sites. Given the constraints that certain pairs of ssDNA sequences are complementary to each other and that some sequences contain the restriction sites shown in FIG. 2C, the NANEV program was used to evolve the structure.

NANEV uses single letter names for dsDNA strands. Lower case letters (a, c, g, t, e, h, b, p, m) represent a segment of ssDNA that is to be hybridized to the corresponding ssDNA labeled with an upper case letter (A, C, G, T, E, H, B, P, M). Each dsDNA branch is named by the corresponding non-hydrolyzable base (A, C, G, T) while the 'hub' parts are named by restriction enzymes that cut them (E, H, B, P, M). For example, for the branch 334 that has a non-hydrolyzable adenosine 346, one oligonucleotide is named 356-334-1a, and it is bound to fluorophore 356. 356-334-1a will anneal with 332-316-334-318-346-11E-2A.

The 14 dsDNA parts designed using NANEV are shown in Table 3:

TABLE 3

Sequences to generate nanoprobe

| # | name | Sequence | SEQ ID NO: |
|---|------|----------|------------|
| 1 | a | GGCCTCCGTCCTCGGCAGTA | 3 |
| 2 | A | TACTGGCGAGGACGGAGGCC | 4 |
| 3 | c | CGATAATGCCTGTCATGCAT | 5 |
| 4 | C | ATGCATGACAGGCATTATCG | 6 |
| 5 | g | GAACGTCTAGACTTATCGC | 7 |
| 6 | G | GCGATAAGTCTAGACGTTCC | 8 |
| 7 | t | CTCTCGCTCCGTGCCGTAAG | 9 |
| 8 | T | CTTACGGCACGGAGCGAGAG | 10 |
| 9 | eMh | CGCTCCTGAATTCGACGTACGCTATATATTTA GTATGTTGTAACTAAAGTCCAGCGCGAAGCT TAATGACT | 11 |
| 10 | pmb | ATTCAGTCTGCAGGAAGGCCGACTTTAGTTA CAACATACTAAATATATAGCCAGTAAGGGAT CCGATCTCG | 12 |
| 11 | E | GTACGTCGAATTCAGGAGCG | 13 |
| 12 | B | CGAGATCGGATCCCTTACTG | 14 |
| 13 | H | AGTCATTAAGCTTCGCGCTG | 15 |
| 14 | P | GGCCTTCCTGCAGACTGAAT | 16 |

Some of these 14 components are joined by PEG and linked to appropriate fluorophores to create ten oligonucleotides. The ten oligonucleotides can be synthesized commercially by IDT (Coralville, Iowa) or Midland (Midland, Tex.) as follows:

>356-334-1a:
(SEQ ID NO: 3)
[fluorophore-356]-GGCCTCCGTCCTCGGCAGTA,
where [fluorophore-356] is Rhodamine Red(TM)-X
(Absorbance Max: 574 nm, Emission Max: 594)
"GREEN"

>358-328-3c:
(SEQ ID NO: 5)
CGATAATGCCTGTCATGCAT-[fluorophore-358],
where [fluorophore-358] is Cy3(TM) (Absorbance
Max: 550 nm, Emission Max: 564) "BLUE"

>360-344-5g:
(SEQ ID NO: 7)
GGAACGTCTAGACTTATCGC-[fluorophore-360],
where (fluorophore-360] is Texas Red ®-X
(Absorbance Max: 598 nm, Emission Max: 617)
"YELLOW"

>362-338-7t:
(SEQ ID NO: 9)
[fluorophore-362]-CTCTCGCTCCGTGCCGTAAG,
where [fluorophore-362] is Cy5(TM) (Absorbance
Max: 648 nm, Emission Max: 668) "RED"

>332-316-334-318-NH2-11E-2A:
(SEQ ID NO: 17)
GTACGTCGAATTCAGGAGCG-[PEG18]-[PEG18]-[PEG18]-TACTG

CCGAGGACGGAGGCC-[PEG9]-NH2

>NH2-312-328-314-330-4C-12B:
(SEQ ID NO: 18)
NH2-[PEG9]-ATGCATGACAGGCATTATCG[PEG18]-[PEG18]-

[PEG18]-CGAGATCGGATCCCTTACTG

>NH2-326-344-324-342-6G-13H:
(SEQ ID NO: 19)
NH2-[PEG9]-GCGATAAGTCTAGACGTTCC-[PEG18]-[PEG18]-

[PEG18]-AGTCATTAAGCTTCGCGCTG

>340-322-338-320-NH2-14P-8T:
(SEQ ID NO: 20)
GGCCTTCCTGCAGACTGAAT-[PEG18]-[PEG18]-[PEG18]-CTTAC

GGCACGGAGCGAGAG-[PEG9]-NH2

>332-336-342-9eMh:
(SEQ ID NO: 21)
CGCTCCTGAATTCGACGTACGCTATATATTTAGTATGTTGTAACTAAAGT

CCAGCGCGAAGCTTAATGACT

>340-336-330-10pmb:
(SEQ ID NO: 22)
ATTCAGTCTGCAGGAAGGCCGACTTTAGTTACAACATACTAAATATATAG

CCAGTAAGGGATCCGATCTCG

Four non-hydrolyzable dNTPs are synthesized (for example by Jena Bioscience): dGMPCPP, dAMPCPP, dCMPCPP, and TMPCPP, where C represents a $CH_2$ group instead of the oxygen between the $\alpha$ and $\beta$ phosphates. Note that the older terminology TMPCPP means dTMPCPP that is, deoxyribo-TMPCPP. (Jena Bioscience can also provide dGMPNPP, dAMPNPP, dCMPNPP, and TMPNPP where N represents an NH group instead of the oxygen between the $\alpha$ and $\beta$ phosphates. Note that the older terminology TMPNPP means dTMPNPP that is, deoxyribo-TMPNPP.

Each non-hydrolyzable dNTP is covalently attached by its $\gamma$ phosphate to an amino group on the corresponding oligonucleotide branch using the following reaction protocol derived from Pierce Technical Resource TR0030.1 "Modify and label oligonucleotide 5'phosphate groups" except that the roles of label and oligonucleotide are reversed.

1. Dissolve the non-hydrolyzable dNTP in 10 μl reaction buffer. (The reaction buffer recommended by Pierce is "Reaction Buffer, such as phosphate buffered saline (PBS) with EDTA: 10 mM sodium phosphate, 0.15 M NaCl, 10 mM EDTA, pH 7.2. Avoid using PBS with >10 mM phosphate, which will interfere with the intended reaction. Other amine free and carboxylate-free buffers can be substituted, but avoid Tris, which contains a primary amine that will quench the reaction.")

2. Dissolve the oligonucleotide to a final concentration of 1 mM in 10 μl of 0.1 M Imidazole, pH 6.

3. Weigh 1.25 mg (6.52 micromol) of EDC (1-ethyl-3-[3-dimethylaminopropyl]carbodiimide hydrochloride, Pierce Product No. 22980.) into a microcentrifuge tube.

4. Add 7.5 μl of the prepared non-hydrolyzable dNTP to the tube containing the EDC and immediately add 5 μl of the oligonucleotide/imidazole solution.

5. Vortex tube until contents are completely dissolved, and then briefly centrifuge the tube to gather contents.

6. Add an additional 20 μl of 0.1 M imidazole, pH 6.

7. Incubate the reaction overnight at Room Temperature.

8. Separate the unreacted oligonucleotide from the reaction product on a 10% polyacrylamide gel.

It is also possible to purify the product by its ability to bind to a DNA polymerase. The unreacted nucleotides are first removed by using a size-exclusion column or dialysis. Then a column is created that has HIV-1 RT or another polymerase attached (for example HIV-1 RT with a histidine-6 tag bound to a nickel column). A template DNA and annealed primer DNA can be added. This polymerase column should retard the oligonucleotide to which is attached a nucleotide, compared to the unreacted oligonucleotide that does not have a tethered nucleotide. A description of the carbodiimide cross-linking reaction described above is given in Chatterji and Gopal (*Methods Enzymol.* 274:456-78, 1996). This protocol is performed separately for each oligonucleotide.

The oligonucleotide: is attached to:

```
332-316-334-318-NH2-11E-2A     (SEQ ID NO: 17)
non-hydrolyzable dAMPCPP

NH2-312-328-314-330-4C-12B     (SEQ ID NO: 18)
non-hydrolyzable dCMPCPP

NH2-326-344-324-342-6G-13H     (SEQ ID NO: 19)
non-hydrolyzable dGMPCPP 340-322-338-320-NH2-14P-8T     (SEQ ID NO: 20)
non-hydrolyzable TMPCPP
```

This creates the following structures:

```
>332-316-334-318-346-11E-2A:
                               (SEQ ID NO: 23)
GTACGTCGAATTCAGGAGCG-[PEG18]-[PEG18]-[PEG18]-TACTG

CCGAGGACGGAGGCC-[PEG9]-NH-POOH-O-POOH-CH2-POOHdeoxyadenosine

>340-322-338-320-352-14P-8T:
                               (SEQ ID NO: 24)
GGCCTTCCTGCAGACTGAAT-[PEG18]-[PEG18]-[PEG18]-CTTAC

GGCACGGAGCGAGAG-[PEG9]-NH-POOH-O-POOH-CH2-POOHdeoxythymidine
```

```
-continued
>350-326-344-324-342-6G-13H:
                               (SEQ ID NO: 25)
deoxyguanosine-POOH-CH2-POOH-O-POOH-NH-[PEG9]-GCGA

TAAGTCTAGACGTTCC-[PEG18]-[PEG18]-[PEG18]-AGTCATTAA

GCTTGGCGCTG

>348-312-328-314-330-4C-12B:
                               (SEQ ID NO: 26)
deoxycytidine-POOH-CH2-POOH-O-POOH-NH-[PEG9]-ATGCA

TGACAGGCATTATCG-[PEG18]-[PEG18]-[PEG18]-CGAGATCGGA

TCCCTTACTG
```

The 10 oligonucleotides: 332-316-334-318-346-11E-2A (SEQ ID NO: 23); 340-322-338-320-352-14P-8T (SEQ ID NO: 24); 350-326-344-324-342-6G-13H (SEQ ID NO: 25); 348-312-328-314-330-4C-12B (SEQ ID NO: 26); 356-334-1a (SEQ ID NO: 3); 358-328-3c (SEQ ID NO: 5); 360-344-5g (SEQ ID NO: 7); 362-338-7t (SEQ ID NO: 9); 332-336-342-9eMh (SEQ ID NO: 11); 340-336-330-10pmb (SEQ ID NO: 12); are then hybridized together to form the molecular linker 302 of the probe shown in FIG. 2C. The molecular linker 302 is then purified by gel electrophoresis, an exclusion column or sucrose gradient. The structure of the generated molecular linker 302 can be tested by digesting with the five restriction enzymes separately and in combinations and by observing the products on polyacrylamide gels.

The tus (termination utilization substance) gene from *E. coli* has been cloned in pBAD33tus (Henderson et al., *Mol. Genet. Genomics* 265:941-53, 2001, Guzman et al., *J. Bacterial* 77:4121-30, 1995). The HIV-1 RT p66 subunit has been cloned and modified to replace all solvent-accessible cysteine residues with serine residues (C38S and C280S) and to substitute a unique cysteine for the lysine at 287, K287C (Kensch et al., *J. Mol. Biol.* 301:1029-39, 2000). The unique cysteine at 287 is on the "thumb" of the polymerase, close to the active site of the polymerase, but far enough away so as not to interfere with DNA binding or the active site. There are only two cysteines in the Tus protein at CYS99 and CYS255 and they are both completely buried, (PDB 1ECR Kamada et al., *Nature* 383:598-603, 1996), so it is not necessary to engineer Tus to avoid exposed cysteines. Tus is cloned in a translational fusion with the mutated HIV-1 RT.

As seen in the three dimensional structures of HIV-1 RT (PDB entry 1RTD Huang et al., *Science* 282:1669-1675, 1998) and Tus bound to DNA (1 ECR Kamada et al., *Nature* 383:598-603, 1996) the N and C termini of both proteins are on their surfaces well away from the active sites, so fusion of the two proteins will not interfere with their structures or functions. The hydrophylic polypeptide that connects the two parts of the RecB protein (PDB entry 1 W36, Singleton et al., *Nature* 432:187-93, 2004) is used to connect Tus to HIV-1 RT to create Tus-HIV-1 RT.

Those skilled in the art will recognize that either Tus or HIV-1 RT protein can be placed at the N terminus of the fusion and that they can be interchanged. Those skilled in the art will also recognize that 6-histidine tags can be placed on either end of the construction to help isolation. A 6-histidine tag on the N terminus of Tus has little effect on binding, while a 6-histidine tag on the C terminus of HIV-1 has no known effect on polymerase activity.

The donor fluorophore is attached to the unique cysteine in Tus-HIV-1 RT by using the maleimide labeling reagent Fluorescein-5-Maleimide (Pierce, Rockford, Ill., using the manufacturer's instructions). This donor fluorophore forms FRET pairs with each of the four acceptor pairs described above. Those skilled in the art will also recognize that additional acceptor fluorophores can be added to the corresponding oligonucleotides to adjust for the relative signal strength, if desired. Those skilled in the art will recognize that many other possible combinations of fluorophores are possible.

The Tus-HIV-1 RT protein is added to the core to create the completed probe. The probe is then purified by gel electrophoresis, an exclusion column or sucrose gradient. The final probe structure is checked by digesting with the five restriction enzymes separately and in combinations and by observing the products on polyacrylamide gels.

In a second example, the reverse transcriptase is modified by directed mutagenesis of F227A to reduce its error frequency (Wisniewski et al., *J. Biol. Chem.* 274:28175-84, 1999). In a third example, the connection between Tus and HIV-1 RT is determined as it is for single chain Fv (scFv) linker sequences. The classical sequence used is $(Gly_4Ser)_3$, but phage display technology can be used to obtain other variations (Tang et al., *J. Biol. Chem.* 271:15682-6, 1996; Hennecke et al., *Protein Eng.* 11:405-10, 1998).

Those skilled in the art will recognize that many other design variations are possible for the nanoprobe of the present disclosure.

EXAMPLE 6

Coded Probe for Sequencing Nucleic Acid Molecules

This example describes a variant of the probe described in Examples 5, wherein multiple fluorophores are associated with each nonhydrolyzable nucleotide analog. Although particular combinations of fluorophores are described, one skilled in the art will appreciate that other combinations can be used. Such a probe permits detection of photobleaching of acceptor fluorophores associated with each chemical moiety, and in particular examples permits correction of such photobleaching.

If the chemical moieties on the probe are each only associated with a single acceptor fluorophore, and that acceptor fluorophore was lost by bleaching, no acceptor emission signal would be detected from that acceptor fluorophore. If there were no signal from this photobleached acceptor fluorophore, it would be difficult to discern whether the loss of signal was due to photobleaching, or whether a stretch of target sequence that simply does not have that base. By associating two or more tags with each chemical moiety, fluorophore bleaching can be detected and in some examples corrected.

The probe shown in FIG. 2D includes multiple tags 404, 406, 408, 410 associated with each of the chemical moieties 346, 348, 350, 352. The inclusion of multiple acceptor fluorophores permits the detection of a loss of the fluorophores by bleaching, or by loss of part of the molecular linker.

In FIG. 2D, different tags 354, 404, 406, 408, 410 form a code similar to a Hamming error correction code. If any one of these tags has been destroyed by photobleaching, the resulting signal will be distinct from that produced by an undamaged probe. For example, if donor 354 is destroyed, then no donor emission will be produced and none of the other fluorophores will be excited. Sequence data from such a probe can be ignored. The "A" arm of the probe has two acceptor fluorophores, 404 and 406. When a complementary T is on the target DNA in the polymerase binding site, both fluorophores will be excited by donor 354. This produces a unique spectrum compared to the other three arms. That is, A is associated with 404, 406; C is associated with 404, 408; G is associated with 404, 410 and T is associated with 406, 408, 410. If fluorophore 404 on rod 334 is photobleached, then the A arm will report a signal containing only the spectrum of 406. This differs from an undamaged A signal and from the signals produced by the other three arms. Therefore the recording computer can determine that the probe has been damaged and that signal reading from that probe should be terminated. Since the T arm 338 has three fluorophores, it is unlikely that both fluorophores 408 and 410 will have been destroyed simultaneously. So a signal containing only the spectrum from 406 is likely to be caused by binding of the A arm to the target nucleotide. The computer can therefore infer that the next base in the sequence is indeed an A before terminating reading. That is, the computer is able to perform an error detection and an error correction.

If fluorophore 406 on the rod 334 has been destroyed, then the received signal will consist of only the 404 spectrum. A spectrum of 404 could also be produced by bleaching of fluorophore 408 on rod 328 or by bleaching of fluorophore 410 on rod 344. Therefore the arm that has produced the 406 signal cannot be determined unambiguously. In this case the computer reading the DNA sequence can conclude that an error has been made but it will not be able to correct the error. At this time reading from the Medusa is terminated.

Destruction of fluorophores on rods 328 or 344 gives results similar to destruction of fluorophores on rod 334. In all of these cases if the common fluorophore 404 has been destroyed, then one error can be detected and that error can be corrected. If the other fluorophore that is not 404 (that is, fluorophores 406, 408, 410 on rods 334 328 344 respectively) has been destroyed then one error can be detected and no errors can be corrected. Once an error has been detected, and perhaps corrected, sequencing is terminated because a second error will give ambiguous results.

If any of the three fluorophores 406, 408, 410 on rod 338 have been photobleached then the remaining two fluorophores still give a unique signal. For example if fluorophore 406 has been destroyed then the signal when the T arm binds to an A on the target nucleotide will consist of the spectra from fluorophores 408 and 410. These spectra alone are not produced by an undamaged probe so one error can be detected and that error can be corrected. In this case, as with the other three arms, sequencing is terminated after the error correction because a second error will give ambiguous results.

Other coding schemes are possible for the probes disclosed herein, including schemes with more than four fluorophores. One skilled in the art can predict the number of errors that can be detected and corrected by various coding schemes. However the one shown in FIG. 2D only requires four fluorophores to implement. A basic probe such as that shown in FIG. 2C uses four fluorophores to produce full sequence data, but the redundant rearrangement of only four fluorophores allows for the construction of an error detecting and correcting probe. Because the probe design allows for the interchange of fluorophores, as shown in FIG. 2C where ssDNA 364 can be exchanged for ssDNA 334, once a basic non-coded probe has been constructed it is possible to create a coded probe as shown in FIG. 2D. The coded probe is constructed as in Example 5 except that oligonucleotides 356-334-1a (SEQ ID NO: 3), 358-328-3c (SEQ ID NO: 5), 360-344-5g (SEQ ID NO: 7), and 362-338-7t (SEQ ID NO: 9) are replaced by the following four oligonucleotides:

```
>404-406-334-1a
                                          (SEQ ID NO: 27)
[fluorophore-404]-[fluorophore-406]-GGCCTCCGTCCTCG

GCAGTA

"BLUE" "RED"
>404-408-328-3c
                                          (SEQ ID NO: 28)
CGATAATGCCTGTCATGCAT-[fluorophore-404]-

[fluorophore-408]

"BLUE" "YELLOW"

>404-410-344-5g
                                          (SEQ ID NO: 29)
GGAACGTCTAGACTTATCGC-[fluorophore-404]-

[fluorophore-410]

"BLUE" "GREEN"

>406-408-410-320-7t
                                          (SEQ ID NO: 30)
[fluorophore-406]-[fluorophore-408]-[fluorophore-

410]-CTCTCGCTCCGTGCCGTAAG
"RED" "YELLOW" "GREEN"
``` where [fluorophore-404] is Cy3® (Absorbance Max: 550 nm, Emission Max: 564) "BLUE" (corresponds to FIG. 2C fluorophore-358); [fluorophore-406] is Cy5® (Absorbance Max: 648 nm, Emission Max: 668) "RED" (corresponds to FIG. 2C fluorophore-362); [fluorophore-408] is Texas Red®-X (Absorbance Max: 598 nm, Emission Max: 617) "YELLOW" (corresponds to FIG. 2C fluorophore-360); [fluorophore-410] is Rhodamine Red™-X (Absorbance Max: 574 nm, Emission Max: 594) "GREEN" (corresponds to FIG. 2C fluorophore-356).

EXAMPLE 7

Attachment of a Probe or Nucleic Acid Molecule to a Substrate

This example describes methods that can be used to attach the tagged polymerizing agent generated in Example 1 (for example part of the probes of Examples 5 and 6), or a nucleic acid molecule, to a substrate, such as a microscope slide or gel matrix. During the sequencing reaction, the target nucleic acid molecule to be sequenced, the oligonucleotide primer, or the probe, can be attached to a substrate (for example in a microscope field of view).

Attachment of Nucleic Acids

Several methods for attaching nucleic acids (for example the target nucleic acid molecule to be sequenced or an oligonucleotide primer) to a substrate are available. Nucleic acid molecules can be attached to the substrate by their 5' or 3' end, or anywhere in between. For example, a 5' biotinylated primer can be synthesized (Beaucage, *Tetrahedron Letters* 22:1859-62, 1981; Caruthers, *Meth. Enzym.* 154:287-313, 1987), and affixed to a streptavidin coated substrate surface (Hultman, *Nucl. Acids Res.* 17:4937-46, 1989). In another example, the nucleic acid molecule can be dried on amino-propyl-silanized (APS) glass, as described by Ha et al. (*Proc. Natl. Acad. Sci. USA*. 93:6264-68, 1996, herein incorporated by reference). Methods for attaching the oligonucleotide primer to the substrate via a linker are disclosed in U.S. Pat. No. 5,302,509 to Cheeseman, herein incorporated by reference.

In yet other examples, a nucleic acid molecule is cross-linked to an unmodified substrate by conjugating an active silyl moiety onto the nucleic acid molecule (for example using the methods disclosed by Kumar et al. (*Nucleic Acids Res.* 28:e71, 2000). Briefly, silane is conjugated to a nucleic acid as follows. Mercaptosilane[(3-Mercaptopropyl)-trimethoxysilane] is diluted to 5 mM stock solution with a reaction buffer such as sodium acetate (30 mM, pH 4.3) or sodium citrate (30 mM, pH 4). For conjugation of 5'-thiol-labeled nucleotides with mercaptosilane, 1 nmol nucleotides are reacted with 5 nmol mercaptosilane in 20 µl of the same buffer for 10-120 min at room temperature. The reaction mixture is used directly or diluted with the reaction buffer to a desired concentration for immobilization on a substrate, such as a glass microscope slide. 5'-acrylic-labeled oligonucleotides are conjugated to mercaptosilane using an identical procedure.

The 5'-thiol-labeled nucleotides are conjugated with aminosilane[(3-aminopropyl)-trimethoxysilane] in dimethylsulfoxide (DMSO) in the presence of heterobifunctional linkers N-succinimidyl-3-(2-pyridyldithiol)-propionate (SPDP) or succinimidyl-6-(iodoacetyl-amino)-hexanoate (SIAX). Nucleotides (final concentration 5-50 µM) are combined with 2.5 nmol aminosilane (added from 5 mM solution in ethanol) and 2.5 nmol bifunctional reagents (added from 5 mM stock solution in DMSO) in 10 µl DMSO, and the reaction allowed to proceed for 1-2 hours at room temperature.

Acrylic-labeled oligonucleotides (50-500 pmol) are combined with 25 nmol acrylicsilane (γ-methacryloxy-propyl-trimethoxysilane) in 10 µl of 30 mM NaOAc, pH 4.3. Ammonium persulfate (10% in H2O) and N,N,N',N'-tetramethylethylenediamine (TEMED) are added to final concentration of 0.5 and 2%, respectively, and the mixture allowed to react for 30 minutes at room temperature.

After the conjugation reactions, the reaction mixture is referred to as silanized nucleic acid, and can be directly used for spotting onto a substrate. Silanized nucleic acids can be spotted on the glass slides manually (120 nl/spot) or with an automated arrayer (Genetic Microsystem, Woburn. USA) (1 nl/spot). Nucleic acids in aqueous solutions can be kept in a humidified chamber for 15 minutes at room temperature after spotting onto the glass slide, dried at 50° C. for five minutes, dipped into boiling water for 30 seconds to remove non-covalently bound nucleic acids, and dried with nitrogen before hybridization. Nucleotides in DMSO are left at room temperature for 15 minutes after spotting onto glass slides and dried at 50° C. for 10 minutes. These slides are sequentially washed with DMSO (3×2 min), ethanol (3×2 min) and boiling water (2 min) and dried with nitrogen for later use.

To hybridize a complementary nucleic acid molecule to the nucleic acid molecule attached to the substrate, such as an oligonucleotide primer, the nucleic acid molecule to be hybridized is diluted to between 20 nM and 1 µM in 5×SSC (750 mM NaCl, 125 mM sodium citrate, pH 7) with 0.1% Tween-20. Hybridization is done under coverslips in a humidifier at 37° C. for 30 minutes to overnight. Non-hybridized and non-specific nucleic acid molecules are removed by washing with 5×SSC containing 0.1% Tween-20 (3×1 min) followed by 1×SSC containing 0.1% Tween-20 (2×15 min).

If a longer nucleic acid molecule is to be hybridized, such as a sample nucleic acid molecule, hybridization can be carried out at 65° C. for four hours in 3×SSC with 0.1% SDS and 1 µg/µl yeast tRNA. The slides are then washed with 1×SSC containing 0.1% SDS (3×2 min) and 0.1×SSC containing 0.1% SDS (3×5 min) at room temperature.

After washing, the slides can be dried with nitrogen gas. If repeated hybridization on the same substrate is desired, the substrate is boiled in water for one minute then dried with nitrogen gas before proceeding to the next hybridization reaction.

To attach a nucleic acid by the 3' end, a terminal transferase can be used to "tail" the molecule.

Attachment of a Probe

The probes of the present disclosure can be attached or fixed to a substrate via the polymerizing agent. For example, a streptavidin-polymerase fusion protein can be generated (for example using the methods described in Example 1), and then affixed to a biotinylated substrate, for example as described by Mazzola and Fodor (*Biophys. J.* 68:1653-60, 1995) or Itakura et al. (*Biochem. Biophys. Res. Commun.* 196:1504-10, 1993).

Other methods of attaching the polymerizing agent to a substrate are well known to those skilled in the art. For example, the microscopic tip of an atomic force microscope may be used to chemically alter the surface of a substrate (Travis, *Science* 268:30-1, 1995). Alternatively, if the polymerizing agent contains 6-10 consecutive histidine residues, it will bind to a nickel-coated substrate. For example, Paborsky et al. (*Anal. Biochem.* 234:60-5, 1996) describe a method for attaching nickel to a plastic substrate. Briefly, to charge microtiter polystyrene plates, 100 μl of N,N-bis[carboxymethyl]lysine (BCML) is added (10 mM BCML in 0.1 M $NaPO_4$, pH 8) to each well and incubated overnight at room temperature. The plate is subsequently washed with 200 μl of 0.05% Tween, blocked (3% BSA in 50 mM Tris HCl, pH 7.5, 150 mM NaCl, 0.05% Tween) and washed with a series of buffers: First 50 mM Tris HCl, pH 7.5, 500 mM imidazole, 0.05% Tween; second, 0.05% Tween; third, 100 mM EDTA, pH 8.0 and last 0.05% Tween. The plate is next incubated with 10 mM $NiSO_4$ for 20 minutes at room temperature. The plate is finally washed with 0.05% Tween and then 50 mM Tris HCl, 500 mM NaCl, pH 7.5.

Random attachment of the probe to a substrate should be sufficient at low probe concentrations. To allow for the tightest packing of sequencing signals in the field of view, the probes can be arranged on a two-dimensional substrate surface in an organized array. Probes can be spaced by micrometer distances as described by Müller et al. (*Science* 268:272-3, 1995, herein incorporated by reference). In addition, patterns of channels that are approximately 50 μm in width and approximately 10-20 μm in depth can be formed in the substrate using standard photolithographic procedures followed by chemical wet etching as described in U.S. Pat. No. 5,661,028 to Foote (herein incorporated by reference). Much smaller channels can be generated using nanolithography techniques. Dense periodic arrays of holes or chambers 20 nm across are fabricated into a silicon nitride coated substrate by the method of Park et al. (*Science*, 276:1401-4, 1997, herein incorporated by reference). In each chamber, a single sequencing reaction would take place. The probe can also be attached to the substrate in an orderly array by micropipetting droplets containing the probe onto the surface of the substrate. The droplets can be covered, for example with a glass coverslip, to prevent evaporation.

Embedding in a Gel Matrix

As an alternative to attaching the probe or nucleic acid molecule to a two-dimensional surface, they can be embedded into a three-dimensional gel matrix. For example, the probe, nucleic acid molecules, or both, are added to the liquid matrix, which is allowed to solidify, trapping the agents within it. Examples of this type of matrix include agarose and acrylamide, for example $Ni^{2+}$-NTA-Agarose (QIAGEN, Valencia, Calif.).

EXAMPLE 8

Calculation of Distance Between Fluorophores with Different Rod Lengths

As described above, the disclosed nanoprobes can include a polymerizing agent attached to a chemical moiety via a molecular rod, for example a rod that includes a tether, for example a tether composed of PEG (for example see molecular linkers 14, 16, 18 of FIG. 1A). However, with no force to keep them separated, the free PEG chains will each condense to form a cloud around a single point. Therefore, the addition of one or more molecular rods to the nanoprobe (for example as shown in molecular linker 20 of FIG. 1A) can be included to further separate the polymerizing agent and the chemical moieties, or to further separate fluorophores or other tags on the probe.

This example describes computer simulations used to determine how a FRET signal is affected by the length of a molecular rod, which can be, for example, composed of dsDNA. Molecular linker 20 in FIG. 1A shows the situation in the simulation. Two tethers 68, 70 are connected to a rod 66 and the distance between fluorophores 38 and 30 is measured. For the purpose of the simulation, polymerizing agent/12, fluorophore 30, moiety 28 and fluorophore 38 are all considered to be point objects. For a single tether, assuming that the tether is infinitely thin (does not have a problem intersecting with itself) and that the distance from the attachment point to the end of the tether is a random walk in three dimensions. In each single dimension this is the sum of small random steps, which would give a Gaussian distribution. In three dimensions it will be the spherically symmetric Maxwell gas distribution (Schneider, *J. Theor. Biol.*, 148:83-123, 1991). It is not appropriate to merely integrate over the intersection of two such distributions with a given separation because individual molecules will be at specific directions and distances. For this reason, an explicit simulation was performed.

To summarize the method, for each rod length, the two tethers were grown and the distance between the tips and then the FRET efficiency was computed. In the simulation, encoded by the program Bite (bi-tether), two polymers were attached to the ends of a fixed rod. Each polymer was generated by a series of random steps, starting from a rod end. The size of the steps is given by the persistence length of the chain. For PEG, the persistence length is 3.8±0.02 Å. The direction of each step was chosen randomly. The FRET signal was computed for each pair of randomly extended chains. This signal is a function the final distance between the tether chain ends R, and the FRET radius $R_0$ according to the FRET efficiency, $$E = 1/((R/R_0)^6 + 1) \tag{1}$$

The parameters used by the program include the persistence length, the length of the tethers L and the rod length D that separates the tether points. This process was repeated 1000 times to obtain the distributions shown in FIG. 4.

Figure 4A:
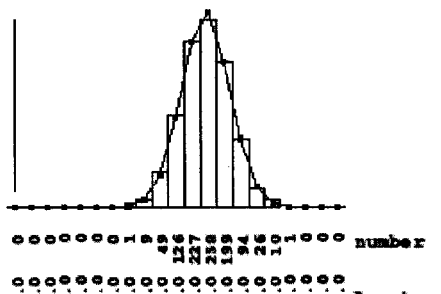
FIGS. 4 A-F are graphs showing the distance between fluorophores and FRET at several molecular rod lengths. A rod has two tethers and FRET is measured between the tether tips. This is a computer simulation. The tethers are 120 Å long and consist of segments that have the persistence length of PEG (3.8 Å). (E and F) rod length 0 Å. (C and D) rod length 60 Å. (A and B) rod length 120 Å. The data were generated using the bite program and graphed using the genhis and genpic programs.
Figure 4B:
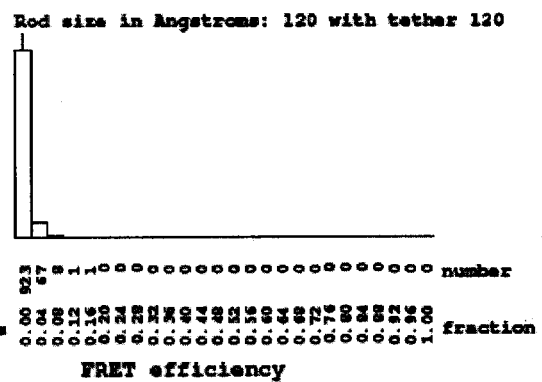
Figure 4C:
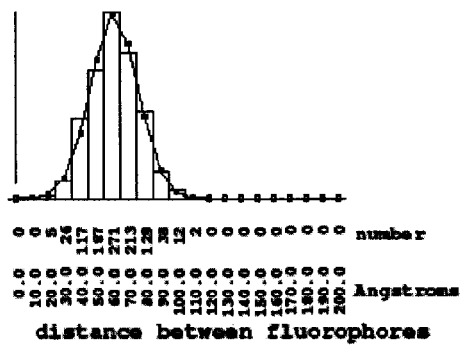
Figure 4C:
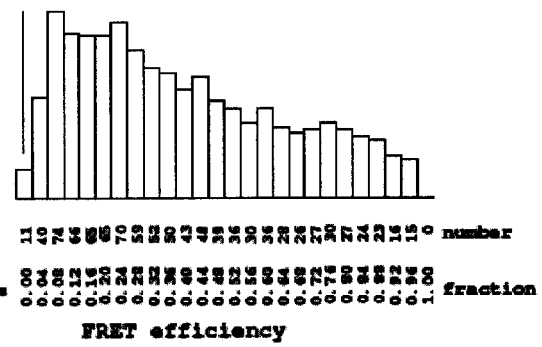
Figure 4E:
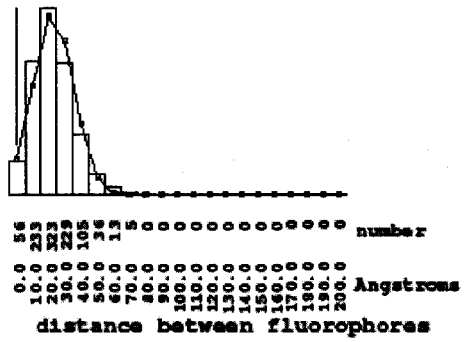
Figure 4E:
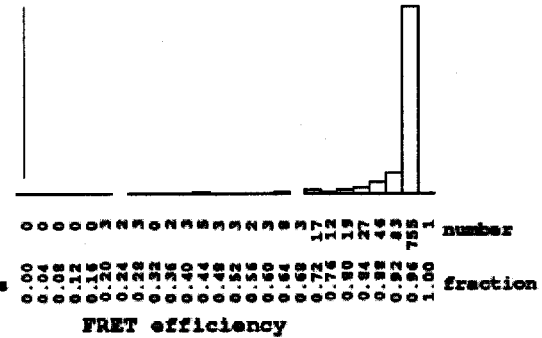

When the distance, R, between the fluorophores is $R_0$, the transfer efficiency is 50%. For example, for a FRET pair with an $R_0$=60 Å, which is a typical distance, and a tether length of 120 Å, FIGS. 4A-F show the effect of varying the rod length. With a rod length of 0 (FIGS. 4E and 4F) the tethers gather around a common point (FIG. 4E) leading to a large FRET signal (FIG. 4F). As the rod length is increased to 60 Å (FIG. 4C), the FRET distribution signal spreads out (FIG. 4D). Sometimes the two ends are close and some FRET will be observed. Strikingly, when the rod length is 120 Å (FIGS. 4A and 4B), the FRET signal is almost completely eliminated (FIG. 4B). This happens when the tether length is twice the rod length, so there is plenty of potential overlap of the tethers, allowing the tethers to bind to the target. Yet the FRET signal is almost undetectable. These results demonstrate particular advantages of including a rod in a molecular linker.

EXAMPLE 9

FRET with Different Tether Lengths

This example describes methods used to determine the effect of changing the length of a tether on a FRET signal.

The Bite program was run with various tether lengths (FIG. 5). In the upper left (FIG. 5A) a very short tether of 2 Å results in the basic FRET curve given by equation (1). As the tether length is increased from 2 to 60 Å, 120 Å and then 140 Å (FIGS. 5B, C and D), the basic FRET curve remains, but the distribution becomes more spread out. With a molecular rod length of about 120 Å and tethers of 120 Å, there is little FRET even though the tethers could overlap significantly. Therefore, use of a molecular rod of about 120 Å and tethers of 120 Å, results in almost no FRET until the two tethers are brought together by binding to the target molecule.

Figure 5A:
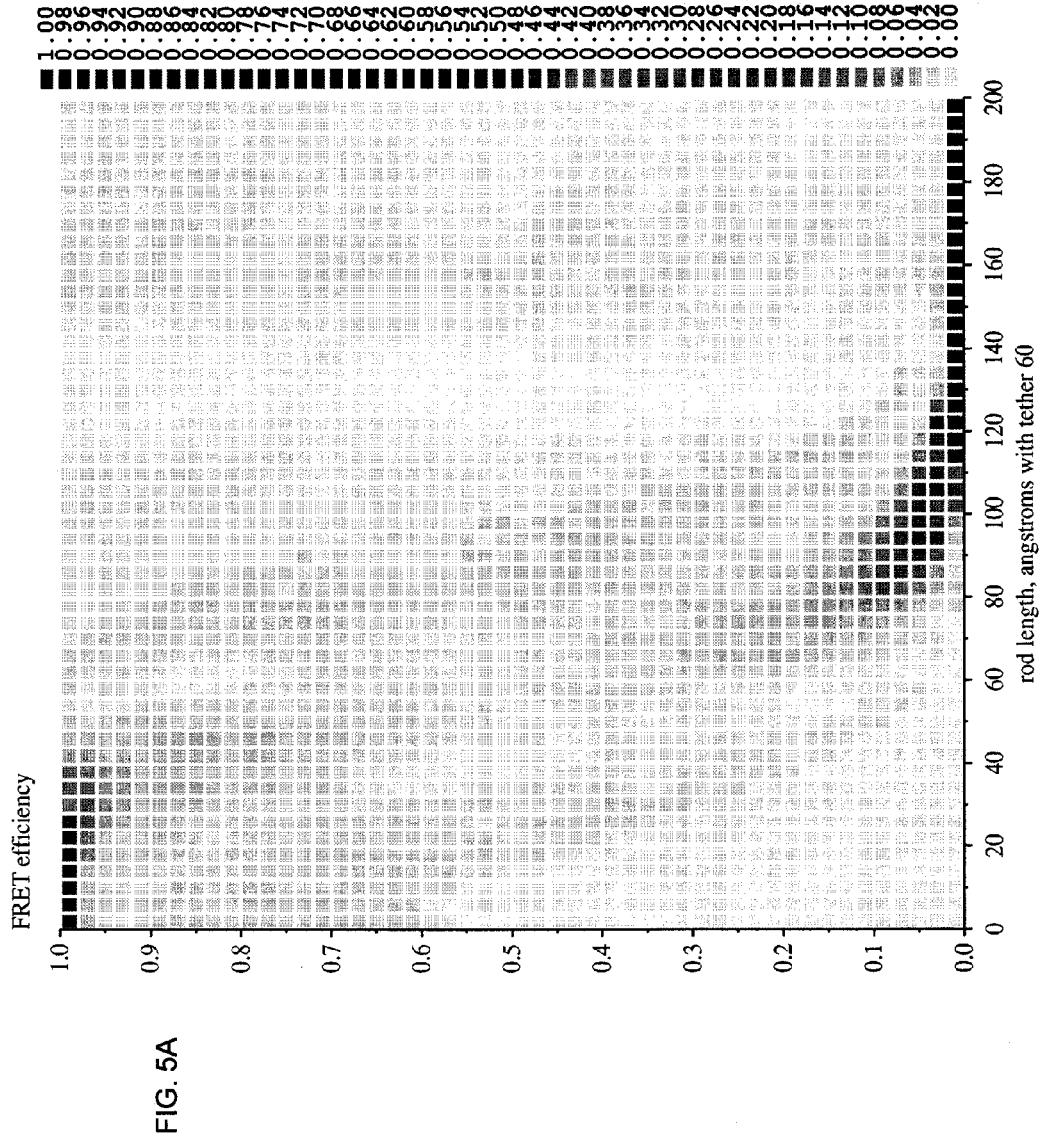
FIGS. 5A-D are graphs showing the effect of tether length on FRET at various rod lengths. The FRET distance, $R_0$, is 60 Å. Each graph shows the FRET efficiency versus the rod length. The color corresponds to the frequency that the nanoprobe gives a particular FRET signal. (A) tether length 2 Å.
Figure 5B:
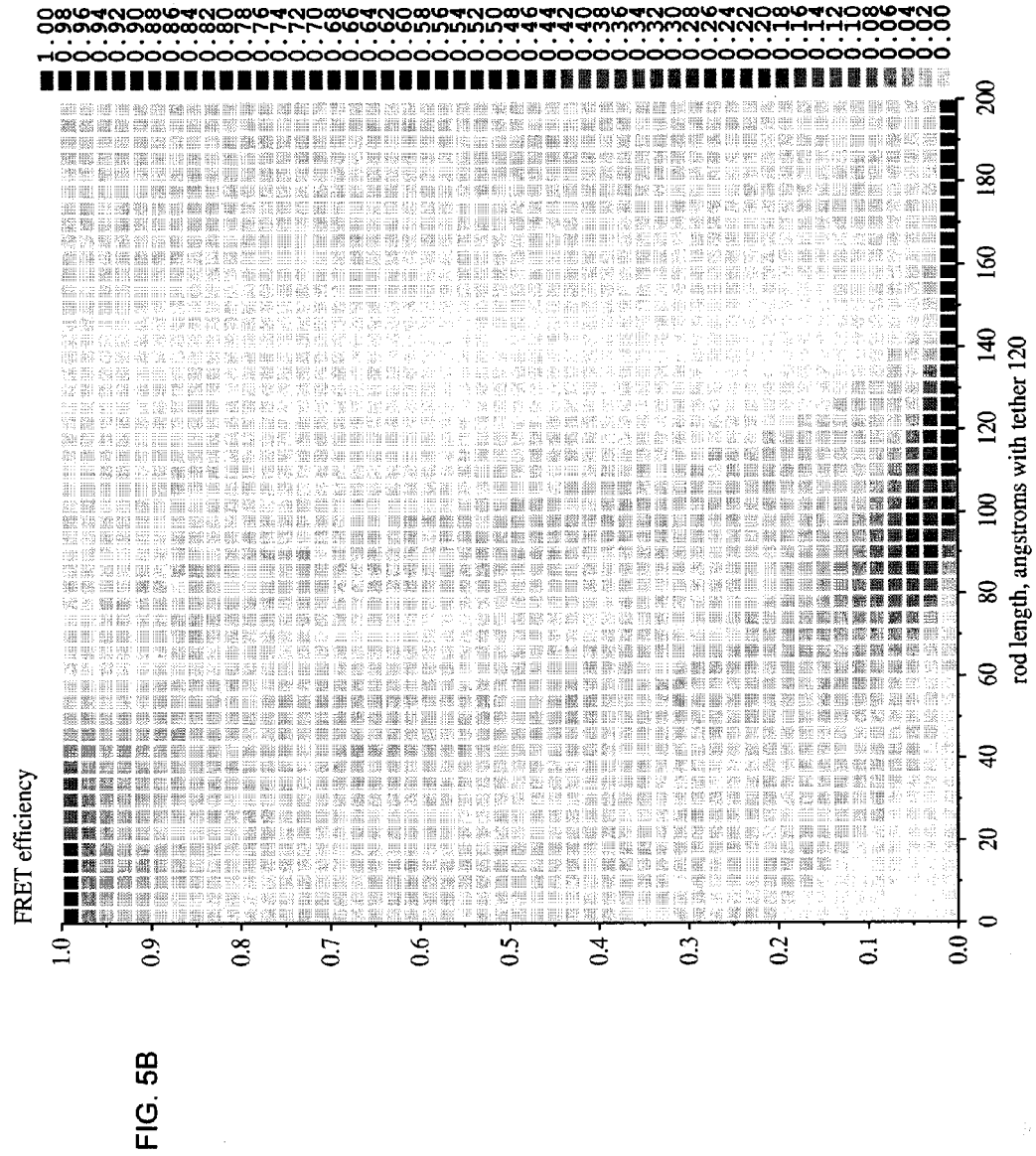
Figure 5C:
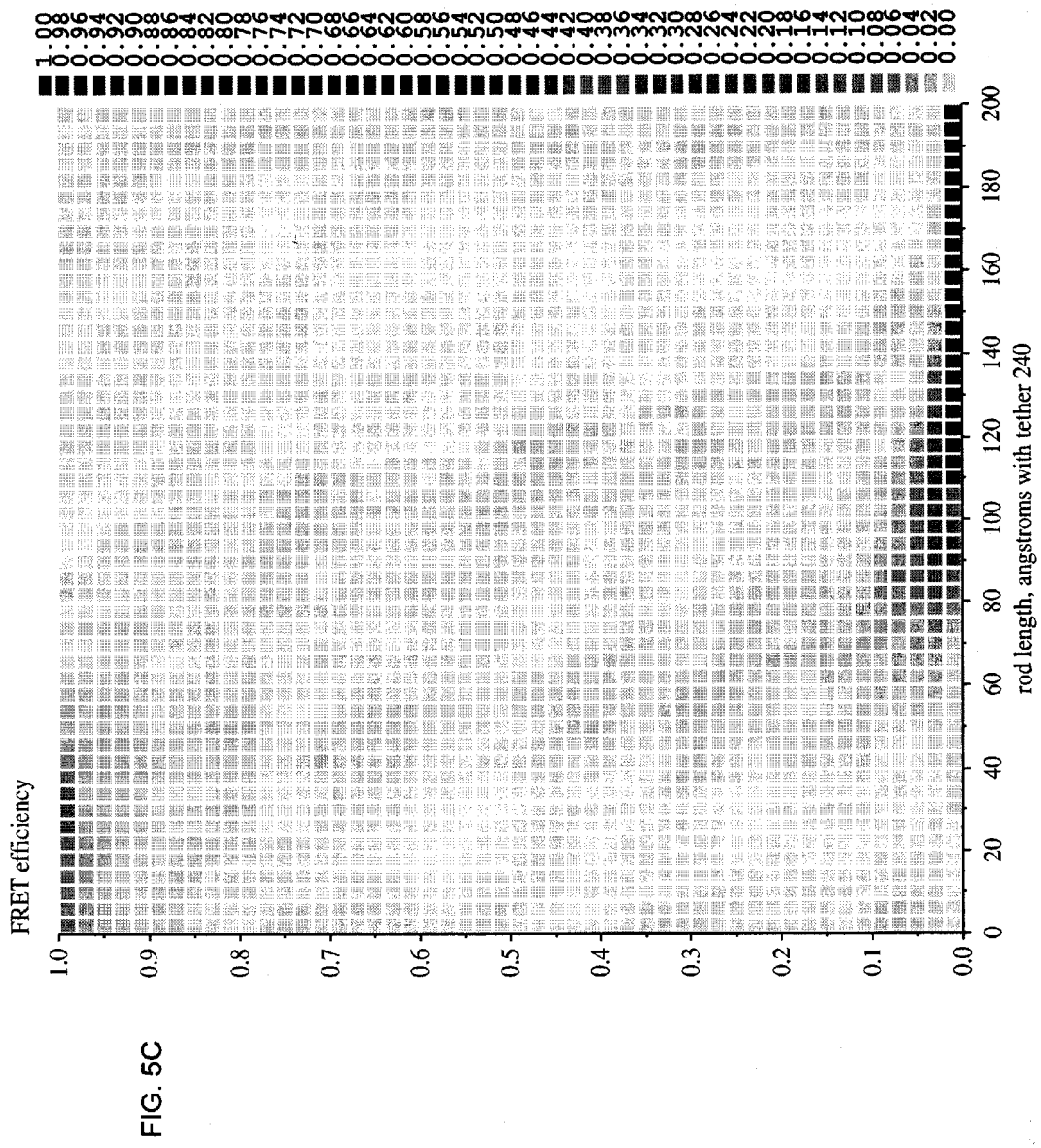
Figure 5D:
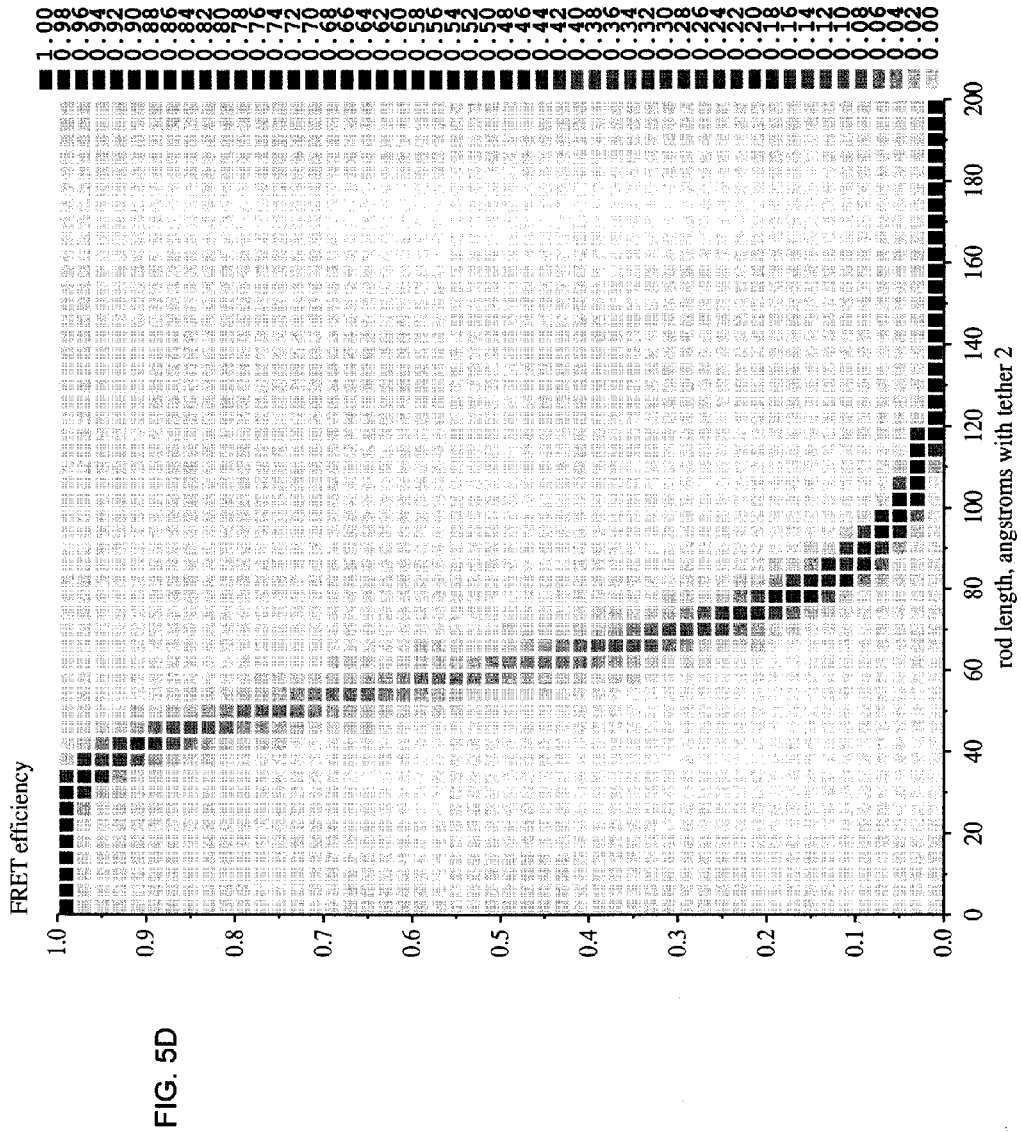

Even with tethers that are 240 Å long (FIG. 5D), the right side of the distribution is almost the same as with 120 Å long tethers (FIG. 5C). That is, tether length makes little difference to the FRET results, but molecular rod length has a significant effect.

In summary, the length of the tether had little effect on FRET, while the length of the molecular rod made a significant difference. Including a rod in the molecular linker of a nanoprobe reduces FRET to almost undetectable levels, even when tethers are more than sufficiently long to reach the target. In contrast, in the presence of a target the FRET signal can be large. This provides a strong molecular switch on the output signal based on the presence or absence of the target. An example of a useful rod-tether combination for a nanoprobe uses a rod of 120 Å with two tethers also of 120 Å. These are conveniently constructed from 40 nucleotides of dsDNA, to create the rod, and 5 to 6 PEG 18 spacers of 23 Å each, to create tethers.

Two time scales can be considered in understanding the operation of molecular nanoprobes. On the time scale of molecular vibrations, picoseconds, the tethers will explore a large variety of possibilities and the joining of two tether tips that are separated by a molecular rod appears to take a long time. For example, this process could take several orders of magnitude longer than molecular vibrations, for example, 100 milliseconds. Although 100 milliseconds is a long time from the viewpoint of molecular motions, it is only 1/10th of a second on the human time scale. Thus a detection process using a molecular probe may appear to be quite rapid.

EXAMPLE 10

Using Medusa Sequencers Macroscopically

This example describes methods of using the probes described herein macroscopically. For example, these methods can be used to determine the properties of a Medusa probe without resorting to single molecule detection.

To observe the transient dwell event, a hairpin DNA such as the one described in Example 2 can be used. A schematic overview of a hairpin oligonucleotide that can be used is shown in FIG. 7. The top of FIG. 7 illustrates a hairpin oligonucleotide with a 5' overhang (such as four base pairs) and fluorescent donor label (circle). A freely diffusing dTTP is labeled with a FRET acceptor (hexagon). The bottom shows FRET between the donor and acceptor when the labeled dTTP is held to the hairpin by a polymerase (ellipse). The hairpin is designed to have a small overhang that exposes "A" as the next base to be read. The oligonucleotide has a donor fluorophore on the 5' end. In some examples, this control DNA is filled in with an acceptor fluorophore labeled dTTP (or dUTP). This will result in FRET and an acceptor emission signal.

Measurements of single hairpin DNA molecules having a small 5' overhang (four bases) that exposes "A" as the next base to be read, a donor fluorophore (Alexa Fluor 488) on the 5' end (SEQ ID NO: 31, with a Alexa Flour 488 on the 5' end) were obtained using Image Correlation Spectroscopy (ICS). Using an Olympus Fluo View FV1000 confocal microscope, a 1 nM sample of this hairpin oligonucleotide was imaged. The low concentration of labeled DNA ensured there was only one fluorophore per confocal volume (about 1 femtoliter).

Measurements of hairpin DNA molecules having a small 5' overhang (four bases) that exposes "A" as the next base to be read, a donor fluorophore (Alexa Fluor 488) on the 5' end, and a covalently attached 3' acceptor-labeled dUTP (Alexa Fluor 594-dUTP) (SEQ ID NO: 32) were made. FRET was observed at about 200 nM oligonucleotide concentration using a Molecular Devices SpectraMax Gemini EM plate reader, and at a much lower concentration (10 nM oligo) using a Zeiss LSM 510 Meta NLO confocal system. Therefore, this confocal method might be used to detect nucleotide dwell.

Measurements of both free Alexa Fluor 555-labeled nucleotides and hairpin DNA molecules having a small overhang (four bases) that exposes "A" as the next base to be read and a fluorophore (Alexa Fluor 555) on the 5' end, (SEQ ID NO: 33) were made using fluorescence correlation spectroscopy (FCS). The labeled hairpin molecule diffused much slower than the labeled nucleotides due to the higher mass of the hairpin oligonucleotide. Therefore, FCS methods might be used to detect nucleotide dwell.

For example, a hairpin oligonucleotide having a dideoxynucleotide on the 3' end (such as ddC), and a 5' end that includes a small overhang (such as four bases) that exposes a nucleotide (such as "A" or "G") as the next base to be read and a donor fluorophore, can be used (see FIG. 7), Because this hairpin oligonucleotide cannot be extended by a polymerase, and the acceptor-labeled dNTP cannot be attached to the hairpin oligonucleotide, it is a model for the non-hydrolyzable arms of the disclosed sequencing probe. Such an unextendable oligonucleotide can be imaged in the presence of a polymerase and labeled nucleotides (such as labeled dNTPs, such as acceptor-labeled dUTP, for example Alexa Fluor 647-labeled dUTP or Alexa Fluor 647-labeled dCTP) to observe the nucleotides dwelling in the polymerase pocket. Nucleotides bound to the pocket/template will diffuse much slower than free nucleotides in solution. For example, comparing the imaging of a matched nucleotide to one that is not complementary to the template can be performed to monitor dwell, wherein nucleotides that match will dwell longer than those that do not match. For example, to demonstrate that the base is specifically but noncovalently bound, the occurrence of dwell events in the presence of acceptor-labeled dUTP will likely be minimally affected by competition by dATP, dCTP or dGTP but should be drastically reduced by competition with dUTP.

The different dwell times can be demonstrated by using labeled non-complementary bases (for example bases having the label on the same position). For example, fluorescent labels on dCTP and dUTP from Invitrogen/Molecular Probes are all attached to the C5 position.

In some examples, the hairpin DNA contains a biotin for attachment to surfaces thereby permitting measurements of nucleotide dwell in individual molecules in discrete locations.

Another exemplary construct that can be used to monitor dwell is shown in FIG. 8. In this example, the acceptor-labeled nucleotide triphosphate (such as dNTP) is attached to the hairpin oligonucleotide via a linker, such as by conjugating the triphosphate's 5'γ-phosphate to a primary amine on the linker via a carbodiimide cross-linker. This will generate a single linker or "arm" of Medusa. In intermediate designs, two or three tethered arms can be added. In addition, the arms can attached to the polymerase and the polymerase can be attached to a surface. The polymerase can be induced to step along the hairpin DNA by adding free nucleotide triphosphates. For example, if the first base to be added is dCTP, the second base to be added is dTTP and the "arm" contains a labeled dUTP, then there should be little signal without dCTP. However, when dCTP is added, the polymerase will step, allowing the labeled dUTP on the arm to FRET with the DNA donor. The dwell times using a Medusa sequencer having multiple "arms" can be measured by sequentially adding bases to a tethered DNA. As each base is added to the solution, the predicted single molecule spectrum is observed. This process can be observed in real time, demonstrating a single nucleotide step. For example, single molecule detection methods can be used to detect nucleotide dwell using this construct.

Using the hairpin DNA molecules described above, it is also possible to demonstrate that FRET occurred by cutting a hairpin with a restriction enzyme such as EcoRI (GAATTC is in the sequence along with a F is site) or using DNase I, and the FRET should decrease. A second oligonucleotide replaces a C at the 3' end with a dideoxy C, so the next base cannot be covalently attached. Mixing the oligonucleotide with the fluorescent dTTP will give no FRET. Adding a polymerase will allow the fluorescent dTTP to bind and give FRET. The FRET from the fluorescent dTTP can then be competed away with regular dTTP, while dGTP, dATP and dCTP should not compete. These methods can be used to demonstrate that the dTTP dwells in the polymerase.

Progressively more complex constructs can be examined, leading to a complete Medusa probe. For example, PEG can be added to the 5' end of the hairpin oligonucleotide described above, leading to a fluorophore and a T. This is, essentially, a single arm Medusa probe that can be used as above except that free fluorescent dTTP is not required because it is now part of the experimental construction. A second arm can then be added to the construction by using a stretch of DNA hybridized to a single stranded DNA extended from the 5' end of the hairpin.

A complete Medusa probe can be tested using the original hairpin without any attached fluorophore:

(SEQ ID NO: 34)
```
5' T-T-T-G-C-A-G-T-C-G-G-A-C-T-A-C-C-G
           | | | | | | | | | | | | |>·
         3' C-A-G-C-C-T-G-A-T-G-G-C
```

The hairpin is designed so that the bases to be added at the 3' end consist of the four dNTPs in a unique order. In the design shown, the bases to be added to fill in the overhang are dTTP, dGTP, dCTP and dATP.

The hairpin is mixed with Medusa molecules, without any dNTPs and the solution is placed into a spectrofluorometer. Since the next base to be added is a T the Medusa probe will produce a T signal. This signal will be stable because there are no additional nucleotides available in solution. All Medusa probes will give the same signal, allowing the result to be read macroscopically. Any Medusa probes that are not performing the correct operation will give a background signal so this provides a means of estimating the error rate of individual Medusa probes.

The result indicates that the template strand contains a T. That is, the Medusa probes have read a single base of sequence. Since T is the base reported by the probes, dTTP can be added to the solution and the spectrum can be determined again. Over time the spectrum will switch to giving a G signal since a C is now in the pocket. The Medusa probes have therefore reported the second base of the sequence. The sequence reported using these methods is compressed. That is, if the overhang contained several bases of the same kind adjacent to each other, the probes will only report a single base.

The method proceeds as follows, starting again from the beginning:

Adding dTTP the hairpin filled in by one base is obtained:

(SEQ ID NO: 35)
```
5' T-T-T-G-C-A-G-T-C-G-G-A-C-T-A-C-C-G
           | | | | | | | | | | | | |>·
         3' T-C-A-G-C-C-T-G-A-T-G-G-C
```

At this time the Medusa probes will report a G signal.

Adding dGTP the following hairpin filled in by two bases is obtained:

(SEQ ID NO: 36)
```
5' T-T-T-G-C-A-G-T-C-G-G-A-C-T-A-C-C-G
         | | | | | | | | | | | | | |>·
       3' G-T-C-A-G-C-C-T-G-A-T-G-G-C
```

At this time the Medusa probes will report a C signal.

Adding dCTP the hairpin filled in by three bases is obtained:

(SEQ ID NO: 37)
```
5' T-T-T-G-C-A-G-T-C-G-G-A-C-T-A-C-C-G
       | | | | | | | | | | | | | | |>·
     3' C-G-T-C-A-G-C-C-T-G-A-T-G-G-C
```

Finally, the Medusa probes will report an A signal.

Adding dATP the fully filled in hairpin is obtained:

(SEQ ID NO: 38)
```
5' T-T-T-G-C-A-G-T-C-G-G-A-C-T-A-C-C-G
     | | | | | | | | | | | | | | | |>
   3' A-A-A-C-G-T-C-A-G-C-C-T-G-A-T-G-G-C
```

All four nucleotides are in solution at this point. Because the hairpin has been fully filled in, the Medusa probes will stop producing signals.

These methods can therefore test all four Medusa arms and also the state of completing a sequence without requiring a single molecule detection system.

EXAMPLE 11

Microscope System

This example describes microscope systems that can be used to sequence target nucleic acid molecules using the probes disclosed herein.

Microscopes

Total internal reflection (TIR) fluorescence microscopy can be used, for example using the methods and device described by Pierce et al. (*Nature*, 388:338, 1997; *Methods Cell Biol.* 58:49, 1999); Funatsu et al. (*Nature*, 374:555, 1995); Weiss (*Science*, 283:1676, 1999) and Schutt et al. (U.S. Pat. No. 5,017,009). TIR is an optical phenomenon that occurs when light is directed at less than a critical angle, through a high refractive index material, toward an interface of that material with a second material having a lower refractive index. In this situation, all light is reflected back from that interface, except for a microscopic evanescent wave which propagates into the second material for only a short distance. In particular examples, TIR and single molecule detection are performed using a simple optic fiber in a regular fluorescent microscope (for example see Fang and Tan. *Anal. Chem.*, 71:3101-5, 1999; Xu and Yeung. *Science*, 275:1106-9, 1997; Ma et al., *Anal Chem*, 72:4640-5, 2000; and Levene et al., *Science*, 299:682%, 2003).

In TIR fluorescence microscopy, the first material is a glass substrate and the second material is water or another aqueous medium in which an assay is being conducted. When fluorescently labeled materials approach the interface, within the field of the evanescent wave, the fluorescent molecules can be excited, and fluorescence detected which then emanates into the overlying solution. TIR produces a superior signal-to-noise ratio, and reduces the photobleaching of the fluorescent molecules since only a thin layer of the sample is exposed.

Methods of reducing photobleaching are known in the art, and the disclosed methods are not limited so particular reduction methods. In one example, confocal microscopy can be used to reduce photobleaching of fluorophores. An example of a confocal laser is the Leica Confocal Spectrophotometer TCS-SP (Leica, Germany). The confocal laser will only illuminate sequencing polymerases, leaving the remainder of the reservoir dark. To accomplish this, one can first scan the entire volume available for polymerases then program the microscope to only expose those small regions containing functioning polymerases. Confocal microscopy can be used to sequence reactions in three dimensions (see U.S. Pat. No. 6,982,146). Confocal microscopy excludes planes that are not of interest, allowing one to increase the total number of sequences taken. This permits more sequencing reactions to be performed and detected per field of view.

Near-field scanning optical microscopy (NSOM) can also be used for the sequencing method disclosed herein. Several methods and devices for NSOM have been described (U.S. Pat. No. 5,105,305 and PCT Publication WO 97/30366). In NSOM, an aperture having a diameter that is smaller than an optical wavelength is positioned in close proximity (such as within less than one wavelength) to the surface of a specimen and scanned over the surface. Light can be either emitted or collected by such an aperture in the end of a probe. Mechanical or piezoelectric means are provided for moving the probe relative to the sample. Light that has interacted with the sample is collected and detected by, for example, a spectrophotometer, and then a CCD camera. The strength of the detected light signal is typically stored, in the form of digital data, as a function of the probe position relative to the sample. The stored data can be converted into a nucleic acid sequence. NSOM allows optical measurements with sub-wavelength resolution, can measure FRET, and works well in solution (Ha et al., *Proc. Natl. Acad. Sci. USA* 93:6264-8, 1996). Standard microscopes can be converted to a near-field optical microscope using a device sold by Nanonics Ltd. (Malha, Jerusalem, Israel).

One advantage of NSOM is that high resolution of the sample can be obtained. However, since the probe scans the surface of the substrate, the number of sequencing reactions that can be monitored at any one time decreases. To help compensate for this decrease, the rate of nucleotide addition can be decreased by increasing the viscosity of the solution (for example by including PEG, Ficoll, glycerol, or combinations thereof, at appropriate concentrations to the solution) or decreasing the temperature.

Kairos Scientific provides a Fluorescence Imaging MicroSpectrophotometer (FIMS). This microscope generates a fluorescence emission spectrum for every pixel in the field of view. Therefore, a unique emission spectrum is generated for each nucleotide as it is added to the complementary nucleic acid strand.

In other examples, the method allows for single molecule detection (SMD), for example using the system disclosed by Fang and Tan (*Anal. Chem.* 1999, 71:3101-5, herein incorporated by reference). Briefly, in this system an optical fiber is used to probe into a solution (for example an aqueous environment or at a solid surface). The optical fiber has total internal reflection, allowing fluorescent molecules close to the surface to be excited by the evanescent wave. The fluorescent signals generated by the fluorophores are detected by an intensified charge-coupled device (ICCD)-based microscope system. Optical fibers can be purchased from Newport Corp. (Irvine, Calif.).

In yet other examples, SMD can be performed using the method disclosed by Unger et al. (*BioTechniques*, 1999, 27:1008-14, herein incorporated by reference). Briefly, using a standard fluorescent microscope with mercury lamp excitation and a CCD camera, single fluorescent molecules can be observed in air and in aqueous solution, if the molecules are sufficiently separated by dilution.

Reducing Photobleaching

Methods of reducing photobleaching are known in the art, and the disclosed methods are not limited so particular reduction methods. In one example, confocal microscopy can be used to reduce photobleaching of fluorophores (described above). Another means that can be used to reduce photobleaching is to incubate the sample in a solution containing an oxygen scavenger system, for example as described by Kitamura et al. (*Nature*, 397:129, 1999); Okada and Hirokawa (*Science*, 283:1152, 1999); Harada et al. (*J. Mol. Biol.* 216:49, 1990). Examples of solutions include: 1% glucose, 0.05 mg/ml glucose oxidase and 0.1 mg/ml catalase; and 0.5% 2-mercaptoethanol, 4.5 mg/ml glucose, 216 µg/ml glucose oxidase, 36 µg/ml catalase, 2 mM ATP in buffer.

One method that can be used to reduce photobleaching is to coat fluorophores with calcium phosphate (also known as molecular dots). For example, when trapped inside 60 nm nanoparticles, fluorophores remain extremely stable and do not significantly decay. For the present probes, small nanoparticles of about 0.5-2 nm (such as 1 nm to 2 nm) having one amino group (or other unique attachment point) on the surface can be used. For example, a tethered fluorophore having an amino group (to permit attachment of the fluorophore to the desired location on the nanoprobe) can be coated and attached to a nanoprobe. The layering can be accomplished by incubating the fluorophore with carboxyl (—COOH) groups and then adding calcium or aluminum. On adding phosphate $H_2PO_4^-$, another layer is formed. In some examples, gold is used to coat the fluorophores. The resulting particles have plasmon resonance, possibly enhancing the fluorescence in addition to the protective coating (see Lakowicz, *Anal. Biochem.* 298: 1-24, 2001).

Yet other methods of reducing photobleaching include placing a nanoprobe sequencer disclosed herein and the target nucleic acid molecule proximal to metallic islands (Lakowicz, *Anal. Biochem.* 298: 1-24, 2001) and incubation in Trolox (Rasnik et al., *Nat. Methods* 3:891-3, 2006).

Sources of Electromagnetic Radiation

In particular examples, electromagnetic radiation is emitted by a laser. The choice of laser used will depend on the specific donor fluorophore used. The wavelength of the laser light is selected to excite the donor fluorophore. For example, wild-type GFP and FITC can be excited by an argon laser at 488 nm. To excite the H9-40 GFP mutant, blue laser diodes which emit at 400 nm (Nichia Chemical Industries Ltd.) or 404 nm (Power Technology Inc., Little Rock, Ark.) can be used. Other sources of electromagnetic radiation known by those skilled in the art can also be used, for example HeNe lasers and mercury lamps.

Fluidics

The use of a fluid handling system is optional. For simplicity, one may prefer to add all of the necessary reagents, then seal the chamber with a glass coverslip or a drop of oil to prevent desiccation. Alternatively, a slow flow of nucleotide-containing solution can be provided to replenish the nucleotides and to remove the products (diphosphate). Such a system would increase nucleotide use, but would maintain steady-state conditions, which may increase the length of sequencing runs.

A computer chip that performs the liquid handling can be built that sits on the stage of a fluorescent microscope. Micromachine and microfluidic devices and methods for the dispensing of nanoliter size liquid samples has been previously described (Service, *Science* 282:399-401, 1998; Burns et al. *Science* 282:484-7 1998).

Detectors

A detector permits capture of the emission spectra generated by the spectrophotometer.

A CCD camera can be used as the detector to capture the image. The emission spectra generated by the spectrophotometer are collected by the CCD camera, which converts this input into charges. The charges are converted into a signal by the CCD output.

The resulting signal is digitized, as a characteristic signal associated with each type of nucleotide (such as A, T/U, C or G), and the digital data is captured into memory, such as the hard drive of a computer. The sum of the captured data is then processed into a nucleotide sequence. CCD cameras are commercially available from many sources including Kodak (Rochester, N.Y.).

With color CCD cameras containing more than 1000 by 1000 pixel fields (for example the Kodak Professional DCS 520 Digital Camera), or even 4096 by 4096 pixel fields (for example the Kodak 16.8i, KAF16800), it may be possible to sequence as many as 1000 nucleic acids in parallel, at a rate of up to 750 bases per second. Therefore, molecular sequencing with the probes disclosed herein has the potential to sequence entire chromosomes or genomes within a day. If the polymerases are placed in a regular hexagonal array, about 17 pixels would be available for each polymerase.

Alternatively, a monochrome CCD containing filters or other means of obtaining a spectrum can be used. To reduce background noise, any of the CCD cameras may be cooled.

The rate at which sequencing of the nucleic acids occurs can be controlled by many factors. Faster rates can be obtained by increasing the temperature (using a heat stable polymerase and PNA for rods) or by running the reactions under high pressure, as in HPLC. The reaction rate can be slowed by making the solution more viscous, by lowering the reaction temperature, by having fewer reactive nucleotides available, or by having free non-hydrolyzable, non-fluorescent dNTPs available. The rate of polymerization may be controlled in this manner not to exceed the rate of the CCD integration and computer recording time. Therefore, the rate of polymerization is controlled in this manner such that the fluorescent signal can be more reliably read by the CCD and interpreted by the computer.

In one example, the method is performed in a closed-chamber device that produces sequencing signals, which enter the computer directly. The method sequences nucleic acid molecules by monitoring the pairing of a chemical moiety with its complementary nucleotide in the target nucleic acid molecule on the molecular level, instead of sequencing nucleic acids by monitoring macromolecular events, such as a pattern on an electrophoresis gel, which is representative of a large population of nucleic acid molecules. Once the reaction has started, no further liquid handling is necessary (but can be added if desired). Therefore, the machine has no macroscopic moving parts during operation, which can facilitate rapid sequencing.

As an alternative to a CCD camera, photomultiplier tubes or an intensified charge-coupled device (ICCD) can be used In one example, a superconductor is used to detect the FRET signals. superconductor-based light detectors are sensitive detectors coming that give the entire spectra from single molecules with very little loss of photons. In some examples, the superconductor is brought to its transition temperature. This is the temperature at which it loses superconductivity. When a photon hits the superconductor, it loses superconductivity in proportion to the energy of the photon. Therefore, it can not only detect individual photons but also can give the frequency of the light since that is proportional to the energy (by hv). An individual pixel of a detector can be maintained at the transition by placing a voltage across the device. If the device temperature is too high, the resistance increases, decreasing the current and reducing the temperature again.

Increasing Signal

In addition to reducing photobleaching, methods are known in the art to increase the signal detected. For example, a high numerical aperture microscope objective can be used, as well as the use of metallic islands near fluorophores (Lakowicz, *Anal. Biochem.* 298: 1-24, 2001). Metallic islands decrease the lifetime which reduces photobleaching and increases the number of photons by about 100-fold.

In one example, mirrors are placed above the fluorophore. In another example, the sample is surrounded by a parabolic reflector, thereby increasing the FRET signals at the focal point. For example, Kartalov et al. (*BioTechniques*, 40:85-90, 2006) provide microfluidic devices having a parabolic flow channel profile. Such devices can be used in the methods disclosed herein. In one example, the channel of the microfluidic device has a reflective substance, and a laser is directed down the length of the device to excite the fluorophores. In one example, total internal reflectance (TIR) is used to excite the fluorophores.

EXAMPLE 12

Computer System

The methods disclosed herein can be performed in the general context of computer-executable instructions of a computer program that runs on a personal computer. Generally, program modules include routines, programs, components, data structures, etc. that perform particular tasks or implement particular abstract data types. Moreover, those skilled in the art will appreciate that the method may be practiced with other computer system configurations, including hand-held devices, multi-processor systems, microprocessor-based or programmable consumer electronics, mini-computers, mainframe computers, and the like. The methods disclosed herein can also be practiced in distributed computing environments where tasks are performed by remote processing devices that are linked through a communications network. In a distributed computing environment, program modules may be located in both local and remote memory storage devices.

The present implementation platform of the methods disclosed herein is a system implemented on a Sun computer having at least one gigabyte of main memory and a one gigabyte hard disk drive, with Unix as the user interface. The application software is written in Pascal, Java or other computer languages.

In particular examples Hidden Markov Modeling (McKinney et al., *Biophys. J.* 91:1941-51, 2006) is used to analyze and characterize obtained FRET data.

In particular examples, linear unmixing is used to analyze and characterize obtained FRET data. Linear unmixing is the process of working backwards from a given spectrum to determine the amounts of individual fluorophores that contributed to that spectrum (for example see Thaler et al., *Biophys.* 89:2736-49, 2005). For example, if it is determined that there is 99% A, 1% T, 0% G, 0% C, it is inferred the base is an A.

EXAMPLE 13

Sequencing Using Probe

This example describes methods for sequencing nucleic acids from different sources using the probes of the present disclosure. Although particular methods are provided, one skilled in the art will appreciate that variations to the method can be made.

In this example, reference will be made to the probe shown in FIG. 1B. However, one skilled in the art will understand that any of the probes disclosed herein can be substituted for this probe. In this example, the polymerizing agent 12 is a fluorescein-HIV-1-reverse transcriptase (and thus tag 30 is fluorescein), the chemical moieties 22, 24, 26, 28 are nonhydrolyzable dCMPCPP, dGMPCPP, dAMPCPP, and TMPCPP, and the tags 32, 34, 36, 38 associated with the chemical moieties are Cy3, Cy5, Texas Red, Rhodamine Red.

The sequencing reaction includes 5 µM probe, 5 µM primer, 1 ng-1 µg target nucleic acid sequence (such as 1 µg of sample nucleic acid), and 200 µM of each dNTP, and the reaction is performed in Ambion HIV RT First Strand Synthesis Buffer (10×): 500 mM Tris-HCl (pH 8.3), 750 mM KCl, 30 mM $MgCl_2$, 50 mM DTT. In one example, the target nucleic acid is obtained from a biological sample from a subject. In particular examples, the reaction proceeds at 45° C.

In this example, the donor fluorophore is fluorescein. Therefore, the sequencing reaction can be excited by a laser, such as a laser that emits a wavelength of light that will excite the donor (such as a 488 nm Argon laser).

The sequencing reaction is incubated under conditions that permit the fluorescein-polymerase 12 to bind to the primer/target nucleic acid sequence, and permit the nonhydrolyzable dCMPCPP, dGMPCPP, dAMPCPP, and TMPCPP 22, 24, 26, 28 to pair with the currently exposed nucleotide 44 on the target nucleic acid strand. When the fluorescein-polymerase binds to a target DNA or RNA 40 that has been primed by an oligonucleotide 42, each of the molecular linkers 14, 16, 18, 20 can flexibly extend to place the nonhydrolyzable dCMPCPP, dGMPCPP, dAMPCPP, and TMPCPP 22, 24, 26, 28 into the active site pocket of the fluorescein-polymerase 12. Thus the correctly paired nonhydrolyzable dAMPCPP 26 will remain in the polymerase active site pocket a long time (relative to the non-complementary nonhydrolyzable 22, 24, 28). The corresponding acceptor fluorophore 36 will be close to the donor fluorophore fluorescein 30 so there will be FRET between the two, thereby producing a spectral output that indicates which nonhydrolyzable dCMPCPP, dGMPCPP, dAMPCPP, and TMPCPP 22, 24, 26, 28 is currently pairing with the complementary base in the target strand being sequenced.

The emission signal from the acceptor fluorophore 36 currently pairing with the complementary base 44 in the target strand being sequenced 40 is detected. For example, the reaction can be observed under a fluorescent microscope or by a confocal microscope, wherein the microscope can capture the spectrum of each acceptor fluorophore used.

The nonhydrolyzable dCMPCPP, dGMPCPP, dAMPCPP, and TMPCPP 22, 24, 26, 28 (in this example 26) will eventually be replaced in the active site by the hydrolyzable non-labeled nucleotide (in this case dATP, 46), and be incorporated into the elongating complementary strand. This will step the probe forward one base on the target nucleic acid molecule 40. This exposes the next base on the target nucleic acid molecule 40 and the reaction will be repeated as described above. An acceptor emission signal will be detected when the complementary nonhydrolyzable nucleotide analog on the probe pairs with the exposed base. Thus the probe produces a time varying signal that represents the nucleotide sequence of the target molecule.

For example, the resulting emission signals may generate a series of pulses as shown in FIG. 6. The figure is similar to clocking pulses for digital electronics and computers. Time is along the horizontal axis, and the intensity of various signals is given as horizontal lines. The target sequence is given along the top, 5' A C G T T C A G T 3' (SEQ ID NO: 39). There is one line for each base. Distinct, spectral signals from the four fluorescently labeled nonhydrolyzable nucleotide analogs are converted into the corresponding complementary base on the target strand. The bottom line CLOSE represents when the polymerase is closed (as described herein the polymerase can include tags that monitor opening and closing of the polymerase). As each base on the target nucleic acid strand pairs with the complementary nonhydrolyzable nucleotide analog on the probe, the corresponding signal appears. Actual data will likely be noisier than shown, and the timing lengths will not likely be regular. When a pair of Ts are encountered as shown in FIG. 6, their signals may not be distinct, because of the noise. However, the polymerase must open and close to admit the second T, so the CLOSE signal provides a clocking by which to read that there were two T signals.

In one example, the method is used to determine if a subject has a mutation in a target nucleic acid sequence, such as a mutation associated with disease.

Many different sequences can be determined in parallel. One application of the disclosed method is the sequencing of a plasmid. After introducing random nicks into the plasmid, the DNA is added onto a substrate containing fixed probes. The entire plasmid is then sequenced from many points. The computer keeps track of all the sequences and automatically assembles them into a complete plasmid sequence.

Another use is for sequencing a randomly chemically synthesized region of a nucleic acid. The primer used is specific for a position just outside the randomized region. The randomized nucleic acids are placed onto the field of fixed polymerases. This method allows one to obtain the entire results of a randomization experiment in parallel, thereby saving time and money.

Nick translation can be used to initiate sequencing on an unknown nucleic acid.

EXAMPLE 14

Detection of Single Nucleotide Polymorphisms

The probes disclosed herein can be used to determine single nucleotide polymorphisms (as for example see Twist et al., *Anal. Biochem.* 327:3544, 2004) by targeting the sequencers with the sequence just upstream of the unknown base. No dNTPs are supplied. Medusa probe settle on the end of the primer and report the unknown base. To reduce costs, specialized probes that have fewer than four arms, and hence which can distinguish fewer bases, could be used in specific cases where many assays are desired.

EXAMPLE 15

Clinical Applications

This example describes how the methods disclosed herein can be used for the analysis of pathology specimens. The source of specimen obtained from a subject may include peripheral blood, urine, saliva, tissue biopsy, fine needle aspirates, surgical specimen, amniocentesis samples, tissue slices, cheek swabs, and autopsy material.

In particular example, the biological sample is attached to a substrate, such as a glass slide, under conditions that preserve the nucleic acid molecules present in the sample. Alternatively, the nucleic acids can be isolated from the sample, and then subjected to methods described in Example 13. For example, one can use the present method to sequence bacterial chromosomes and human genes containing mutations. Using techniques described herein, the presence of viral and/or bacterial pathogens can be detected by the presence of the viral and/or bacterial nucleic acid sequences. In addition, the methods disclosed herein allow for nucleic acid sequencing in situ, by adding a primer, a probe, and the four non-labeled hydrolyzable nucleotides, to a thin tissue slice.

In one example, the method is used to generated genetic profiles of normal, precancerous, and tumor cells for one or more cancers. For example, cDNA libraries from each of these cell types are sequenced to determine the genetic profiles of cancer cells. The disclosed methods can be used to obtain gene expression data directly with no cloning, conventional sequencing, or microarrays. This can reduce time and expense, thus allowing additional types of tissues to be determined.

In one example, the biological sample includes a tissue, such as a tissue microarray that includes large numbers of specimens, for example from large numbers of specimens. Such an array permits screening of a large number of specimens from many subjects, or many specimens from the same subject.

In view of the many possible embodiments to which the principles of the present disclosure may be applied, it should be recognized that the illustrated examples are only particular examples and should not be taken as a limitation on the scope of the disclosure. Rather, the scope of the disclosure is defined by the following claims. We therefore claim as our invention all that comes within the scope and spirit of these claims.

---

We claim:

1. A probe for sequencing a nucleic acid molecule, comprising:

a polymerizing agent having an active site capable of binding to a target nucleic acid molecule and promoting synthesis of a complementary nucleic acid molecule that elongates as complementary nucleotides are incorporated into the complementary nucleic acid molecule; and one or more molecular linkers spaced apart on the polymerizing agent, wherein the one or more of the linkers carry a nucleotide analog that is capable of reversibly binding to the target nucleic acid molecule, without being detached from the linker, by specifically binding with a complementary nucleotide in the target nucleic acid molecule, wherein specific binding of the nucleotide analog on the linker with a complementary nucleotide in the target nucleic acid molecule is indicated by emission of a characteristic signal that indicates pairing of the nucleotide analog on the linker with its complementary nucleotide.

2. The probe of claim 1, wherein the nucleotide analog comprises a non-hydrolyzable nucleotide analog.

3. The probe of claim 2, wherein the non-hydrolyzable nucleotide analog comprises a non-hydrolyzable triphosphate nucleotide analog.

4. The probe of claim 1, where the nucleotide analog is a mono-nucleotide.

5. The probe of claim 1, wherein the one or more molecular linkers comprises at least four independent linkers, each of which carries a different nucleotide analog capable of specifically binding with a different nucleotide in the target nucleic acid molecule.

6. The probe of claim 1, wherein the one or more molecular linkers form a branch structure, wherein each branch carries a different nucleotide analog capable of specifically binding with a different nucleotide in the target nucleic acid molecule.

7. The probe of claim 6, wherein the branch structure comprises at least four branches, wherein each branch carries a different nucleotide analog capable of specifically binding with a different nucleotide in the target nucleic acid molecule.

8. The probe of claim 1, wherein the polymerizing agent is associated with a tag, and wherein each of the nucleotide analogs is associated with a tag that identifies a particular nucleotide analog carried by the linker, wherein interaction of the tag associated with the polymerizing agent with the tag associated with the nucleotide analog induces emission of the characteristic signal that indicates pairing of the nucleotide analog on the linker with its complementary nucleotide in the target nucleic acid molecule.

9. The probe of claim 8, wherein the tag associated with the polymerizing agent forms a donor-acceptor pair with the tag associated with each nucleotide analog, whereby interaction of the donor-acceptor pair stimulates emission of the characteristic signal.

10. The probe of claim 8, wherein each of the tags that identifies a particular nucleotide analog carried by the linker, comprises one or more fluorophores that emits a unique emission signal.

11. The probe of claim 1, wherein the one or more molecular linkers comprise four molecular linkers, each of which carries a different nucleotide analog capable of reversibly binding to the template strand of the target nucleic acid molecule without being detached from the linker, and an acceptor tag associated with each nucleotide analog wherein the acceptor tag identifies the particular nucleotide analog carried by the linker, and the polymerizing agent is associated with a donor tag, wherein reversible binding of the nucleotide analog to the target nucleic acid molecule brings the donor and acceptor tag into sufficient proximity to induce emission of a characteristic signal of the acceptor tag that indicates the identity of the nucleotide analog carried by the linker.

12. The probe of claim 1, wherein the one or more molecular linkers are spaced around the polymerizing agent a sufficient distance to inhibit entanglement of the molecular linkers, and the molecular linkers are of sufficient length to reach the active site of the polymerizing agent.

13. The probe of claim 1, wherein at least a portion of the molecular linker is of a sufficient rigidity to reduce interaction of the polymerizing agent and the nucleotide analog in the absence of the target nucleic acid molecule.

14. The probe of claim 1, wherein the molecular linker comprises a double-stranded DNA (dsDNA) of at least 10 nucleotides.

15. The probe of claim 1, wherein the molecular linker comprises polyethylene glycol (PEG).

16. The probe of claim 1 where the polymerizing agent comprises a DNA polymerase, RNA polymerase, or reverse transcriptase.

17. A polymerizing agent comprising:
an active site capable of binding to a target nucleic acid molecule and promoting synthesis of a complementary nucleic acid molecule that elongates as complementary nucleotides are incorporated into the complementary nucleic acid molecule;
one or more molecular linkers spaced apart on the polymerizing agent to inhibit entanglement, wherein each linker carries a different nonhydrolyzable nucleotide analog that is capable of reversibly binding to the template strand of a nucleic acid molecule, without being detached from the linker, by specifically binding with a complementary nucleotide in the target nucleic acid molecule;
a tag associated with each nonhydrolyzable nucleotide analog that identifies the nonhydrolyzable nucleotide analog carried by the linker that is capable of reversibly binding to the template strand of a nucleic acid molecule; and
a tag associated with the polymerase that interacts with the tag associated with the nonhydrolyzable nucleotide analog to emit a characteristic signal that identifies the nonhydrolyzable nucleotide analog carried by the linker.

18. A method of determining a nucleic acid sequence of a target nucleic acid molecule, comprising:
exposing the target nucleic acid molecule to the probe of claim 1 in the presence of an oligonucleotide primer and a mixture of hydrolyzable nucleotides that are capable of being incorporated into an elongating nucleic acid molecule by hybridizing with a complementary nucleotide in the target nucleic acid molecule, and replacing the nucleotide analog that reversibly binds to the template nucleic acid molecule;
detecting emission of a sequence of signals comprising emission of a plurality of the characteristic signals that indicates pairing of the nucleotide analog on the molecular linker with its complementary nucleotide.

19. The method of claim 18, wherein the polymerizing agent is associated with a tag, and each of the chemical moieties is also associated with a tag that identifies a particular nucleotide analog carried by the linker, wherein interaction of the tag associated with the polymerizing agent with the tag associated with the nucleotide analog induces emission of the characteristic signal that indicates pairing of the nucleotide analog on the linker with its complementary nucleotide.

20. The method of claim 19, wherein the tag associated with the polymerizing agent comprises a donor fluorophore and the tag that identifies a particular nucleotide analog comprises one or more acceptor fluorophores, wherein interaction of the polymerizing agent and the nucleotide analog that specifically binds to the complementary nucleotide in the target nucleic acid molecule brings the acceptor fluorophore into a proximity with a donor fluorophore to permit excitation of the acceptor fluorophore by the donor fluorophore.

21. The method of claim 20, wherein detecting the signal comprises detecting a fluorescent signal emitted from the acceptor fluorophore or comprises detecting a reduction in fluorescent signal emitted from the donor fluorophore.

22. The method of claim 18, wherein the emission of a sequence of signals is converted into a nucleic acid sequence.

23. The method of claim 20, further comprising exciting the donor fluorophore to emit a signal which excites the one or more acceptor fluorophores to emit the characteristic signal that indicates pairing of the nucleotide analog on the linker with its complementary nucleotide.

24. The method of claim 18, wherein the probe is fixed to a substrate.

25. The method of claim 18, wherein the target nucleic acid molecule or the oligonucleotide primer is fixed to a substrate.

26. The method of claim 18, wherein the method comprises performing a plurality of sequencing reactions substantially simultaneously, and detecting the sequence of signals from the plurality of sequencing reactions.

27. The method of claim 26, wherein a plurality of polymerizing agents, target nucleic acid molecules, or oligonucleotide primers are fixed directly or indirectly to the substrate in a predetermined pattern, and detecting the sequence of signals further comprises correlating the signal with a nucleic acid molecule corresponding to a predetermined position within that pattern.

28. The method of claim 18, wherein the target nucleic acid molecule is present in a biological sample obtained from a subject.

29. The method of claim 18, wherein the target nucleic acid molecule is present in a cell, and the exposing step comprises introduction of the oligonucleotide primer and the probe into the cell.

30. The method of claim 18, wherein the target nucleic acid strand comprises one or more mutations associated with disease.

31. The probe of claim 1, further comprising a primer that specifically hybridizes to the target nucleic acid sequence under high stringency conditions, wherein the primer is attached to the polymerizing agent via a molecular linker 32. The probe of claim 8, wherein the tags associated with the nucleotide analogs are a coded fluorophore set that permits the detection and correction of errors.

33. The probe of claim 3, wherein the non-hydrolyzable triphosphate nucleotide analog comprises a non-hydrolyzable triphosphate nucleotide analog with an alpha-beta bond that is non-hydrolyzable.

34. The probe of claim 4, wherein the mono-nucleotide is attached to the linker on the base, the 3' ribose carbon, the 2' ribose carbon, alpha phosphate, beta phosphate or the gamma phosphate.

35. The probe of claim 9, wherein the donor-acceptor pair comprise a donor that is stimulated by application of an external stimulus to emit a stimulus to which the acceptor reacts to emit the characteristic signal.

36. The probe of claim 8, wherein each tag comprises a fluorophore.

37. The probe of claim 12, wherein the molecular linkers comprise linear polymers.

38. The probe of claim 37, wherein the linear polymers comprise nucleic acids.

39. The probe of claim 1, wherein the one or more molecular linkers maintain the polymerizing agent and the chemical moiety sufficiently spaced a distance from one another to avoid substantial entanglement of the polymerizing agent and the chemical moiety in an absence of the target nucleic acid molecule.

40. The probe of claim 13, wherein at least a portion of the molecular linker having a sufficient rigidity to reduce interaction of the polymerizing agent and the chemical moiety in the absence of the target nucleic acid molecule comprises a molecular rod.

41. The probe of claim 1, wherein the molecular linker comprises a tether, a molecular rod, or combinations thereof.

42. The probe of claim 13, wherein the molecular linker of sufficient rigidity comprises at least two tethers linked by a molecular rod.

43. The probe of claim 15, wherein the molecular linker consists of PEG.

44. The probe of claim 15, wherein the molecular linker is less than 187 Å in length.

45. The probe of claim 14, wherein the molecular linker comprises a dsDNA molecule of 40 nucleotides.

46. The probe of claim 14, wherein the dsDNA molecule comprises 10-150 nucleotides.

47. The probe of claim 16, wherein the polymerizing agent comprises a reverse transcriptase associated with a donor fluorophore.

48. The probe of claim 16, wherein the target nucleic acid molecule is DNA and the polymerizing agent is a DNA or RNA polymerase.

49. The probe of claim 16, wherein the target nucleic acid molecule is RNA and the polymerizing agent is reverse transcriptase.

50. The probe of claim 16, wherein the polymerizing agent is a Klenow fragment of DNA polymerase I.

51. The method of claim 18, wherein the emission of a sequence of signals is generated by luminescence resonance energy transfer (LRET) or Förster resonance energy transfer (FRET).

52. The method of claim 23, wherein the donor fluorophore is green fluorescent protein (GFP).

53. The method of claim 23, wherein the acceptor fluorophores are BODIPY, fluorescein, rhodamine green, Oregon green, or derivatives thereof.

54. The method of claim 20, wherein the donor fluorophore is excited by a luminescent molecule.

55. The method of claim 54, wherein the donor fluorophore is GFP and the luminescent molecule is chemiluminescent aequorin.

56. The method of claim 20, wherein the wherein the donor fluorophore is a luminescent molecule.

57. The method of claim 56, wherein the wherein the luminescent molecule is aequorin.

58. The method of claim 20, wherein the polymerizing agent is a GFP-polymerase.

59. The method of claim 24, wherein the polymerizing agent is fixed to the substrate by a linker.

60. The method of claim 59, wherein the linker is streptavidin-biotin, histidine-Ni, S-tag-S-protein, or glutathione-glutathione-S-transferase (GST).

61. The method of claim 27, wherein the polymerizing agents, target nucleic acid molecules, or oligonucleotide primers are fixed to the substrate in the predetermined pattern in channels which have been etched in an orderly array.

62. The method of claim 27, wherein the polymerizing agents, target nucleic acid molecules, or oligonucleotide primers are fixed to the substrate in the predetermined pattern by micropipetting droplets onto a substrate.

63. The method of claim 62, wherein micropipetting droplets onto a substrate is performed manually or with an automated arrayer.

64. The method of claim 18, wherein the sequence of signals is detected with a charge-coupled device (CCD) camera and converted into the nucleic acid sequence.

65. The method of claim 18, wherein the sequence of signals is stored in a computer-readable medium.

66. The method of claim 29, wherein the cell is present in a subject, and introduction of the oligonucleotide primer and the probe into the cell comprises administration of the oligonucleotide primer and the probe to the subject.

67. The probe of claim 1, wherein the polymerizing agent comprises a polymerizing agent-Tus fusion protein, and wherein the molecular linker comprises a ter sequence.

68. The probe of claim 1, wherein the polymerizing agent comprises an affinity tag.

69. A method of determining a nucleic acid sequence of a target nucleic acid molecule, comprising:
exposing the target nucleic acid molecule to the probe of claim 17 in the presence of an oligonucleotide primer and a mixture of hydrolyzable nucleotides that are capable of being incorporated into an elongating nucleic acid molecule by hybridizing with a complementary nucleotide in the target nucleic acid molecule, and replacing the nonhydrolyzable nucleotide analog that reversibly binds to the template nucleic acid molecule;
detecting emission of a sequence of signals comprising emission of a plurality of the characteristic signals that indicates pairing of the nucleotide analog on the molecular linker with its complementary nucleotide.

* * * * *

UNITED STATES PATENT AND TRADEMARK OFFICE
CERTIFICATE OF CORRECTION

| | |
|---|---|
| PATENT NO. | : 7,871,777 B2 |
| APPLICATION NO. | : 12/095973 |
| DATED | : January 18, 2011 |
| INVENTOR(S) | : Schneider et al. |

It is certified that error appears in the above-identified patent and that said Letters Patent is hereby corrected as shown below:

Column 16, line 16, "anon-hydrolyzable" should read --a non-hydrolyzable--

Column 17, line 60, "least contiguous" should read --least 10 contiguous--

Column 21, lines 22-23, "more a chemical" should read --more chemical--

Column 28, line 43, "*E. coli* U RNA" should read --*E. coli* RNA--

Column 32, line 37, "3040 nucleotides" should read --30-40 nucleotides--

Column 33, line 5, "By appropriate the choice" should read --By the appropriate choice--

Column 41, line 3, "The Tuster bond" should read --The Tus-*ter* bond--

Column 48, line 66, "95:1153843," should read --95:11538-43,--

Column 49, lines 50-51, "protein purified" should read --protein is purified--

Column 61, line 12, "[fluoropbore-408]" should read --[fluorophore-408]--

Column 64, line 24, "agent/12," should read --agent 12,--

Column 64, line 40, "the FR ET efficiency" should read --the FRET efficiency--

Column 67, line 34, "with a F is site)" should read --with a Fis site)--

Column 69, line 30, "299:682%, 2003)." should read --299:682-6, 2003).--

Column 70, line 49, "are not limited so particular" should read --are not limited to particular--

Column 94, claim 31, line 60, "linker" should read --linker.--

Column 96, claim 56, line 6, "wherein the wherein the donor" should read --wherein the donor--

Column 96, claim 57, line 8, "wherein the wherein the" should read --wherein the--

Signed and Sealed this
Sixth Day of December, 2011

David J. Kappos
*Director of the United States Patent and Trademark Office*